United States Patent
Tsukamoto et al.

(10) Patent No.: US 9,505,753 B2
(45) Date of Patent: Nov. 29, 2016

(54) INHIBITORS OF D-AMINO ACID OXIDASE

(71) Applicant: THE JOHNS HOPKINS UNIVERSITY, Baltimore, MD (US)

(72) Inventors: Takashi Tsukamoto, Ellicott City, MD (US); Barbara Stauch Slusher, Baltimore, MD (US); Dana V. Ferraris, Eldersburg, MD (US); Camilo Rojas, Baltimore, MD (US); Niyada Hin, Laurel, MD (US); Bridget Duvall, Nottingham, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/420,236

(22) PCT Filed: Aug. 8, 2013

(86) PCT No.: PCT/US2013/054127
§ 371 (c)(1),
(2) Date: Feb. 6, 2015

(87) PCT Pub. No.: WO2014/025993
PCT Pub. Date: Feb. 13, 2014

(65) Prior Publication Data
US 2015/0218156 A1    Aug. 6, 2015

Related U.S. Application Data

(60) Provisional application No. 61/680,923, filed on Aug. 8, 2012.

(51) Int. Cl.
| | |
|---|---|
| *C07D 253/07* | (2006.01) |
| *C07D 401/06* | (2006.01) |
| *C07D 403/06* | (2006.01) |
| *C07D 413/06* | (2006.01) |
| *C07D 417/06* | (2006.01) |
| *A61K 31/53* | (2006.01) |
| *A61K 31/5377* | (2006.01) |
| *A61K 31/541* | (2006.01) |
| *A61P 25/28* | (2006.01) |
| *C07D 471/04* | (2006.01) |
| *C07D 253/075* | (2006.01) |
| *A61K 31/198* | (2006.01) |
| *C07D 253/06* | (2006.01) |
| *C07D 409/06* | (2006.01) |

(52) U.S. Cl.
CPC .......... *C07D 471/04* (2013.01); *A61K 31/198* (2013.01); *A61K 31/53* (2013.01); *A61K 31/5377* (2013.01); *C07D 253/06* (2013.01); *C07D 253/075* (2013.01); *C07D 401/06* (2013.01); *C07D 403/06* (2013.01); *C07D 409/06* (2013.01)

(58) Field of Classification Search
CPC  C07D 253/07; C07D 401/06; C07D 403/06; C07D 413/06; C07D 417/06; A61K 31/53; A61K 31/5377; A61K 31/541
USPC ........... 544/182, 112; 514/242, 231.5, 227.8, 514/223.8
See application file for complete search history.

(56) References Cited

U.S. PATENT DOCUMENTS

| | | |
|---|---|---|
| 6,191,130 B1 | 2/2001 | Patoiseau et al. |
| 7,166,725 B2 | 1/2007 | Fang et al. |
| 7,579,370 B2 | 8/2009 | Heffernan et al. |
| 7,615,572 B2 | 11/2009 | Fang et al. |
| 2003/0185754 A1 | 10/2003 | Cohen et al. |
| 2008/0004327 A1 | 1/2008 | Heffernan et al. |
| 2008/0058395 A1 | 3/2008 | Heffernan et al. |
| 2010/0120740 A1 | 5/2010 | Heffernan et al. |
| 2011/0003862 A1 | 1/2011 | Brandish et al. |

FOREIGN PATENT DOCUMENTS

| | | |
|---|---|---|
| WO | 03039540 A2 | 5/2003 |
| WO | 2005089753 A2 | 9/2005 |
| WO | 2007039773 A1 | 4/2007 |
| WO | 2008089453 A2 | 7/2008 |
| WO | 2009018368 A1 | 2/2009 |
| WO | 2009-043884 A1 | 4/2009 |
| WO | 2009-056625 A1 | 5/2009 |
| WO | 2010058314 A1 | 5/2010 |
| WO | 2013004996 A1 | 1/2013 |
| WO | 2013027000 A1 | 2/2013 |
| WO | 2013073577 A1 | 5/2013 |

OTHER PUBLICATIONS

NL 8003011; CA 95:150683,1981. CAPLUS Abstract provided.*
Montavon et al. DE 2527291; CA 84:150646,1976. CAPLUS Abstract provided.*
PubChem Search-1, Dec. 1, 2015.*

(Continued)

*Primary Examiner* — Venkataraman Balasubramanian
(74) *Attorney, Agent, or Firm* — Ward and Smith, P.A.; Jeffrey W. Childers

(57) ABSTRACT

D-amino acid oxidase (DAAO) inhibitors and methods of their use, either alone or in combination with D-serine or D-alanine, to facilitate allosteric activation of NMDA receptor-mediated neurotransmission and methods of their use as therapeutic agents for treating a subject afflicted with one or more cognitive-disorders, such as schizophrenia, including subjects suffering from negative symptoms and cognitive impairments, post-traumatic stress disorder (PTSD), or pain, are disclosed.

5 Claims, 1 Drawing Sheet

(56) References Cited

OTHER PUBLICATIONS

PubChem Search-2, Dec. 1, 2015.*
International Search Report dated Nov. 20, 2013; International Application No. PCT/US2013/054127.
Singaravel Mohan et al., "Synthesis, Characterization and Biological Activity of Some Novel Sulphur Bridged Pyrazoles," International Journal of Pharma Sciences and Research, 2010, vol. 1, No. 9, pp. 391-398.
Arana GW. An overview of side effects caused by typical antipsychotics. J Clin Psychiatry. 2000;61 Suppl 8:5-11; discussion 2-3.
Shirzadi AA, Ghaemi SN. Side effects of atypical antipsychotics: extrapyramidal symptoms and the metabolic syndrome. Harv Rev Psychiatry. 2006;14(3):152-64.
Coyle JT. Glutamate and schizophrenia: beyond the dopamine hypothesis. Cell Mol Neurobiol. 2006;26(4-6):365-84.
Javitt DC, Zukin SR. Recent advances in the phencyclidine model of schizophrenia. Am J Psychiatry. 1991;148(10):1301-8.
Krystal JH, Karper LP, Seibyl JP, Freeman GK, Delaney R, Bremner JD, Heninger GR, Bowers MB, Jr., Charney DS. Subanesthetic effects of the noncompetitive NMDA antagonist, ketamine, in humans. Psychotomimetic, perceptual, cognitive, and neuroendocrine responses. Arch Gen Psychiatry. 1994;51(3):199-214.
Yang CR, Svensson KA. Allosteric modulation of NMDA receptor via elevation of brain glycine and D-serine: the therapeutic potentials for schizophrenia. Pharmacol Ther. 2008;120(3):317-32.
Leiderman E, Zylberman I, Zukin SR, Cooper TB, Javitt DC. Preliminary investigation of high-dose oral glycine on serum levels and negative symptoms in schizophrenia: an open-label trial. Biol Psychiatry. 1996;39(3):213-5.
Javitt DC. Glycine transport inhibitors for the treatment of schizophrenia: symptom and disease modification. Curr Opin Drug Discov Devel. 2009;12(4):468-78.
Bridges TM, Williams R, Lindsley CW. Design of potent GlyT1 inhibitors: in vitro and in vivo profiles. Curr Opin Mol Ther. 2008;10(6):591-601.
Hashimoto A, Nishikawa T, Hayashi T, Fujii N, Harada K, Oka T, Takahashi K. The presence of free D-serine in rat brain. FEBS Lett. 1992;296(1):33-6.
Nagata Y, Horiike K, Maeda T. Distribution of free D-serine in vertebrate brains. Brain Res. 1994;634(2):291-5.
Hashimoto A, Nishikawa T, Oka T, Takahashi K. Endogenous D-serine in rat brain: N-methyl-D-aspartate receptor-related distribution and aging. J Neurochem. 1993;60(2):783-6.
Oldendorf WH. Brain uptake of radiolabeled amino acids, amines, and hexoses after arterial injection. Am J Physiol. 1971;221(6):1629-39.
Hashimoto A, Chiba Y. Effect of systemic administration of D-serine on the levels of D- and L-serine in several brain areas and periphery of rat. Eur J Pharmacol. 2004;495(2-3):153-8.
Matsui T, Sekiguchi M, Hashimoto A, Tomita U, Nishikawa T, Wada K. Functional comparison of D-serine and glycine in rodents: the effect on cloned NMDA receptors and the extracellular concentration. J Neurochem. 1995;65(1):454-8.
Tsai G, Yang P, Chung LC, Lange N, Coyle JT. D-serine added to antipsychotics for the treatment of schizophrenia. Biol Psychiatry. 1998;44(11):1081-9.
Heresco-Levy U, Javitt DC, Ebstein R, Vass A, Lichtenberg P, Bar G, Catinari S, Ermilov M. D-serine efficacy as add-on pharmacotherapy to risperidone and olanzapine for treatment-refractory schizophrenia. Biol Psychiatry. 2005;57(6):577-85.
Ganote CE, Peterson DR, Carone FA. The nature of D-serine-induced nephrotoxicity. Am J Pathol. 1974;77(2):269-82.
Williams RE, Lock EA. Sodium benzoate attenuates d-serine induced nephrotoxicity in the rat. Toxicology. 2005;207(1):35-48.
Burnet PW, Eastwood SL, Bristow GC, Godlewska BR, Sikka P, Walker M, Harrison PJ. D-amino acid oxidase activity and expression are increased in schizophrenia. Mol Psychiatry. 2008;13(7):658-60. PMCID: 2629619.
Madeira C, Freitas ME, Vargas-Lopes C, Wolosker H, Panizzutti R. Increased brain D-amino acid oxidase (DAAO) activity in schizophrenia. Schizophr Res. 2008;101(1-3):76-83.
Curti B, Ronchi S, Simonetta PM. D- and L-Amino Acid Oxidases. In: Muller F, editor. Chemistry and Biochemistry of Flavoenzyme. Boca Raton, FL: CRC Press; 1992. p. 69-94.
Adage T, Trillat AC, Quattropani A, Perrin D, Cavarec L, Shaw J, Guerassimenko O, Giachetti C, Greco B, Chumakov I, Halazy S, Roach A, Zaratin P. In vitro and in vivo pharmacological profile of AS057278, a selective d-amino acid oxidase inhibitor with potential anti-psychotic properties. Eur Neuropsychopharmacol. 2008;18(3):200-14.
Smith SM, Uslaner JM, Yao L, Mullins CM, Surles NO, Huszar SL, McNaughton CH, Pascarella DM, Kandebo M, Hinchliffe RM, Sparey T, Brandon NJ, Jones B, Venkatraman S, Young MB, Sachs N, Jacobson MA, Hutson PH. The behavioral and neurochemical effects of a novel D-amino acid oxidase inhibitor compound 8 [4H-thieno [3,2- b]pyrrole-5-carboxylic acid] and D-serine. J Pharmacol Exp Ther. 2009;328(3):921-30.
Horiike K, Tojo H, Arai R, Nozaki M, Maeda T. D-amino-acid oxidase is confined to the lower brain stem and cerebellum in rat brain: regional differentiation of astrocytes. Brain Res. 1994;652(2):297-303.
Hashimoto A, Nishikawa T, Konno R, Niwa A, Yasumura Y, Oka T, Takahashi K. Free D-serine, D-aspartate and D-alanine in central nervous system and serum in mutant mice lacking D-amino acid oxidase. Neurosci Lett. 1993;152(1-2):33-6.
Boomsma F, Meerwaldt JD, Man In't Veld AJ, Hovestadt A, Schalekamp MA. Treatment of idiopathic parkinsonism with L-dopa in the absence and presence of decarboxylase inhibitors: effects on plasma levels of L-dopa, dopa decarboxylase, catecholamines and 3-O-methyl-dopa. J Neurol. 1989;236(4):223-30.
Ferraris D, Duvall B, Ko YS, Thomas AG, Rojas C, Majer P, Hashimoto K, Tsukamoto T. Synthesis and biological evaluation of D-amino acid oxidase inhibitors. J Med Chem. 2008;51(12):3357-9.
Mattevi A, Vanoni MA, Todone F, Rizzi M, Teplyakov A, Coda A, Bolognesi M, Curti B. Crystal structure of D-amino acid oxidase: a case of active site mirror-image convergent evolution with flavocytochrome b2. Proc Natl Acad Sci USA. 1996;93(15):7496-501.
Fukushima T, Kawai J, Imai K, Toyo'Oka T. Simultaneous determination of D- and L-serine in rat brain microdialysis sample using a column-switching HPLC with fluorimetric detection. Biomed Chromatogr. 2004;18(10):813-9.
Hashimoto K, Fujita Y, Horio M, Kunitachi S, Iyo M, Ferraris D, Tsukamoto T. Co-administration of a D-amino acid oxidase inhibitor potentiates the efficacy of D-serine in attenuating prepulse inhibition deficits after administration of dizocilpine. Biol Psychiatry. 2009;65(12):1103-6.
Rishton GM. Nonleadlikeness and leadlikeness in biochemical screening. Drug Discov Today. 2003;8(2):86-96.
Duplantier AJ, Becker SL, Bohanon MJ, Borzilleri KA, Chrunyk BA, Downs JT, Hu LY, El-Kattan A, James LC, Liu S, Lu J, Maklad N, Mansour MN, Mente S, Piotrowski MA, Sakya SM, Sheehan S, Steyn SJ, Strick CA, Williams VA, Zhang L. Discovery, SAR, and pharmacokinetics of a novel 3-hydroxyquinolin-2(1 H)-one series of potent D-amino acid oxidase (DAAO) inhibitors. J Med Chem. 2009;52(11):3576-85.
Sparey T, Abeywickrema P, Almond S, Brandon N, Byrne N, Campbell A, Hutson PH, Jacobson M, Jones B, Munshi S, Pascarella D, Pike A, Prasad GS, Sachs N, Sakatis M, Sardana V, Venkatraman S, Young MB. The discovery of fused pyrrole carboxylic acids as novel, potent D-amino acid oxidase (DAO) inhibitors. Bioorg Med Chem Lett. 2008;18(11):3386-91.
Seillier A, Giuffrida A. Evaluation of NMDA receptor models of schizophrenia: divergences in the behavioral effects of sub-chronic PCP and MK-801. Behav Brain Res. 2009;204(2):410-5.
Kellendonk C, Simpson EH, Kandel ER. Modeling cognitive endophenotypes of schizophrenia in mice. Trends Neurosci. 2009;32(6):347-58.

(56) References Cited

OTHER PUBLICATIONS

Harrison PJ, Weinberger DR. Schizophrenia genes, gene expression, and neuropathology: on the matter of their convergence. Mol Psychiatry. 2005;10(1):40-68.
Jaaro-Peled H, Hayashi-Takagi A, Seshadri S, Kamiya A, Brandon NJ, Sawa A. Neurodevelopmental mechanisms of schizophrenia: understanding disturbed postnatal brain maturation through neuregulin-1-ErbB4 and DISC1. Trends Neurosci. 2009;32(9):485-95.
Hikida T, Jaaro-Peled H, Seshadri S, Oishi K, Hookway C, Kong S, Wu D, Xue R, Andrade M, Tankou S, Mori S, Gallagher M, Ishizuka K, Pletnikov M, Kida S, Sawa A. Dominant-negative DISC1 transgenic mice display schizophrenia-associated phenotypes detected by measures translatable to humans. Proc Natl Acad Sci USA. 2007;104(36):14501-6. PMCID: 1964873.
Li W, Zhou Y, Jentsch JD, Brown RA, Tian X, Ehninger D, Hennah W, Peltonen L, Lonnqvist J, Huttunen MO, Kaprio J, Trachtenberg JT, Silva AJ, Cannon TD. Specific developmental disruption of disrupted-in-schizophrenia-1 function results in schizophrenia-related phenotypes in mice. Proc Natl Acad Sci U S A. 2007;104(46):18280-5. PMCID: 2084334.
Pletnikov MV, Ayhan Y, Nikolskaia O, Xu Y, Ovanesov MV, Huang H, Mori S, Moran TH, Ross CA. Inducible expression of mutant human DISC1 in mice is associated with brain and behavioral abnormalities reminiscent of schizophrenia. Mol Psychiatry. 2008;13(2):173-86, 15.
Reddy ACS, Narsaiah B, Venkataratnam RV. A Novel Method for the Synthesis of Isoxazolo and Pyrazolo Pyridines Using Hypervalent Iodine Reagent. Synthetic Commun. 1997;27(13):2217-22.
Drummond J, Johnson G, Nickell DG, Ortwine DF, Bruns RF, Welbaum B. Evaluation and synthesis of aminohydroxyisoxazoles and pyrazoles as potential glycine agonists. J Med Chem. 1989;32(9):2116-28.
Trivedi K, Sethan S. Notes—3-Hydroxycoumarins. J Org Chem. 1980;25(10):1817-9.
Pavé G, Chalard P, Viaud-Massuard M-C, Troin Y, Guillaumet G. New Efficient Synthesis of Pyrido[2,3-c] and Pyrido[3,2-c]coumarin Derivatives. Synlett. 2003(07):987-90.
Bailly F, Maurin C, Teissier E, Vezin H, Cotelle P. Antioxidant properties of 3-hydroxycoumarin derivatives. Bioorg Med Chem. 2004;12(21):5611-8.
Chiyoda T, Iida K, Takatori K, Kajiwara M. Convenient Synthesis of 1,2-Benzisothiazol-3(2H)-ones by Cyclization Reaction of Acyl Azide. Synlett. 2000;2000(10):1427-8.
Sekikawa I, Nishie J, Tono-Oka S, Tanaka Y, Kakimoto S. Antituberculous compounds. XXVIII. Synthesis of pyrazolopyridines. J Heterocyclic Chem. 1973;10(6):931-2.
Wyrick SD, Voorstad PJ, Cocolas G, Hall IH. Hypolipidemic activity of phthalimide derivatives. 7. Structure-activity studies of indazolone analogues. J Med Chem. 1984;27(6):768-72.
Valgeirsson J, Nielsen EO, Peters D, Mathiesen C, Kristensen AS, Madsen U. Bioisosteric modifications of 2-arylureidobenzoic acids: selective noncompetitive antagonists for the homomeric kainate receptor subtype GluR5. J Med Chem. 2004;47(27):6948-57.

Usami N, Kitahara K, Ishikura S, Nagano M, Sakai S, Hara A. Characterization of a major form of human isatin reductase and the reduced metabolite. Eur J Biochem. 2001;268(22):5755-63.
Cooley JH, Jacobs PT. Oxidative ring closure of 1-benzyloxy-3-arylureas to 1-benzyloxybenzimidazolones. J Org Chem. 1975;40(5):552-7.
Cafiero C, A. P, French CS, McFarlane MD, Mackie RK, Smith DM. o-Nitroaniline derivatives. Part 14. Cyclizations leading to benzimidazole N-oxides, N-hydroxybenzimidazolones and N-hydroxyqinoxaline-2,3-diones: a mechanistic borderline. J Chem Soc, Perkin Trans 1. 1997:1375-84.
Veber DF, Johnson SR, Cheng HY, Smith BR, Ward KW, Kopple KD. Molecular properties that influence the oral bioavailability of drug candidates. J Med Chem. 2002;45(12):2615-23.
Lipina T, Labrie V, Weiner I, Roder J. Modulators of the glycine site on NMDA receptors, D-serine and ALX 5407, display similar beneficial effects to clozapine in mouse models of schizophrenia. Psychopharmacology (Berl). 2005;179(1):54-67.
Hikida T, Mustafa AK, Maeda K, Fujii K, Barrow RK, Saleh M, Huganir RL, Snyder SH, Hashimoto K, Sawa A. Modulation of D-serine levels in brains of mice lacking PICK1. Biol Psychiatry. 2008;63(10):997-1000. PMCID: 2715963.
Labrie V, Fukumura R, Rastogi A, Fick LJ, Wang W, Boutros PC, Kennedy JL, Semeralul MO, Lee FH, Baker GB, Belsham DD, Barger SW, Gondo Y, Wong AH, Roder JC. Serine racemase is associated with schizophrenia susceptibility in humans and in a mouse model. Hum Mol Genet. 2009;18(17):3227-43. PMCID: 2722985.
Sethuraman R, Lee TL, Tachibana S. D-serine regulation: a possible therapeutic approach for central nervous diseases and chronic pain. Mini Rev Med Chem. 2009;9(7):813-9.
McDonald, A.J., 1996. Glutamate and aspartate immunoreactive neurons of the rat basolateral amygdale: colocalization of excitatory amino acids and projections to the limbic circuit. Journal of Comparative Neurology 365, 367-379.
Heresco-Levy U, Vass A, Boaz B, Wolosker H, Dumin E, Balan L, Deutsch L, and Kremer I, 2009. International Journal of Neuropsychopharmacology, 12. 1275-1282.
Cook AJ, Woolf CJ, Wall PD, McMahon SB, 1987. Dynamic receptive field plasticity in rat spinal cord dorsal horn following C-primary afferent input. Nature 325:151-153.
Ying B, Lu N, Zhang YQ, and Zhao ZQ, 2006. Involvement of spinal glia in tetanically sciatic stimulation-induced bilateral mechanical allodynia in rats. Biochem Biophys Res Commun 340: 1264-1272.
Lu J-M, Gong N, Wang Y-C, and Wang Y-X, 2012. D-Amino acid oxidase-mediated increase in spinal hydrogen peroxide is mainly responsible for formalin-induced tonic pain. British J of Pharmacology 165:1941-1955.
Media Release, "Phase II study with first-in-class investigational drug demonstrates improvement in negative symptoms in patients with schizophrenia," F. hoffmann-la roche, ltd. (Dec. 6, 2010).
Kantrowitz J. T., et al., "High dose D-serine in the treatment of schizophrenia," Schizophrenia Research 121:125-130 (2010).
Maekawa M., et al., "D-Amino-acid Oxidase Is Involved in D-Serine-lnduced Nephrotoxicity," Chem. Res. Toxicol. 18:1678-1682 (2005).

* cited by examiner

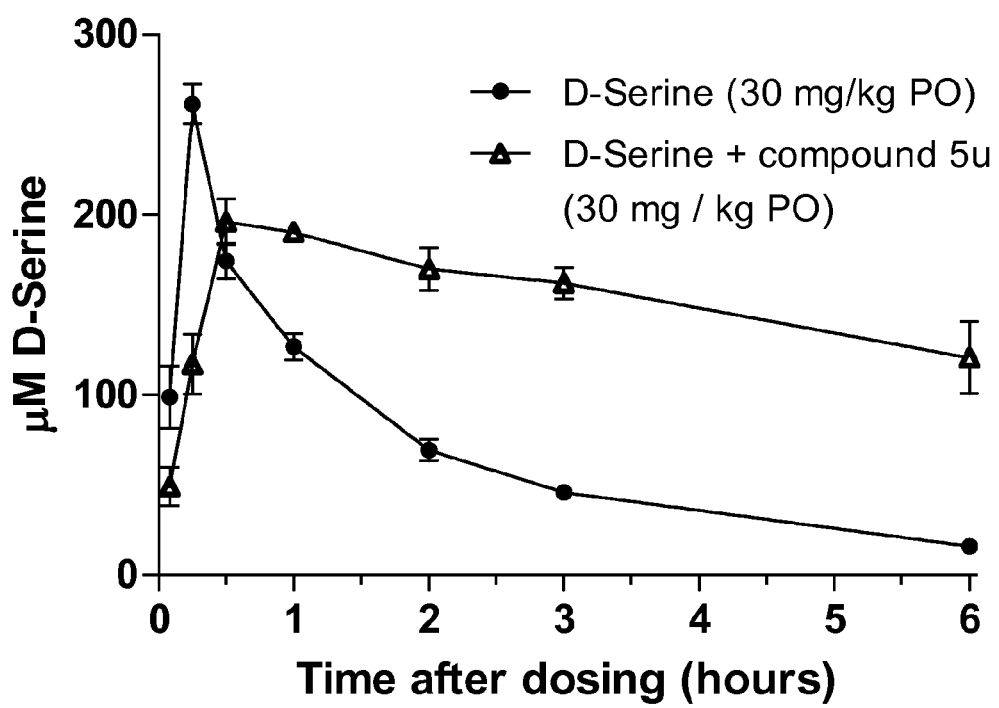

INHIBITORS OF D-AMINO ACID OXIDASE

CROSS-REFERENCE TO RELATED APPLICATIONS

This application is a 35 U.S.C. §371 U.S. national phase entry of International Application No. PCT/US13/54127 having an international filing date of Aug. 8, 2013, which claims the benefit of U.S. Provisional Application No. 61/680,923, filed Aug. 8, 2012, which are incorporated herein by reference in their entirety.

FEDERALLY SPONSORED RESEARCH OR DEVELOPMENT

This invention was made with government support under 5R01MH091387-03 awarded by the National Institutes of Health (NIH). The government has certain rights in the invention.

BACKGROUND

D-amino acid oxidase (DAAO), a flavoenzyme expressed in the mammalian liver, kidneys, and brain, catalyzes the oxidative deamination of D-amino acids. The physiological role of DAAO in the kidney and liver is detoxification of accumulated D-amino acids. DAAO and the D-amino acids that this enzyme regulates have been implicated in a variety of physiological processes. For example, D-aspartate regulates hormone release, D-arginine affects pathways that regulate arterial pressure, and elevated D-alanine content has been found in the gray matter of Alzheimer's patients. In addition, D-serine has been found to play an important role as a neurotransmitter in the human central nervous system by binding to the N-methyl D-aspartate (NMDA) receptor as an agonist at the glycine site. This observation suggests that D-serine plays a broad role in synaptic events associated with development, plasticity, learning, memory and excitotoxicity.

Cumulative evidence suggests that allosteric activation of the NMDA receptor through the glycine modulatory site provides new therapeutic potential for treating cognitive-related disorders, such as schizophrenia. D-Serine, an endogenous agonist at the glycine modulatory site, has been shown to be effective in treating positive, negative, and cognitive symptoms of schizophrenia in clinical studies. Despite encouraging clinical data, clinical development of D-serine likely will face obstacles, in part, because of the high dosages required for efficacy. This requirement is primarily due to the substantial metabolism of peripherally administered D-serine by DAAO. DAAO-mediated metabolism of D-serine not only limits the bioavailability of D-serine, but it also has the potential to induce kidney toxicity (nephrotoxicity) through the generation of hydrogen peroxide. Compounds capable of blocking or inhibiting DAAO-mediated D-serine metabolism, which could substantially lower the dosages required for efficacy while preventing hydrogen peroxide-induced peripheral toxicity, could be useful for treating schizophrenia.

SUMMARY

In some aspects, the presently disclosed subject matter provides a compound of formula (I):

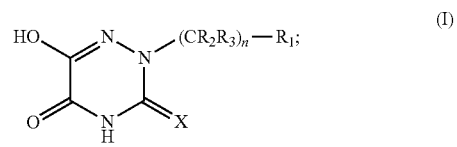

wherein: n is an integer selected from the group consisting of 0, 1, 2, and 3; X is oxygen or sulfur; $R_1$ is selected from the group consisting of H, substituted or unsubstituted straight-chain or branched alkyl, amino, carboxyl, substituted or unsubstituted heteroalkyl, substituted or unsubstituted cycloalkyl, substituted or unsubstituted cycloheteroalkyl, substituted or unsubstituted aryl, and substituted or unsubstituted heteroaryl; and each occurrence of $R_2$ and $R_3$ is independently selected from the group consisting of H, hydroxyl, and halogen, or $R_2$ and $R_3$ together can be oxygen (e.g., the linking group $CR_2R_3$ is —C(=O)—); under the provisos that if n is 0, $R_1$ cannot be methyl or if n is 1, then $R_1$, $R_2$ and $R_3$ cannot each be H; or a pharmaceutically acceptable salt thereof.

In some aspects, the compound of formula (I) is a D-amino acid oxidase (DAAO) inhibitor that is useful for treating a disorder or a condition that can be treated by inhibiting DAAO activity including, but not limited to, cognitive-related disorders, post-traumatic stress disorder (PTSD), and disorders involving pain.

In particular aspects, the presently disclosed subject matter provides a method for treating a cognitive-related disorder in a subject in need of treatment thereof, the method comprising administering to the subject a therapeutically effective amount of a compound of formula (I), either alone or in combination with a therapeutically effective amount of D-serine or D-alanine, or a pharmaceutically effective salt thereof. In certain aspects, the cognitive-related disorder includes schizophrenia and related disorders, psychosis, bipolar disorder, psychotic episodes of anxiety, anxiety associated with psychosis, psychotic mood disorders, severe major depressive disorder, mood disorders associated with psychotic disorders, acute mania, depression associated with bipolar disorder, mood disorders associated with schizophrenia, dementia, age-related dementia, senile dementia of the Alzheimer's type, memory disorders, neuropathic pain, and any combination thereof.

In other aspects, the presently disclosed subject matter provides a method for treating post-traumatic stress disorder in a subject in need of treatment thereof, the method comprising administering to the subject a therapeutically effective amount of a compound of formula (I), either alone or in combination with a therapeutically effective amount of D-serine or D-alanine, or a pharmaceutically effective salt thereof, to inhibit D-amino acid oxidase (DAAO) activity in the subject.

In other aspects, the presently disclosed subject matter provides a method for treating pain in a subject in need of treatment thereof, the method comprising administering to the subject an amount of a compound of formula (I), or a pharmaceutically effective salt thereof, effective to inhibit D-amino acid oxidase (DAAO) activity in the subject.

In other aspects, the presently disclosed subject matter provides a method for inhibiting the activity of D-amino acid oxidase (DAAO) in a subject, the method comprising administering to a subject at least one compound of formula (I) in an amount effective to inhibit the activity of DAAO in the subject.

In other aspects, the presently disclosed subject matter provides a method for increasing the levels of D-serine in a subject, the method comprising administering to a subject at least one compound of formula (I) in an amount effective to increase the levels of D-serine in the subject.

In other aspects, the presently disclosed subject matter provides a method for suppressing the levels of hydrogen peroxide generation in a subject, the method comprising administering to a subject at least one compound of formula (I) in an amount effective to suppress the levels of hydrogen peroxide in the subject.

In yet other aspects, the presently disclosed subject matter provides a composition comprising a pharmaceutically effective amount of a compound of formula (I) or a pharmaceutically acceptable salt thereof, and a pharmaceutically acceptable carrier. In particular aspects, the composition comprises a therapeutically effective combination of D-serine or D-alanine and a compound of formula (I).

Certain aspects of the presently disclosed subject matter having been stated hereinabove, which are addressed in whole or in part by the presently disclosed subject matter, other aspects will become evident as the description proceeds when taken in connection with the accompanying Examples as best described herein below.

BRIEF DESCRIPTION OF THE FIGURE

Having thus described the presently disclosed subject matter in general terms, reference will now be made to the accompanying FIGURE, which are not necessarily drawn to scale, and wherein:

FIG. 1 shows the effect of 6-hydroxy-2-(naphthalen-1-ylmethyl)-1,2,4-triazine-3,5(2H,4H)-dione on D-serine levels in plasma.

DETAILED DESCRIPTION

The presently disclosed subject matter now will be described more fully hereinafter with reference to the accompanying Examples, in which some, but not all embodiments of the presently disclosed subject matter are illustrated. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Examples. Therefore, it is to be understood that the presently disclosed subject matter is not to be limited to the specific embodiments disclosed and that modifications and other embodiments are intended to be included within the scope of the appended claims.

I. INHIBITORS OF D-AMINO ACID OXIDASE

A. Background

Despite the increased number of antipsychotics that have become available in the last several decades, unmet medical needs in treating cognitive-related disorders, such as schizophrenia, remain substantial. Only a subgroup of patients fully responds to the currently available antipsychotics. Those patients who do respond still have to contend with the well-documented extrapyramidal, metabolic, or other side effects of these medications. Arana G. W., "An overview of side effects caused by typical antipsychotics," *J. Clin. Psychiatry* 61 Suppl 8:5-11; discussion 2-3 (2000); Shirzadi A. A., Ghaemi S. N., "Side effects of atypical antipsychotics: extrapyramidal symptoms and the metabolic syndrome," *Harv. Rev. Psychiatry*, 14(3):152-64 (2006).

One of the most fundamental issues in antipsychotic treatment is that, for decades, theories of schizophrenia have focused on a single neurotransmitter, dopamine. For this reason, all current antipsychotics exert their effects primarily by blocking D2 dopamine receptors. Although the typical and second generation antipsychotics are effective at reducing positive symptoms of schizophrenia, they provide, with the possible exception of clozapine, limited benefit for patients substantially disabled due to negative symptoms and cognitive impairments.

The need for truly novel antipsychotics prompted some researchers to shift the emphasis from the dopamine hypothesis of psychosis to other mechanistic theories to better understand the components of the disorder that are resistant to current treatment. In particular, attention has been given to deficiencies in glutamate-mediated neurotransmission through NMDA-type glutamate receptors. Coyle J. T., "Glutamate and schizophrenia: beyond the dopamine hypothesis," *Cell Mol. Neurobiol.* 26(4-6):365-84 (2006). The NMDA receptor hypofunction hypothesis of schizophrenia has emerged from the observation that NMDA receptor antagonists, such as phencyclidine (PCP) and ketamine, induce psychotic and neurocognitive symptoms that closely resemble the symptoms of schizophrenia. Javitt D. C., Zukin S. R., "Recent advances in the phencyclidine model of schizophrenia," *Am. J. Psychiatry* 148(10):1301-8 (1991); Krystal J. H., et al., "Subanesthetic effects of the noncompetitive NMDA antagonist, ketamine, in humans. Psychotomimetic, perceptual, cognitive, and neuroendocrine responses," *Arch. Gen. Psychiatry* 51(3):199-214 (1994).

Several lines of investigation, including imaging, genetic, and postmortem studies have provided further support for this hypothesis. Coyle J. T., "Glutamate and schizophrenia: beyond the dopamine hypothesis," *Cell Mol. Neurobiol.* 26(4-6):365-84 (2006). Among them, the most compelling evidence is that pharmacological activation of the NMDA receptors is effective at ameliorating symptoms of schizophrenia in clinical studies. For these reasons, NMDA receptor agonists represent an opportunity for novel antipsychotics. Yang C. R., Svensson K. A., "Allosteric modulation of NMDA receptor via elevation of brain glycine and D-serine: the therapeutic potentials for schizophrenia," *Pharmacol. Ther.* 120(3):317-32 (2008).

As excessive stimulation of the NMDA receptor glutamate-binding site may cause excitotoxic damage to neurons, drug discovery efforts have focused on increasing glutamatergic neurotransmission by directly or indirectly activating the glycine modulatory site on the NMDA receptors. For example, treatment with high doses of glycine (30-60 g/day), an endogenous agonist at the glycine modulatory site, showed significant improvement in negative symptoms and cognitive impairments in chronic schizophrenic subjects receiving concurrent typical antipsychotics. Leiderman E., et al., "Preliminary investigation of high-dose oral glycine on serum levels and negative symptoms in schizophrenia: an open-label trial," *Biol. Psychiatry*, 39(3):213-5 (1996).

These clinical findings not only support the NMDA receptor hypofunction hypothesis of schizophrenia, but they also demonstrate that the enhancement of NMDA receptor signaling has the potential to address negative symptoms and cognitive deficits, where existing antipsychotics have failed to show significant efficacy. Glycine itself, however, might not be an ideal therapeutic agent because (i) glycine has poor blood-brain barrier permeability, requiring an unrealistically high dose (60 g/day); and (ii) in addition to the glycine/NMDA site, glycine acts on the inhibitory strychnine-sensitive glycine receptor, possibly causing CNS side effects, particularly in chronic dosing.

To overcome these problems, efforts are currently being made to develop inhibitors of the glycine transporter type-1 (GlyT1). Javitt D. C., "Glycine transport inhibitors for the treatment of schizophrenia: symptom and disease modification," *Curr. Opin. Drug Discov. Devel.* 12(4):468-78 (2009). GlyT1 is co-localized with NMDA receptors and regulates synaptic glycine levels in the immediate vicinity of the NMDA receptor complex. Thus, a brain permeable selective GlyT1 inhibitor could offer a better alternative to glycine administration in increasing synaptic glycine levels. For example, sarcosine, an endogenous inhibitor of GlyT1, reduces negative symptoms, cognitive deficits, and positive symptoms in a placebo controlled trial in chronic schizophrenics receiving concurrent antipsychotics. Some new GlyT1 inhibitors are currently being tested in clinical trials. In particular, RG1678 has been reported to demonstrate improvement in negative symptoms in patients with schizophrenia. See, Media Release, "Phase II study with first-in-class investigational drug demonstrates improvement in negative symptoms in patients with schizophrenia," F. Hoffmann-La Roche, Ltd. (Dec. 6, 2010). See also, Bridges T. M., "Design of potent GlyT1 inhibitors: in vitro and in vivo profiles," *Curr. Opin. Mol. Ther.* 10(6):591-601 (2008).

Another endogenous agonist at the glycine modulatory site on the NMDA receptor is D-serine. Despite the presumption that D-amino acids are uncommon in mammalian tissues, a considerable concentration of endogenous D-serine is distributed in mouse and rat brain. Hashimoto A., et al., "The presence of free D-serine in rat brain," *FEBS Lett.* 296(1):33-6 (1992); Nagata Y., et al. "Distribution of free D-serine in vertebrate brains," *Brain Res.* 634(2):291-5 (1994). D-Serine is formed through the catalytic racemization of L-serine by serine racemase. Interestingly, localization of serine racemase in the brain correlates closely with NMDA receptors, suggesting that the predominant endogenous ligand for the glycine modulatory site is D-serine. Hashimoto A., et al., "Endogenous D-serine in rat brain: N-methyl-D-aspartate receptor-related distribution and aging," *J. Neurochem.* 60(2):783-6 (1993).

D-Serine offers several pharmacological advantages over glycine, including, but not limited to: (i) D-Serine is more permeable than glycine to the blood-brain barrier, Oldendorf W. H., "Brain uptake of radiolabeled amino acids, amines, and hexoses after arterial injection," *Am. J. Physiol.* 221(6): 1629-39 (1971), and exhibits a long half-life in cortex upon peripheral administration; Hashimoto A., Chiba Y., "Effect of systemic administration of D-serine on the levels of D- and L-serine in several brain areas and periphery of rat," *Eur. J. Pharmacol.* 495(2-3):153-8 (2004); (ii) D-serine is more potent than glycine at activating the glycine modulatory site of the NMDA receptors; Matsui T., et al., "Functional comparison of D-serine and glycine in rodents: the effect on cloned NMDA receptors and the extracellular concentration," *J. Neurochem.* 65(1):454-8 (1995); and (iii) since there is no known signal transduction site modulated by D-serine other than the glycine modulatory site, D-serine can facilitate NMDA receptor function without affecting other CNS receptors.

Chronic schizophrenic patients receiving D-serine treatment with concomitant neuroleptic therapy showed significant improvements in their positive, negative, and cognitive symptoms. Tsai G, et al., "D-serine added to antipsychotics for the treatment of schizophrenia," *Biol. Psychiatry,* 44(11): 1081-9 (1998). This effect on all three symptom domains by D-serine has been replicated in a placebo-controlled trial in chronic schizophrenic subjects receiving concurrent antipsychotics. Heresco-Levy U., et al., "D-serine efficacy as add-on pharmacotherapy to risperidone and olanzapine for treatment-refractory schizophrenia," *Biol. Psychiatry,* 57(6): 577-85 (2005). Further clinical development of D-serine, however, could be hampered by the high doses of D-serine (in excess of 2 grams per day) required for the optimal treatment of schizophrenia. Tsai G., et al., "D-serine added to antipsychotics for the treatment of schizophrenia," *Biol. Psychiatry,* 44(11):1081-9 (1998); Heresco-Levy U., et al., "D-serine efficacy as add-on pharmacotherapy to risperidone and olanzapine for treatment-refractory schizophrenia," *Biol. Psychiatry* 57(6):577-85 (2005).

It could be argued that the high doses should not present a problem for clinical use since D-serine is endogenously present in the brain. High doses of D-serine, however, were reported to cause selective necrosis to the pars recta region of the renal proximal tubules in the rat. Ganote C. E., et al., "The nature of D-serine-induced nephrotoxicity," *Am. J. Pathol.* 77(2):269-82 (1974). Indeed, one patient receiving high dose of D-serine (120 mg/kg) showed a nephrotoxic-like pattern in an open label clinical trial. Kantrowitz J. T., et al., "High dose D-serine in the treatment of schizophrenia," *Schizophrenia Research* 121:125-130 (2010). Recent studies revealed that the mechanism of D-serine-induced nephrotoxicity is associated with oxidative stress caused by hydrogen peroxide, a byproduct of D-amino acid oxidase (DAAO)-mediated metabolism of D-serine in the kidneys. Williams R. E., Lock E. A., "Sodium benzoate attenuates d-serine induced nephrotoxicity in the rat," *Toxicology* 207 (1):35-48 (2005); see also Maekawa M., et al., "D-Amino-acid Oxidase Is Involved in D-Serine-Induced Nephrotoxicity," *Chem. Res. Toxicol.* 18:1678-1682 (2005).

DAAO (EC 1.4.3.3) is a flavoenzyme that catalyzes the oxidation of D-amino acids to the corresponding α-keto acids. In mammals, DAAO is present in kidneys, liver, and brain. Interestingly, two recent independent studies demonstrated that DAAO expression and activity are elevated in schizophrenia. Burnet P. W., et al., "D-amino acid oxidase activity and expression are increased in schizophrenia," *Mol. Psychiatry* 13(7):658-60 (2008). Madeira C., et al., "Increased brain D-amino acid oxidase (DAAO) activity in schizophrenia," *Schizophr Res.* 101(1-3):76-83 (2008).

Since the highest DAAO activity is found in the kidneys, Curti B., et al., "D- and L-Amino Acid Oxidases," In: Muller F., ed. Chemistry and Biochemistry of Flavoenzyme. Boca Raton, Fla.: CRC Press; pp. 69-94 (1992), a substantial amount of orally administered D-serine is metabolized in the kidneys, contributing to its rapid clearance. These findings suggest that inhibition of DAAO would exert dual beneficial effects on D-serine therapy: (i) enhancement of D-serine bioavailability; and (ii) suppression of hydrogen peroxide generation in the kidneys. Thus, DAAO inhibitors might address issues associated with clinical use of D-serine and salvage the most clinically efficacious glycine modulatory site agonist.

Analogous to the use of GlyT1 inhibitors to increase synaptic levels of glycine, some researchers have pursued inhibition of DAAO in the brain to increase endogenous D-serine levels. Adage T., et al., "In vitro and in vivo pharmacological profile of AS057278, a selective d-amino acid oxidase inhibitor with potential anti-psychotic properties," *Eur. Neuropsychopharmacol* 18(3):200-14 (2008); Smith S. M., et al., "The behavioral and neurochemical effects of a novel D-amino acid oxidase inhibitor compound 8 [4H-thieno[3,2-b]pyrrole-5-carboxylic acid] and D-serine," *J. Pharmacol Exp. Ther.* 328(3):921-30 (2009).

This approach has shown limited success even when the brain concentration of a DAAO inhibitor is over 100-fold higher than its $IC_{50}$ value for DAAO. Smith S. M. et al., "The behavioral and neurochemical effects of a novel D-amino acid oxidase inhibitor compound 8 [4H-thieno[3,2-b]pyrrole-5-carboxylic acid] and D-serine," *J. Pharmacol Exp. Ther.* 328(3):921-30 (2009). Without wishing to be bound to any one particular theory, it could be speculated that the concentration of D-serine required for enhancing the activity of NMDA receptors is much greater than can be achieved by DAAO inhibition alone. The more fundamental mechanistic issue associated with this approach could be that there is little overlap in distribution of DAAO and the NMDA receptors in the brain. Horiike K., et al., "D-amino-acid oxidase is confined to the lower brain stem and cerebellum in rat brain: regional differentiation of astrocytes," *Brain Res.* 652(2):297-303 (1994).

Therefore, the treatment with a DAAO inhibitor alone may, at best, increase the levels of D-serine in the regions of the brain where the expression of the NMDA receptors is limited. In fact, mutant mice lacking DAAO activity were found to exhibit only subtle increases in D-serine in the forebrain. Hashimoto A., et al., "Free D-serine, D-aspartate and D-alanine in central nervous system and serum in mutant mice lacking D-amino acid oxidase," *Neurosci. Lett.* 152(1-2):33-6 (1993). This observation is consistent with the findings that neither PCP-induced PPI deficits nor hyperlocomotion in mice were normalized by acute administration of a DAAO inhibitor alone, while chronic treatment for 28 days had a subtle but significant effect at some doses. Adage T., et al., "In vitro and in vivo pharmacological profile of AS057278, a selective d-amino acid oxidase inhibitor with potential anti-psychotic properties," *Eur. Neuropsychopharmacol* 18(3):200-14 (2008).

Accordingly, as provided herein below, the presently disclosed subject matter provides compounds and compositions comprising compounds of formula (I), which are D-amino acid oxidase (DAAO) inhibitors that are useful for treating a disorder or a condition including, but not limited to, cognitive-related disorders, post-traumatic stress disorder (PTSD), and disorders involving pain, that can be treated by inhibiting DAAO activity. In other embodiments, the presently disclosed subject matter provides a method for treating a cognitive-related disorder in a subject in need of treatment thereof, the method comprising administering to the subject a therapeutically effective amount of a compound of formula (I), either alone or in combination with a therapeutically effective amount of D-serine or D-alanine, or a pharmaceutically effective salt thereof.

B. Compounds of Formula (I)

In some embodiments, the presently disclosed subject matter provides a compound of formula (I):

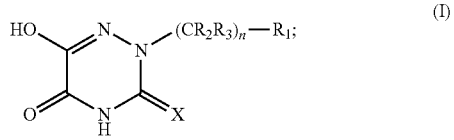

wherein: n is an integer selected from the group consisting of 0, 1, 2, and 3; X is oxygen or sulfur; $R_1$ is selected from the group consisting of H, substituted or unsubstituted straight-chain or branched alkyl, amino, carboxyl, substituted or unsubstituted heteroalkyl, substituted or unsubstituted cycloalkyl, substituted or unsubstituted cycloheteroalkyl, substituted or unsubstituted aryl, and substituted or unsubstituted heteroaryl; and each occurrence of $R_2$ and $R_3$ is independently selected from the group consisting of H, hydroxyl, and halogen, or $R_2$ and $R_3$ together can be oxygen (e.g., the linking group $CR_2R_3$ is —C(=O)—); under the provisos that if n is 0, $R_1$ cannot be methyl or if n is 1, then $R_1$, $R_2$ and $R_3$ cannot each be H; or a pharmaceutically acceptable salt thereof.

In some embodiments of the compound of formula (I), $R_1$ is selected from the group consisting of the following substituent groups, each of which can be substituted or unsubstituted: methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, optionally substituted with alkyl, substituted alkyl, halogen, aryl, substituted aryl, alkoxyl, hydroxyl, nitro, amino, alkylamino, dialkylamino, sulfate, and mercapto, wherein there can be optionally inserted along the alkyl chain one or more oxygen, sulfur or substituted or unsubstituted nitrogen atoms, wherein the nitrogen substituent is hydrogen, lower alkyl, or aryl; cyclopentyl, cyclohexyl, and cycloheptyl, adamantyl, octahydronaphthyl, decalin, camphor, camphane, noradamantyl, dihydro- and tetrahydronaphthalene, cyclopropylmethyl and cyclopentylethyl; pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl; ethenyl, propenyl, butenyl, 1-methyl-2-buten-1-yl, pentenyl, hexenyl, octenyl, and butadienyl; cyclopropenyl, cyclobutenyl, cyclopentenyl, cyclopentadiene, cyclohexenyl, 1,3-cyclohexadiene, cycloheptenyl, cycloheptatrienyl, and cyclooctenyl; ethynyl, 2-propynyl(propargyl), 1-propynyl, pentynyl, hexynyl, and heptynyl; phenyl, phenoxyphenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, indazolyl, 1-isoquinolyl, 5-isoquinolyl, 2-quinoxalinyl, 5-quinoxalinyl, 3-quinolyl, and 6-quinolyl; and amino, carboxyl, hydroxyl, hydroxyalkyl, mercapto, nitro, sulfate, thiol, and ureido.

In particular embodiments of a compound of formula (I), $R_1$ is selected from the group consisting of the following substituent groups, each of which can be substituted or unsubstituted: alkyl, branched alkyl, amino, carboxyl, phenyl, naphthyl, biphenyl, phenoxyphenyl, pyridinyl, pyrrolyl, pyrazolyl, carbazolyl, indazolyl, indolyl, octahydro-1H-indolyl, piperazinyl, thienyl, tetrahydrothienyl, dihydroisoquinolinyl, quinolinyl, isoquinolinyl, 1H-benzo[d]imidazolyl, hexahydro-1H-pyrrolo[2,3-b]pyridinyl, and 1H-pyrrol[2,3-b]pyridinyl.

In yet more particular embodiments of a compound of formula (I), the compound of formula (I) is selected from the group consisting of: 6-hydroxy-2-phenethyl-1,2,4-triazine-3,5(2H,4H)-dione; 2-(4-fluorophenethyl)-6-hydroxy-1,2,4-triazine-3,5(2H,4H)-dione; 2-(3-fluorophenethyl)-6-hydroxy-1,2,4-triazine-3,5(2H,4H)-dione; 2-(2-fluorophenethyl)-6-hydroxy-1,2,4-triazine-3,5(2H,4H)-dione; 2-(4-chlorophenethyl)-6-hydroxy-1,2,4-triazine-3,5(2H,4H)-dione; 2-(3-chlorophenethyl)-6-hydroxy-1,2,4-triazine-3,5(2H,4H)-dione; 2-(2-chlorophenethyl)-6-hydroxy-1,2,4-triazine-3,5(2H,4H)-dione; 6-hydroxy-2-(4-methylphenethyl)-1,2,4-triazine-3,5(2H,4H)-dione; 6-hydroxy-2-(3-methylphenethyl)-1,2,4-triazine-3,5(2H,4H)-dione; 6-hydroxy-2-(2-methylphenethyl)-1,2,4-triazine-3,5(2H,4H)-dione; 6-hydroxy-2-(4-(trifluoromethyl)phenethyl)-1,2,4-triazine-3,5(2H,4H)-dione; 6-hydroxy-2-(3-(trifluoromethyl)phenethyl)-1,2,4-triazine-3,5(2H,4H)-dione; 2-(2,4-dichlorophenethyl)-6-hydroxy-1,2,4-triazine-3,5(2H,4H)-dione; 6-hydroxy-2-(2-(naphthalen-1-yl)ethyl)-1,2,4-triazine-3,5(2H,4H)-dione; 2-(2-(biphenyl-4-yl)ethyl)-6-hydroxy-1,2,4-triazine-3,5(2H,4H)-dione; 6-hydroxy-2-methyl-1,2,4-triazine-3,5(2H,4H)-dione; 6-hydroxy-2-isopentyl-1,2,4-triazine-3,5(2H,4H)-dione; 2-(3,3-dimethylbutyl)-6-hydroxy-1,2,4-triazine-3,5(2H,4H)-dione; 6-hydroxy-2-(3-phenylpropyl)-1,2,4-triazine-3,5(2H,4H)-dione; 2-benzyl-6-hydroxy-1,2,4-triazine-3,5(2H,4H)-dione; 6-hydroxy-2-(naphthalen-1-ylmethyl)-1,2,4-triazine-3,5(2H,4H)-dione; 6-hydroxy-2-(2-methoxyphenethyl)-1,2,4-triazine-3,5(2H,4H)-dione; 6-hydroxy-2-(2-hydroxyphenethyl)-1,2,4-triazine-3,5(2H,4H)-dione; 6-hydroxy-2-(3-methoxyphenethyl)-1,2,4-triazine-3,5(2H,4H)-dione; 6-hydroxy-2-(3-hydroxyphenethyl)-1,2,4-triazine-3,5(2H,4H)-dione; 6-hydroxy-2-(4-methoxyphenethyl)-1,2,4-triazine-3,5(2H,4H)-dione; 6-hydroxy-2-(4-hydroxyphenethyl)-1,2,4-triazine-3,5(2H,4H)-dione; 2-(3,4-dichlorophenethyl)-6-hydroxy-1,2,4-triazine-3,5(2H,4H)-dione; 2-(3-chloro-4-fluorophenethyl)-6-hydroxy-1,2,4-triazine-3,5(2H,4H)-dione; 6-hydroxy-2-(naphthalen-2-ylmethyl)-1,2,4-triazine-3,5(2H,4H)-dione; 2-((6-fluoronaphthalen-2-yl)methyl)-6-hydroxy-1,2,4-triazine-3,5(2H,4H)-dione; 6-hydroxy-2-(4-methoxyphenethyl)-1,2,4-triazine-3,5(2H,4H)-dione; 6-hydroxy-2-(3-phenoxyphenethyl)-1,2,4-triazine-3,5(2H,4H)-dione; 2-(4-(2-fluorophenoxyl)benzyl)-6-hydroxy-1,2,4-triazine-3,5(2H,4H)-dione; 2-(biphenyl-4-ylmethyl)-6-hydroxy-1,2,4-triazine-3,5(2H,4H)-dione; 2-(2,2-Difluoro-2-phenylethyl)-6-hydroxy-1,2,4-triazine-3,5(2H,4H)-dione; 2-(3,4-difluorophenethyl)-6-hydroxy-1,2,4-triazine-3,5(2H,4H)-dione; 2-(2-(1H-pyrrol-1-yl)ethyl)-6-hydroxy-1,2,4-triazine-3,5(2H,4H)-dione; 2-(2-(1H-pyrazol-1-yl)ethyl)-6-hydroxy-1,2,4-triazine-3,5(2H,4H)-dione; 2-(2-(1H-indol-1-yl)ethyl)-6-hydroxy-1,2,4-triazine-3,5(2H,4H)-dione; 2-(2-(1H-benzo[d]imidazol-1-yl)ethyl)-6-hydroxy-1,2,4-triazine-3,5(2H,4H)-dione; 2-(2-(1H-pyrrolo[2,3-b]pyridin-1-yl)ethyl)-6-hydroxy-1,2,4-triazine-3,5(2H,4H)-dione; 2-(2-(1H-indazol-1-yl)ethyl)-6-hydroxy-1,2,4-triazine-3,5(2H,4H)-dione; 2-(2-(9H-carbazol-9-yl)ethyl)-6-hydroxy-1,2,4-triazine-3,5(2H,4H)-dione; 6-hydroxy-2-(2-morpholinoethyl)-1,2,4-triazine-3,5(2H,4H)-dione; 6-hydroxy-2-(1-phenylpropan-2-yl)-1,2,4-triazine-3,5(2H,4H)-dione; 6-hydroxy-2-(2-(pyridin-2-yl)ethyl)-1,2,4-triazine-3,5(2H,4H)-dione; 6-hydroxy-2-(perfluorophenyl)ethyl-1,2,4-triazine-3,5(2H,4H)-dione; 6-hydroxy-2-(((1R,2R)-2-phenylcyclopropyl)methyl)-1,2,4-triazine-3,5(2H,4H)-dione; 2-((1H-indol-4-yl)methyl)-6-hydroxy-1,2,4-triazine-3,5(2H,4H)-dione; 6-hydroxy-2-(isoquinolin-5-ylmethyl)-1,2,4-triazine-3,5(2H,4H)-dione; 2-(benzo[b]thiophen-7-ylmethyl)-6-hydroxy-1,2,4-triazine-3,5(2H,4H)-dione; 2-(3,5-difluorophenethyl)-6-hydroxy-1,2,4-triazine-3,5(2H,4H)-dione; 2-((5-fluoronaphthalen-1-yl)methyl)-6-hydroxy-1,2,4-triazine-3,5(2H,4H)-dione; 2-(4-ethoxyphenethyl)-6-hydroxy-1,2,4-triazine-3,5(2H,4H)-dione; 6-hydroxy-2-((2-methylnaphthalen-1-yl)methyl)-1,2,4-triazine-3,5(2H,4H)-dione; 2-(2-(dimethylamino)ethyl)-6-hydroxy-1,2,4-triazine-3,5(2H,4H)-dione; 6-hydroxy-2-(2-(4-isopropylpiperazin-1-yl)ethyl)-1,2,4-triazine-3,5(2H,4H)-dione; 2-(2-(4-(2-fluorophenyl)piperazin-1-yl)ethyl)-6-hydroxy-1,2,4-triazine-3,5(2H,4H)-dione; 2-(2-(3,4-dihydroisoquinolin-2(1H)-yl)ethyl)-6-hydroxy-1,2,4-triazine-3,5(2H,4H)-dione; 6-hydroxy-2-phenethyl-3-thioxo-3,4-dihydro-1,2,4-triazin-5(2H)-one; 6-hydroxy-2-(2-oxo-2-phenylethyl)-1,2,4-triazine-3,5(2H,4H)-dione; 6-hydroxy-2-(2-hydroxy-2-phenylethyl)-1,2,4-triazine-3,5(2H,4H)-dione; 6-hydroxy-2-(quinolin-8-ylmethyl)-1,2,4-triazine-3,5(2H,4H)-dione; 2-((4-fluoronaphthalen-1-yl)methyl)-6-hydroxy-1,2,4-triazine-3,5(2H,4H)-dione; 6-hydroxy-2-((4-methylnaphthalen-1-yl)methyl)-1,2,4-triazine-3,5(2H,4H)-dione; 2-((6-bromonaphthalen-1-yl)methyl)-6-hydroxy-1,2,4-triazine-3,5(2H,4H)-dione; 2-(2-(2'-fluorobiphenyl-4-yl)ethyl)-6-hydroxy-1,2,4-triazine-3,5(2H,4H)-dione; and 6-hydroxy-2-(4-morpholinophenethyl)-1,2,4-triazine-3,5(2H,4H)-dione.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{2S}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R'', —OR', —SR, and/or —SO$_2$R'. Where "heteroalkyl" is recited, followed by recitations of specific heteroalkyl groups, such as —NR'R or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl(propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$CH_2CH_2CH_2CH_2$—, —$CH_2$CH=CH$CH_2$—, —$CH_2$CsCC$H_2$—, —$CH_2CH_2$CH($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O) OR'— and —R'OC(O)—. The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, indazolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below.

The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like). The term "haloaryl," however, as used herein, is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

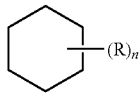

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

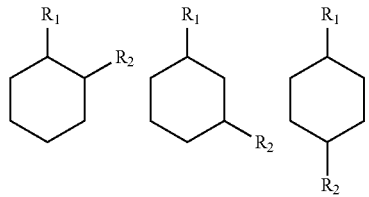

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure. The symbol ( ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR'''—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R" wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as pharmaceutically acceptable salts. The term "pharmaceutically acceptable salts" is meant to include salts of active compounds which are prepared with relatively nontoxic acids or bases, depending on the particular substituent moieties found on the compounds described herein. Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrates, (e.g. (+)-tartrates, (−)-tartrates or mixtures thereof including racemic mixtures), or teoclate. These salts may be prepared by methods known to those skilled in art. Other pharmaceutically acceptable salts may be found in, for example, Remington: The Science and Practice of Pharmacy (20$^{th}$ ed.) Lippincott, Williams & Wilkins (2000).

Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like.

Also included are salts of amino acids such as arginate and the like, and salts of organic acids like glucuronic or galactunoric acids and the like, see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

C. Compositions Comprising Compounds of Formula (I) and D-Serine or D-Alanine

The presently disclosed subject matter, in some embodiments, provides a pharmaceutical composition including a therapeutically effective amount of one or more of the presently disclosed compounds of formula (I) alone or in combination with one or more additional therapeutic agents in admixture with a pharmaceutically acceptable carrier. One of skill in the art will recognize that the pharmaceutical compositions include the pharmaceutically acceptable salts of the compounds described above. In particular embodiments, the composition comprises a therapeutically effective combination of D-serine or D-alanine and a compound of formula (I).

Pharmaceutical compositions suitable for use in the present disclosure include compositions wherein the active ingredients are contained in a therapeutically effective amount to achieve its intended purpose. Determination of the therapeutically effective amounts is well within the capability of those skilled in the art, especially in light of the detailed disclosure provided herein. In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the diagnosis or progression of a particular disease state or condition, and the like.

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Further, dragee cores comprising the presently disclosed compositions can be provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

In therapeutic applications, the compounds of the disclosure can be formulated for a variety of modes of administration, including systemic and topical or localized administration. Techniques and formulations generally may be found in Remington: The Science and Practice of Pharmacy (20th ed.) Lippincott, Williams & Wilkins (2000).

Depending on the specific conditions being treated, the presently disclosed compositions may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20th ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

D. Methods of Treatment

The presently disclosed subject matter provides methods of use of the compounds of formula (I) in a subject. In some embodiments, the method is a method for inhibiting the activity of DAAO in a subject, the method comprising administering to a subject at least one compound of formula (I) in an amount effective to inhibit the activity of DAAO in the subject. It has been shown that DAAO and the D-amino acids that this enzyme regulates have been implicated in a wide variety of physiological processes. Therefore, these methods may affect physiological processes such as arterial pressure, hormone release, neurotransmission, and any physiological process that is affected by the inhibition of DAAO.

In other embodiments, the method is a method for increasing the levels of D-serine in a subject, the method comprising administering to a subject at least one compound of formula (I) in an amount effective to increase the levels of D-serine in the subject. The presently disclosed subject matter provides compounds that inhibit the activity of DAAO in a subject. Since D-serine is a substrate of DAAO, inhibition of DAAO results in increased levels of D-serine in the subject. D-serine is found in brain tissue at high levels and in peripheral tissues and blood at low or trace levels. In the nervous system, D-serine acts as an agonist for the NMDA receptor. As such, D-serine plays a role in human physiology, such as central nervous system development, memory, learning, and the like, and pathology, such as ALS, Alzheimer's disease, epilepsy, schizophrenia, bipolar disorder, and the like. Therefore, the levels of D-serine may be increased in a subject to affect different processes in the subject.

In still other embodiments, the presently disclosed subject matter provides a method for suppressing the levels of hydrogen peroxide generation in a subject, the method comprising administering to a subject at least one compound of formula (I) in an amount effective to suppress the levels of hydrogen peroxide in the subject.

In particular embodiments, the presently disclosed subject matter provides therapeutic agents for treating cognitive-related disorders, post-traumatic stress disorder (PTSD), and disorders involving pain. Accordingly, in some embodiments, the presently disclosed subject matter provides D-amino acid oxidase (DAAO) inhibitors of formula (I) that can be used alone or in combination with D-serine or D-alanine to treat patients with cognitive-related disorders (such as schizophrenia), PTSD, and disorders involving pain.

For example, D-Serine, which has been reported to improve neuropsychiatric symptoms in patients with schizophrenia, is substantially metabolized by DAAO in the liver and kidneys. Further, DAAO-mediated metabolism of D-serine in the kidneys was reported to cause nephrotoxicity due to the action of hydrogen peroxide, a by-product of the enzymatic process. Accordingly, without wishing to be bound to any one particular theory, blocking or inhibiting DAAO-mediated D-serine metabolism could substantially increase the bioavailability of D-serine while preventing hydrogen peroxide-induced peripheral toxicity. This dual improvement to D-serine therapy could provide tremendous benefits to patients with schizophrenia, particularly those suffering from negative symptoms and cognitive deficits, and patients suffering from PTSD and/or afflicted with a disorder involving pain.

i. Method for Treating a Disorder by Inhibiting DAAO Activity

Accordingly, in some embodiments, the presently disclosed subject matter provides a method for treating a disorder or a condition that can be treated by inhibiting D-amino acid oxidase (DAAO) activity in a subject in need of treatment thereof, the method comprising administering to the subject a therapeutically effective amount of a compound of formula (I), either alone or in combination with a therapeutically effective amount of D-serine or D-alanine:

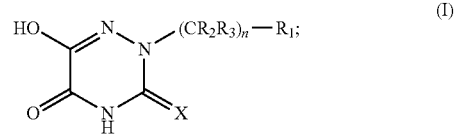

wherein: n is an integer selected from the group consisting of 0, 1, 2, and 3; X is oxygen or sulfur; $R_1$ is selected from the group consisting of H, substituted or unsubstituted straight-chain or branched alkyl, amino, carboxyl, substituted or unsubstituted heteroalkyl, substituted or unsubstituted cycloalkyl, substituted or unsubstituted cycloheteroalkyl, substituted or unsubstituted aryl, and substituted or unsubstituted heteroaryl; and each occurrence of $R_2$ and $R_3$ is independently selected from the group consisting of H, hydroxyl, and halogen, or $R_2$ and $R_3$ together can be oxygen (e.g., the linking group $CR_2R_3$ is —C(=O)—); under the provisos that if n is 0, $R_1$ cannot be methyl or if n is 1, then $R_1$, $R_2$ and $R_3$ cannot each be H; or a pharmaceutically acceptable salt thereof. In particular embodiments, the compound of formula (I) is as disclosed in Table 1, herein below.

An "effective amount" of an active agent refers to the amount of the active agent sufficient to elicit a desired biological response. As will be appreciated by one of ordinary skill in the art, the absolute amount of a particular agent that is effective can vary depending on such factors as the desired biological endpoint, the agent to be delivered, the therapeutic effect desired, and the like. One of ordinary skill in the art will further understand that an effective amount can be administered in a single dose, or can be achieved by administration of multiple doses.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

ii. Method for Treating a Cognitive-Related Disorder by Co-Administering D-Serine or D-Alanine and a DAAO Inhibitor In some embodiments, the presently disclosed subject matter provides a method for treating a cognitive-related disorder in a subject in need of treatment thereof, the method comprising administering to the subject a therapeutically effective amount of a compound of formula (I), either alone or in combination with a therapeutically effective amount of D-serine or D-alanine:

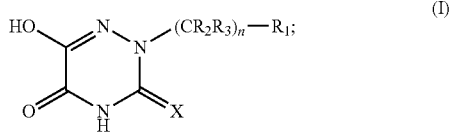

wherein: n is an integer selected from the group consisting of 0, 1, 2, and 3; X is oxygen or sulfur; $R_1$ is selected from the group consisting of H, substituted or unsubstituted straight-chain or branched alkyl, amino, carboxyl, substituted or unsubstituted heteroalkyl, substituted or unsubstituted cycloalkyl, substituted or unsubstituted cycloheteroalkyl, substituted or unsubstituted aryl, and substituted or unsubstituted heteroaryl; and each occurrence of $R_2$ and $R_3$ is independently selected from the group consisting of H, hydroxyl, and halogen, or $R_2$ and $R_3$ together can be oxygen (e.g., the linking group $CR_2R_3$ is —C(=O)—); under the provisos that if n is 0, $R_1$ cannot be methyl or if n is 1, then $R_1$, $R_2$ and $R_3$ cannot each be H; or a pharmaceutically acceptable salt thereof. In particular embodiments, the compound of formula (I) is as disclosed in Table 1, herein below.

The cognitive-related disorder treated by the presently disclosed methods can include schizophrenia and related disorders, psychosis, bipolar disorder, psychotic episodes of anxiety, anxiety associated with psychosis, psychotic mood disorders, severe major depressive disorder, mood disorders associated with psychotic disorders, acute mania, depression associated with bipolar disorder, mood disorders associated with schizophrenia, dementia, including age-related dementia and senile dementia of the Alzheimer's type, memory disorders, neuropathic pain, and any combination thereof.

By administering in combination with, and grammatical derivations thereof, is meant that a presently disclosed DAAO inhibitor and D-serine or D-alanine are administered in combination, which, in certain embodiments, can include either simultaneously, sequentially, or a combination thereof. Therefore, co-administering D-serine or D-alanine and a DAAO inhibitor to a subject can include administering D-serine or D-alanine and a DAAO inhibitor at the same time (i.e., simultaneously) or at different times (i.e., sequentially, in either order, on the same day or on different days or at different time intervals), so long as the effect of the combination of both agents is achieved in the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the D-serine or D-alanine and a DAAO inhibitor are administered simultaneously, they can be administered to the subject as separate pharmaceutical compositions, each comprising either D-serine or D-alanine or a DAAO inhibitor, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

Without wishing to be bound to any one particular theory, the DAAO inhibitor, when co-administered with D-serine or D-alanine, should prevent exogenous D-serine from being metabolized by DAAO in the kidneys, thereby resulting in a reduction of nephrotoxicity and an increase in plasma levels of D-serine. Since D-serine crosses the blood-brain barrier rapidly, the increased levels of D-serine in plasma also should lead to an increase in brain D-serine levels. This approach is analogous to the clinically proven carbidopa/levodopa combination (Sinemet). Boomsma F., et al., "Treatment of idiopathic parkinsonism with L-dopa in the absence and presence of decarboxylase inhibitors: effects on plasma levels of L-dopa, dopa decarboxylase, catecholamines and 3-O-methyl-dopa," *J. Neural.* 236(4):223-30 (1989). Namely, carbidopa, a DOPA decarboxylase inhibitor, blocks peripheral degradation of levodopa and increases the concentration of levodopa in the brain. One interesting contrast between the approach provided by Boomsma et al. and the presently disclosed approach, however, is that while levodopa is converted in the brain into an active pharmaceutical species, i.e., dopamine, D-serine remains intact in the region of the brain where it acts on the NMDA receptors owing to the lack of the DAAO activity in the forebrain. Horiike K., et al., "D-amino-acid oxidase is confined to the lower brain stem and cerebellum in rat brain: regional differentiation of astrocytes," *Brain Res.* 652(2): 297-303 (1994). The presently disclosed subject matter demonstrates that the co-administration approach is more effective at increasing plasma levels and brain levels of D-serine than DAAO inhibition alone.

iii. Method for Treating Post-Traumatic Stress Disorder

In yet other embodiments, blocking or inhibiting DAAO-mediated D-serine metabolism can be used to treat, reduce, or prevent PTSD symptoms.

Accordingly, in some embodiments, the presently disclosed subject matter provides a method for treating post-traumatic stress disorder in a subject in need of treatment thereof, the method comprising administering to the subject a therapeutically effective amount of a compound of formula (I), either alone or in combination with a therapeutically effective amount of D-serine or D-alanine, to inhibit D-amino acid oxidase (DAAO) activity in the subject:

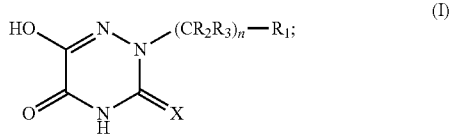

wherein: n is an integer selected from the group consisting of 0, 1, 2, and 3; X is oxygen or sulfur; $R_1$ is selected from the group consisting of H, substituted or unsubstituted straight-chain or branched alkyl, amino, carboxyl, substituted or unsubstituted heteroalkyl, substituted or unsubstituted cycloalkyl, substituted or unsubstituted cycloheteroalkyl, substituted or unsubstituted aryl, and substituted or unsubstituted heteroaryl; and each occurrence of $R_2$ and $R_3$ is independently selected from the group consisting of H, hydroxyl, and halogen, or $R_2$ and $R_3$ together can be oxygen (e.g., the linking group $CR_2R_3$ is —C(=O)—); under the provisos that if n is 0, $R_1$ cannot be methyl or if n is 1, then $R_1$, $R_2$ and $R_3$ cannot each be H; or a pharmaceutically acceptable salt thereof. In particular embodiments, the compound of formula (I) is as disclosed in Table 1, herein below.

Behavioral manifestations common to PTSD include fear, anxiety, depression, and dissociation and perceptual alterations. Brain regions implicated in the mediation of fear and anxiety are characterized by high NMDA-type glutamate receptor levels (McDonald, A. J., 1996. Glutamate and aspartate immunoreactive neurons of the rat basolateral amygdale: colocalization of excitatory amino acids and projections to the limbic circuit. *Journal of Comparative Neurology* 365, 367-379). It has been shown that the administration of D-serine to patients with chronic PTSD results in a decrease of PTSD symptoms (Heresco-Levy U, Vass A, Boaz B, Wolosker H, Dumin E, Balan L, Deutsch L, and Kremer I, 2009. *International Journal of Neuropsychopharmacology,* 12. 1275-1282).

The methods provided herein may result in treating, reducing, or preventing one symptom associated with PTSD or multiple symptoms. Behavioral manifestations common to PTSD vary by subject and may affect each subject in a different manner.

iv. Method for Treating Pain

In further embodiments, blocking or inhibiting DAAO-mediated D-serine metabolism can be used to treat, reduce, or prevent pain. Reactive oxygen species are chemically reactive molecules that contain oxygen and are highly reactive due to the presence of unpaired valence electrons. Increased reactive oxygen species can cause cell damage ranging from cytoplasmic swelling to death.

DAAO catalyses the oxidative deamination of D-amino acids to α-keto acids and the byproduct hydrogen peroxide, a stable reactive oxygen species that has been strongly implicated in the pathogenesis of pain, such as inflammatory and neuropathic pain. It has been shown that DAAO inhibitors produce analgesia by blocking spinal hydrogen peroxide production (Lu J-M, Gong N, Wang Y-C, and Wang Y-X, 2012. D-Amino acid oxidase-mediated increase in spinal hydrogen peroxide is mainly responsible for formalin-induced tonic pain. *British J of Pharmacology* 165:1941-1955).

It also has been shown that activation of NMDA receptors is involved in central sensitization and mediates chronic pain (Cook A J, Woolf C J, Wall P D, McMahon S B, 1987. Dynamic receptive field plasticity in rat spinal cord dorsal horn following C-primary afferent input. *Nature* 325:151-153; Ying B, Lu N, Zhang Y Q, and Zhao Z Q, 2006. Involvement of spinal glia in tetanically sciatic stimulation-induced bilateral mechanical allodynia in rats. *Biochem Biophys Res Commun* 340: 1264-1272).

Accordingly, in some embodiments, the presently disclosed subject matter provides a method for pain in a subject in need of treatment thereof, the method comprising administering to the subject a compound of formula (I) in an amount effective to inhibit D-amino acid oxidase (DAAO) activity in the subject:

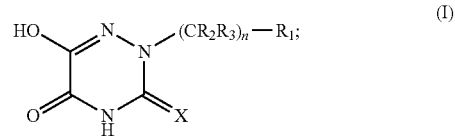

wherein: n is an integer selected from the group consisting of 0, 1, 2, and 3; X is oxygen or sulfur; $R_1$ is selected from the group consisting of H, substituted or unsubstituted straight-chain or branched alkyl, amino, carboxyl, substituted or unsubstituted heteroalkyl, substituted or unsubstituted cycloalkyl, substituted or unsubstituted cycloheteroalkyl, substituted or unsubstituted aryl, and substituted or unsubstituted heteroaryl; and each occurrence of $R_2$ and $R_3$ is independently selected from the group consisting of H, hydroxyl, and halogen, or $R_2$ and $R_3$ together can be oxygen (e.g., the linking group $CR_2R_3$ is —C(=O)—); under the provisos that if n is 0, $R_1$ cannot be methyl or if n is 1, then $R_1$, $R_2$ and $R_3$ cannot each be H; or a pharmaceutically acceptable salt thereof. In particular embodiments, the compound of formula (I) is as disclosed in Table 1, herein below. In some embodiments, the pain comprises inflammatory and/or neuropathic pain.

The pain targeted by a compound of formula (I) may be a chronic pain, such as bone cancer pain or chronic neuropathic pain, or it may be an acute pain, such as a thermal-induced pain. The compounds of the presently disclosed subject matter may be given in advance of expected pain as a prophylactic method or may be administered after a subject feels pain as a therapeutic method.

II. GENERAL DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis of 6-Hydroxy-2-phenethyl-1,2,4-triazine-3,5(2H,4H)-dione

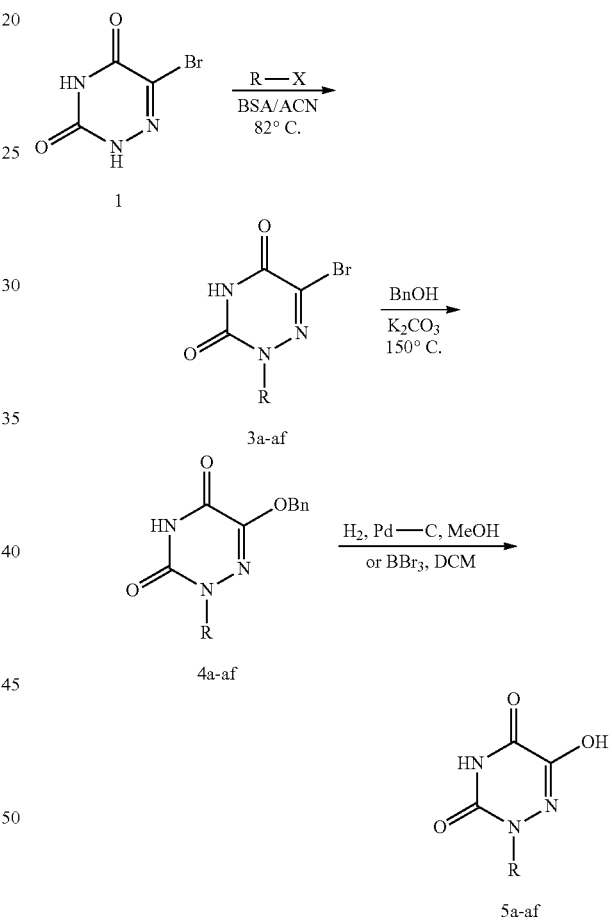

6-Bromo-2-phenethyl-1,2,4-triazine-3,5(2H,4H)-dione (3a)

To a solution of 5-bromo-6-azauracil (1, 1.0 g, 5.21 mmol, 1.0 equiv) in acetonitrile (15 mL) was added N,O-bis(trimethylsilyl)acetamide (13.0 mmol, 3.20 mL, 2.5 equiv). The mixture was heated at 82° C. for 3 h after which phenethyl iodide (2a, 1.13 mL, 7.81 mmol, 1.5 equiv) was added via syringe. The reaction was heated for one day at same temperature. More phenethyl iodide was added on day 2 and day 3 (for a total of 2.5 equiv) as the reaction was not completed. Heating continued for two additional days and the reaction was concentrated in vacuo. The resulting residue was dissolved in dichloromethane and the organic solution was washed twice with water, dried over $Na_2SO_4$ and concentrated to give a solid which was triturated in cold diethyl ether and filtered to give 1.0 g (64%) of the desired product as a tan solid. $^1H$ NMR (DMSO-$d_6$): δ 2.94 (t, J=7.5 Hz, 2H), 4.04 (t, J=7.6 Hz, 2H), 7.22 (m, 3H), 7.28 (m, 2H), 12.53 (s, 1H).

6-(Benzyloxy)-2-phenethyl-1,2,4-triazine-3,5(2H, 4H)-dione (4a)

A mixture of 6-bromo-2-phenethyl-1,2,4-triazine 3a (0.96 g, 3.24 mmol), $K_2CO_3$ (6.49 mmol, 0.90 g, 2.0 equiv) and benzyl alcohol (1.2 mL) was heated overnight at 150° C. Aqueous 10% $KHSO_4$ solution was added and the compound was extracted with EtOAc. The organic layer was dried over $Na_2SO_4$, filtered and concentrated to give a solid which was triturated in EtOAc-hexanes to give 0.773 g (74%) of 6-Benzyloxy triazine 4a as a beige solid. $^1H$ NMR (DMSO-$d_6$): δ 2.91 (t, J=7.2 Hz, 2H), 5.05 (s, 2H), 3.96 (t, J=7.2 Hz, 2H), 7.15 (m, 2H), 7.20 (m, 1H), 7.26-7.31 (m, 2H), 7.36-7.43 (m, 5H), 12.13 (s, 1H).

6-Hydroxy-2-phenethyl-1,2,4-triazine-3,5(2H,4H)-dione (5a)

Compound 4a (0.735 g, 2.27 mmol) was dissolved in a mixture of methanol (5 mL) and acetic acid (8 mL). One spatula tip of 10% Pd/C was added and the mixture was hydrogenated at 50 psi for 1.5 h. The reaction was filtered through celite and the filtrate was concentrated to give a solid which was triturated in EtOAc-hexanes to give 0.316 g (60%) of the desired product 5a as a light pink powder. Mp 199-201° C.; $^1H$ NMR (DMSO-$d_6$): δ 2.90 (t, J=7.8 Hz, 2H), 3.87 (t, J=7.6 Hz, 2H), 7.20 (m, 3H), 7.29 (m, 2H), 11.71 (s, 1H), 12.03 (s, 1H); $^{13}C$ NMR (DMSO-$d_6$): δ 33.6, 50.0, 126.4, 128.5, 128.7, 138.2, 147.8, 148.3, 153.6.

Example 2

Synthesis of 2-(4-fluorophenethyl)-6-hydroxy-1,2,4-triazine-3,5(2H,4H)-dione

6-Bromo-2-(4-fluorophenethyl)-1,2,4-triazine-3,5 (2H,4H)-dione (3b)

Compound 3b was prepared as described for the preparation of 3a with the exception that 2.0 equiv of 1-fluoro-4-(2-iodoethyl)benzene were used in one portion in place of sequential addition of 2.5 equivalents of phenethyl iodide. Yield: 42% (yellow solid). $^1H$ NMR (DMSO-$d_6$): δ 2.93 (t, J=7.1 Hz, 2H), 4.03 (t, J=7.3 Hz, 2H), 7.11 (m, 2H), 7.26 (m, 2H), 12.52 (s, 1H).

6-(Benzyloxy)-2-(4-fluorophenethyl)-1,2,4-triazine-3,5(2H,4H)-dione (4b)

Compound 4b was prepared as described for the preparation of 4a with the exception that the product was purified by Biotage Isolera One using EtOAc/hexanes. Yield: 81% (white solid). $^1H$ NMR (DMSO-$d_6$): δ 2.90 (t, J=6.8 Hz, 2H), 3.95 (t, J=6.9 Hz, 2H), 5.07 (s, 2H), 7.09 (m, 2H), 7.17 (m, 2H), 7.36-7.43 (m, 5H), 12.12 (s, 1H).

2-(4-Fluorophenethyl)-6-hydroxy-1,2,4-triazine-3,5 (2H,4H)-dione (5b)

Compound 5b was prepared as described for the preparation of 5a with the exception that only methanol was used as solvent and the hydrogenation was performed under a hydrogen-filled balloon for 3 h. Yield: 73% (light pink powder). Mp 192-194° C.; $^1H$ NMR (DMSO-$d_6$): δ 2.89 (t, J=7.3 Hz, 2H), 3.87 (t, J=7.3 Hz, 2H), 7.10 (m, 2H), 7.22 (m, 2H), 11.72 (bs, 1H), 11.97 (bs, 1H); Anal. Calcd. for $C_{11}H_{10}N_3O_3F$, 0.65 MeOH: C, 51.44; H, 4.67; N, 15.45. Found: C, 51.28; H, 4.40; N, 15.66.

Example 3

Synthesis of 2-(3-fluorophenethyl)-6-hydroxy-1,2,4-triazine-3,5(2H,4H)-dione

6-Bromo-2-(3-fluorophenethyl)-1,2,4-triazine-3,5 (2H,4H)-dione (3c)

Compound 3c was prepared as described for the preparation of 3a with the exception that 2.0 equiv of 3-fluoro-4-(2-iodoethyl)benzene were used in one portion in place of sequential addition of 2.5 equivalents of phenethyl iodide. Yield: 66% (yellow solid). $^1H$ NMR (DMSO-$d_6$): δ 2.96 (t, J=7.3 Hz, 2H), 4.06 (t, J=7.3 Hz, 2H), 7.05 (m, 2H), 7.22 (m, 1H), 7.33 (m, 1H), 12.53 (s, 1H).

6-(Benzyloxy)-2-(3-fluorophenethyl)-1,2,4-triazine-3,5(2H,4H)-dione (4c)

Compound 4c was prepared as described for the preparation of 4a. Yield: 78% (light tan solid). $^1H$ NMR (DMSO-$d_6$): δ 2.94 (t, J=6.8 Hz, 2H), 3.98 (t, J=6.9 Hz, 2H), 5.06 (s, 2H), 6.96-7.05 (m, 3H), 7.29 (m, 1H), 7.36-7.43 (m, 5H), 12.13 (s, 1H).

2-(3-Fluorophenethyl)-6-hydroxy-1,2,4-triazine-3,5 (2H,4H)-dione (5c)

Compound 5c was prepared as described for the preparation of 5a with the exception that methanol and ethyl acetate were used as co-solvents and the hydrogenation was performed overnight at 30 psi. Yield: 79% (white solid). Mp 196-198° C.; $^1H$ NMR (DMSO-$d_6$): δ 2.93 (t, J=7.3 Hz, 2H), 3.89 (t, J=7.2 Hz, 2H), 7.03 (m, 3H), 7.31 (m, 1H), 11.89 (bs, 2H);

Example 4

Synthesis of 2-(2-fluorophenethyl)-6-hydroxy-1,2,4-triazine-3,5(2H,4H)-dione

6-Bromo-2-(2-fluorophenethyl)-1,2,4-triazine-3,5 (2H,4H)-dione (3d)

Compound 3d was prepared as described for the preparation of 3a with the exception that 2.0 equiv of 2-fluoro-4-(2-iodoethyl)benzene were used in one portion in place of sequential addition of 2.5 equivalents of phenethyl iodide. Yield: 34% (yellow solid). $^1H$ NMR (DMSO-$d_6$): δ 2.98 (t, J=7.2 Hz, 2H), 4.05 (t, J=7.2 Hz, 2H), 7.15 (m, 2H), 7.29 (m, 2H), 12.55 (s, 1H).

6-(Benzyloxy)-2-(2-fluorophenethyl)-1,2,4-triazine-3,5(2H,4H)-dione (4d)

Compound 4d was prepared as described for the preparation of 4a with the exception that the reaction was heated over weekend. Yield: 65% (white powder). $^1$H NMR (DMSO-$d_6$): δ 2.96 (t, J=6.8 Hz, 2H), 3.97 (t, J=6.6 Hz, 2H), 4.95 (s, 2H), 7.11 (m, 2H), 7.17 (m, 1H), 7.24 (m, 1H), 7.36-7.41 (m, 5H), 12.17 (s, 1H).

2-(2-Fluorophenethyl)-6-hydroxy-1,2,4-triazine-3,5 (2H,4H)-dione (5d)

Compound 5d was prepared as described for the preparation of 5a with the exception that methanol and ethyl acetate were used as co-solvents and the hydrogenation was performed at 30 psi for 1.5 h. Yield: 83% (white solid). Mp 193-195° C.; $^1$H NMR (DMSO-$d_6$): δ 2.95 (t, J=7.2 Hz, 2H), 3.88 (t, J=7.2 Hz, 2H), 7.12 (m, 2H), 7.26 (m, 2H), 11.68 (bs, 1H), 11.99 (bs, 1H).

Example 5

Synthesis of 2-(4-chlorophenethyl)-6-hydroxy-1,2,4-triazine-3,5(2H,4H)-dione

6-Bromo-2-(4-chlorophenethyl)-1,2,4-triazine-3,5 (2H,4H)-dione (3e)

Compound 3e was prepared as described for the preparation of 3a with the exception 1-chloro-4-(2-iodoethyl) benzene was used in place of phenethyl iodide. Yield: 42% (yellow solid). $^1$H NMR (DMSO-$d_6$): δ 2.94 (t, J=7.3 Hz, 2H), 4.03 (t, J=7.3 Hz, 2H), 7.25 (d, J=8.3 Hz, 2H), 7.34 (d, J=8.3 Hz, 2H), 12.52 (s, 1H).

6-(Benzyloxy)-2-(4-chlorophenethyl)-1,2,4-triazine-3,5(2H,4H)-dione (4e)

Compound 4e was prepared as described for the preparation of 4a with the exception that the reaction was heated over weekend. The product was purified by Biotage Isolera One using EtOAc/hexanes. Yield: 72% (white solid). $^1$H NMR (DMSO-$d_6$): δ 2.90 (t, J=6.7 Hz, 2H), 3.96 (t, J=6.9 Hz, 2H), 5.05 (s, 2H), 7.15 (d, J=8.3 Hz, 2H), 7.31 (d, J=8.3 Hz, 2H), 7.36-7.43 (m, 5H), 12.12 (s, 1H).

2-(4-Chlorophenethyl)-6-hydroxy-1,2,4-triazine-3,5 (2H,4H)-dione (5e)

To a solution of compound 4e (0.074 g, 0.207 mmol) in dichloromethane (3 mL) at 0° C. was slowly added a 1.0 M solution of BBr$_3$ (0.201 mL, 0.207 mmol, 1 equiv). The reaction was stirred at 0° C. for 40 min and another equivalent of BBr$_3$ was added. Stirring continued at 0° C. for 30 min and the reaction was allowed to warm up to rt and stirred until completion of the reaction (total time: 2 h). Water was slowly added. The compound was extracted with EtOAc. The organic layer was washed with brine, dried over Na$_2$SO$_4$ and concentrated to a solid residue which was triturated in cold diethyl ether-hexanes. Further sequential recrystallization of the solid in EtOAc-hexanes gave 29 mg (52%) of the desired compound 5e as a white solid. Mp 225-226° C.; $^1$H NMR (DMSO-$d_6$): δ 2.90 (t, J=7.2 Hz, 2H), 3.87 (t, J=7.3 Hz, 2H), 7.20 (d, J=8.3 Hz, 2H), 7.33 (d, J=8.3 Hz, 2H), 11.69 (s, 1H), 12.03 (s, 1H); Anal. Calcd. for C$_{11}$H$_{10}$N$_3$Cl$_1$O$_3$ (0.9 MeOH, 0.35H$_2$O): C, 47.20; H, 4.76; N, 13.88; Cl, 11.71. Found: C, 47.49; H, 4.65; N, 13.90; Cl, 11.36.

Example 6

Synthesis of 2-(3-chlorophenethyl)-6-hydroxy-1,2,4-triazine-3,5(2H,4H)-dione

6-Bromo-2-(3-chlorophenethyl)-1,2,4-triazine-3,5 (2H,4H)-dione (3f)

Compound 3f was prepared as described for the preparation of 3a with the exception that 2.0 equiv of 3-chloro-4-(2-iodoethyl)benzene were used in one portion in place of sequential addition of 2.5 equivalents of phenethyl iodide. Yield: 73% (tan solid). $^1$H NMR (DMSO-$d_6$): δ 2.95 (t, J=7.2 Hz, 2H), 4.06 (t, J=7.3 Hz, 2H), 7.18 (m, 1H), 7.27-7.34 (m, 3H), 12.53 (s, 1H).

6-(Benzyloxy)-2-(3-chlorophenethyl)-1,2,4-triazine-3,5(2H,4H)-dione (4f)

Compound 4f was prepared as described for the preparation of 4a. Yield: 70% (beige powder). $^1$H NMR (DMSO-$d_6$): δ 2.93 (t, J=6.9 Hz, 2H), 3.98 (t, J=6.9 Hz, 2H), 5.05 (s, 2H), 7.09 (m, 1H), 7.25-7.31 (m, 3H), 7.36-7.43 (m, 5H), 12.13 (s, 1H).

2-(3-Chlorophenethyl)-6-hydroxy-1,2,4-triazine-3,5 (2H,4H)-dione (5f)

Compound 5f was prepared as described for the preparation of 5e with the exception that 2 equiv of boron tribromide were added at rt in one portion and that the reaction was stirred at rt for 1.5 h. Yield: 54% (beige powder). Mp 218-220° C.; $^1$H NMR (DMSO-$d_6$): δ 2.92 (t, J=7.1 Hz, 2H), 3.90 (t, J=7.2 Hz, 2H), 7.14 (m, 1H), 7.26-7.33 (m, 3H), 11.69 (s, 1H), 12.04 (s, 1H).

Example 7

Synthesis of 2-(2-chlorophenethyl)-6-hydroxy-1,2,4-triazine-3,5(2H,4H)-dione

6-Bromo-2-(2-chlorophenethyl)-1,2,4-triazine-3,5 (2H,4H)-dione (3g)

Compound 3g was prepared as described for the preparation of 3a with the exception that 2.0 equiv of 3-chloro-4-(2-iodoethyl)benzene were used in one portion in place of sequential addition of 2.5 equivalents of phenethyl iodide. Yield: 28% (yellow solid). $^1$H NMR (DMSO-$d_6$): δ 3.07 (t, J=7.1 Hz, 2H), 4.07 (t, J=7.1 Hz, 2H), 7.26-7.29 (m, 2H), 7.34 (m, 1H), 7.41 (m, 1H), 12.54 (s, 1H).

6-(Benzyloxy)-2-(2-chlorophenethyl)-1,2,4-triazine-3,5(2H,4H)-dione (4g)

Compound 4g was prepared as described for the preparation of 4a with the exception that the product was purified by Biotage Isolera One using EtOAc/hexanes. Yield: 85% (white solid). $^1$H NMR (DMSO-$d_6$): δ 3.05 (t, J=6.7 Hz, 2H), 4.00 (t, J=6.7 Hz, 2H), 4.92 (s, 2H), 7.22-7.27 (m, 4H), 7.34-7.43 (m, 5H), 12.15 (s, 1H).

2-(2-Chlorophenethyl)-6-hydroxy-1,2,4-triazine-3,5 (2H,4H)-dione (5g)

Compound 5g was prepared as described for the preparation of 5e with the exception that 2 equiv of boron tribromide were added at rt in one portion and that the reaction was stirred at rt for 1.5 h. Yield: 39% (white powder). Mp 210-212° C.; $^1$H NMR (DMSO-$d_6$): δ 3.04 (t, J=7.1 Hz, 2H), 3.91 (t, J=7.1 Hz, 2H), 7.24-7.29 (m, 3H), 7.41 (m, 1H), 11.66 (s, 1H), 12.04 (s, 1H).

Example 8

Synthesis of 6-Hydroxy-2-(4-methylphenethyl)-1,2,4-triazine-3,5(2H,4H)-dione

6-Bromo-2-(4-methylphenethyl)-1,2,4-triazine-3,5(2H,4H)-dione (3h)

Compound 3h was prepared as described for the preparation of 3a with the exception that 2.0 equiv of 4-methyl-4-(2-iodoethyl)benzene were used in one portion in place of sequential addition of 2.5 equivalents of phenethyl iodide. Yield: 63% (tan solid). $^1$H NMR (DMSO-$d_6$): δ 2.26 (s, 3H), 2.89 (t, J=7.5 Hz, 2H), 4.00 (m, 2H), 7.10 (s, 4H), 12.52 (s, 1H).

6-(Benzyloxy)-2-(4-methylphenethyl)-1,2,4-triazine-3,5(2H,4H)-dione (4h)

Compound 4h was prepared as described for the preparation of 4a with the exception that the product was purified by Biotage Isolera One using EtOAc/hexanes. Yield: 72% (white foam). $^1$H NMR (DMSO-$d_6$): δ 2.24 (s, 3H), 2.86 (t, J=7.2 Hz, 2H), 3.93 (t, J=7.1 Hz, 2H), 5.06 (s, 2H), 7.03 (m, 2H), 7.06 (m, 2H), 7.36-7.43 (m, 5H), 12.12 (s, 1H).

6-Hydroxy-2-(4-methylphenethyl)-1,2,4-triazine-3,5(2H,4H)-dione (5h)

Compound 5h was prepared as described for the preparation of 5a with the exception that only methanol was used as solvent and the hydrogenation was performed at 30 psi for 2 h. Yield: 54% (white solid). Mp 219-220° C.; $^1$H NMR (DMSO-$d_6$): δ 2.25 (s, 3H), 2.85 (t, J=7.5 Hz, 2H), 3.84 (t, J=7.6 Hz, 2H), 7.08 (q, J=8.1, 11.4 Hz, 4H), 11.68 (s, 1H), 12.02 (s, 1H).

Example 9

Synthesis of 6-Hydroxy-2-(3-methylphenethyl)-1,2,4-triazine-3,5(2H,4H)-dione

6-Bromo-2-(3-methylphenethyl)-1,2,4-triazine-3,5(2H,4H)-dione (3i)

Compound 3i was prepared as described for the preparation of 3a with the exception that 2.0 equiv of 3-methyl-4-(2-iodoethyl)benzene were used in one portion in place of sequential addition of 2.5 equivalents of phenethyl iodide. Yield: 66% (tan solid). $^1$H NMR (DMSO-$d_6$): δ 2.27 (s, 3H), 2.89 (t, J=7.6 Hz, 2H), 4.01 (t, J=7.6 Hz, 2H), 7.02 (m, 3H), 7.18 (t, J=7.3 Hz, 1H), 12.50 (s, 1H).

6-(Benzyloxy)-2-(3-methylphenethyl)-1,2,4-triazine-3,5(2H,4H)-dione (4i)

Compound 4i was prepared as described for the preparation of 4a. Yield: 62% (yellow powder). $^1$H NMR (DMSO-$d_6$): δ 2.25 (s, 3H), 2.87 (t, J=6.8 Hz, 2H), 3.94 (t, J=7.0 Hz, 2H), 5.07 (s, 2H), 6.98 (m, 3H), 7.16 (t, J=7.6 Hz, 1H), 7.37-7.45 (m, 5H), 12.14 (s, 1H).

6-Hydroxy-2-(3-methylphenethyl)-1,2,4-triazine-3,5(2H,4H)-dione (5i)

Compound 5i was prepared as described for the preparation of 5a with the exception that methanol and ethyl acetate were used as co-solvents and the hydrogenation was performed overnight at 30 psi. Yield: 82% (white solid). Mp 210-211° C.; $^1$H NMR (DMSO-$d_6$): δ 2.27 (s, 3H), 2.86 (t, J=7.3 Hz, 2H), 3.85 (t, J=7.2 Hz, 2H), 6.99 (m, 3H), 7.18 (t, J=7.8 Hz, 2H), 11.71 (s, 1H), 12.01 (s, 1H).

Example 10

Synthesis of 6-Hydroxy-2-(2-methylphenethyl)-1,2,4-triazine-3,5(2H,4H)-dione

6-Bromo-2-(2-methylphenethyl)-1,2,4-triazine-3,5(2H,4H)-dione (3j)

Compound 3j was prepared as described for the preparation of 3a with the exception that 2.0 equiv of 3-methyl-4-(2-iodoethyl)benzene were used in one portion in place of sequential addition of 2.5 equivalents of phenethyl iodide. Yield: 52% (tan solid). $^1$H NMR (DMSO-$d_6$): δ 2.31 (s, 3H), 2.94 (m, 2H), 3.98 (m, 2H), 7.12 (m, 3H), 7.15 (m, 1H), 12.54 (s, 1H).

6-(Benzyloxy)-2-(2-methylphenethyl)-1,2,4-triazine-3,5(2H,4H)-dione (4j)

Compound 4j was prepared as described for the preparation of 4a. Yield: 66% (beige powder). $^1$H NMR (DMSO-$d_6$): δ 2.30 (s, 3H), 2.90 (t, J=7.5 Hz, 2H), 3.90 (t, J=7.8 Hz, 2H), 5.07 (s, 2H), 7.03 (m, 1H), 7.09-7.12 (m, 2H), 7.14 (m, 1H), 7.36-7.45 (m, 5H), 12.16 (s, 1H).

6-Hydroxy-2-(2-methylphenethyl)-1,2,4-triazine-3,5(2H,4H)-dione (5j)

Compound 5j was prepared as described for the preparation of 5a with the exception that methanol and ethyl acetate were used as cosolvents and the hydrogenation was performed at 30 psi for 2 h. Yield: 71% (grey solid). Mp 207-208° C.; $^1$H NMR (DMSO-$d_6$): δ 2.31 (s, 3H), 2.89 (t, J=7.7 Hz, 2H), 3.81 (t, J=7.7 Hz, 2H), 7.10 (m, 3H), 7.14 (m, 1H), 11.93 (bs, 2H).

Example 11

Synthesis of 6-hydroxy-2-(4-(trifluoromethyl)phenethyl)-1,2,4-triazine-3,5(2H,4H)-dione 6-Bromo-2-(4-(trifluoromethyl)phenethyl)-1,2,4-triazine-3,5(2H,4H)-dione (3k)

Compound 3k was prepared as described for the preparation of 3a with the exception that 2.0 equiv of 3-methyl-4-(2-iodoethyl)benzene were used in one portion in place of sequential addition of 2.5 equivalents of phenethyl iodide. The compound was purified by Biotage Isolera One using EtOAc/hexanes. Yield: 69% (yellow solid). $^1$H NMR (DMSO-$d_6$): δ 3.04 (t, J=7.2 Hz, 2H), 4.08 (t, J=7.1 Hz, 2H), 7.46 (d, J=7.1 Hz, 2H), 7.64 (d, J=8.1 Hz, 2H), 12.53 (s, 1H).

6-(Benzyloxy)-2-(4-(trifluoromethyl)phenethyl)-1,2,4-triazine-3,5(2H,4H)-dione (4k)

Compound 4k was prepared as described for the preparation of 4a. Yield: 71% (white solid). $^1$H NMR (DMSO-$d_6$): δ 3.01 (t, J=6.7 Hz, 2H), 4.01 (t, J=6.8 Hz, 2H), 5.02 (s, 2H), 7.38-7.42 (m, 7H), 7.62 (d, J=8.1 Hz, 2H), 12.13 (s, 1H).

6-Hydroxy-2-(4-(trifluoromethyl)phenethyl)-1,2,4-triazine-3,5(2H,4H)-dione (5k)

Compound 5k was prepared as described for the preparation of 5a with the exception that methanol and ethyl acetate were used as cosolvents and the hydrogenation was performed overnight at 30 psi. Yield: 83% (white solid). Mp 222-223° C.; $^1$H NMR (DMSO-$d_6$): δ 3.01 (t, J=7.1 Hz, 2H), 3.92 (t, J=7.1 Hz, 2H), 7.42 (d, J=7.8 Hz, 2H), 7.64 (d, J=8.1 Hz, 2H), 11.71 (s, 1H), 12.02 (s, 1H).

Example 12

Synthesis of 6-hydroxy-2-(3-(trifluoromethyl)phenethyl)-1,2,4-triazine-3,5(2H,4H)-dione

6-Bromo-2-(3-(trifluoromethyl)phenethyl)-1,2,4-triazine-3,5(2H,4H)-dione (3l)

Compound 3l was prepared as described for the preparation of 3a with the exception that 2.0 equiv of 3-methyl-4-(2-iodoethyl)benzene were used in one portion in place of sequential addition of 2.5 equivalents of phenethyl iodide. Yield: 48% (yellow solid). $^1$H NMR (DMSO-$d_6$): δ 3.06 (t, J=7.2 Hz, 2H), 4.10 (t, J=7.1 Hz, 2H), 7.55 (m, 4H), 12.53 (s, 1H).

6-(Benzyloxy)-2-(3-(trifluoromethyl)phenethyl)-1,2,4-triazine-3,5(2H,4H)-dione (4l)

Compound 4l was prepared as described for the preparation of 4a with the exception that the product was purified by Biotage Isolera One using EtOAc/hexanes. Yield: 85% (white solid). $^1$H NMR (DMSO-$d_6$): δ 3.02 (t, J=6.7 Hz, 2H), 4.01 (t, J=6.8 Hz, 2H), 5.00 (s, 2H), 7.36 (m, 1H), 7.40 (m, 4H), 7.50 (m, 4H), 12.13 (s, 1H).

6-Hydroxy-2-(3-(trifluoromethyl)phenethyl)-1,2,4-triazine-3,5(2H,4H)-dione (5l)

Compound 5l was prepared as described for the preparation of 5a with the exception that only methanol was used as solvent and the hydrogenation was performed at 30 psi for 1.5 h. Yield: 85% (white powder). Mp 201-203° C.; $^1$H NMR (DMSO-$d_6$): δ 3.02 (t, J=7.1 Hz, 2H), 3.93 (t, J=7.2 Hz, 2H), 7.51 (m, 3H), 7.574 (m, 1H), 11.70 (s, 1H), 12.03 (s, 1H).

Example 13

Synthesis of 2-(2,4-dichlorophenethyl)-6-hydroxy-1,2,4-triazine-3,5(2H,4H)-dione

6-Bromo-2-(2,4-dichlorophenethyl)-1,2,4-triazine-3,5(2H,4H)-dione (3m)

Compound 3m was prepared as described for the preparation of 3a with the exception that 2.0 equiv of 3-methyl-4-(2-iodoethyl)benzene were used in one portion in place of sequential addition of 2.5 equivalents of phenethyl iodide. Yield: 44% (tan solid). $^1$H NMR (, DMSO-$d_6$): δ 3.05 (t, J=6.8 Hz, 2H), 4.07 (t, J=6.9 Hz, 2H), 7.37 (m, 2H), 7.59 (m, 1H), 12.54 (s, 1H).

6-(Benzyloxy)-2-(2,4-dichlorophenethyl)-1,2,4-triazine-3,5(2H,4H)-dione (4m)

Compound 4m was prepared as described for the preparation of 4a with the exception that the DMF was used with benzyl alcohol as cosolvent due to low solubility of the starting material. The product was purified by Biotage Isolera One using EtOAc/hexanes. Yield: 68% (white cake). $^1$H NMR (DMSO-$d_6$): δ 3.03 (t, J=6.6 Hz, 2H), 4.00 (t, J=6.6 Hz, 2H), 4.94 (s, 2H), 7.24 (d, J=8.3 Hz, 1H), 7.34 (m, 1H), 7.38-7.41 (m, 5H), 7.59 (t, J=2.3 Hz, 1H), 12.15 (s, 1H).

2-(2,4-Dichlorophenethyl)-6-hydroxy-1,2,4-triazine-3,5(2H,4H)-dione (5m)

Compound 5m was prepared as described for the preparation of 5e with the exception that 2 equiv of boron tribromide were added at rt in one portion and that the reaction was stirred at rt for 2.5 h. Yield: 94% (beige powder). Mp 204-206° C.; $^1$H NMR (DMSO-$d_6$): δ 3.02 (t, J=6.8 Hz, 2H), 3.90 (t, J=6.8 Hz, 2H), 7.32 (m, 2H), 7.58 (d, J=2.0 Hz, 1H), 11.68 (s, 1H), 12.04 (s, 1H).

Example 14

Synthesis of 6-hydroxy-2-(2-(naphthalen-1-yl)ethyl)-1,2,4-triazine-3,5(2H,4H)-dione

6-Bromo-2-(2-(naphthalen-1-yl)ethyl)-1,2,4-triazine-3,5(2H,4H)-dione (3n)

Compound 3n was prepared as described for the preparation of 3a with the exception that 2.0 equiv of 1-(2-iodoethyl)naphthalene were used in one portion in place of sequential addition of 2.5 equivalents of phenethyl iodide. Yield: 46% (tan solid). $^1$H NMR (DMSO-$d_6$): δ 3.41 (t, J=7.5 Hz, 2H), 4.13 (t, J=7.6 Hz, 2H), 7.43 (m, 2H), 7.55 (m, 2H), 7.81 (d, J=8.3 Hz, 1H), 7.93 (d, J=7.8 Hz, 1H), 8.13 (d, J=8.3 Hz, 1H), 12.56 (s, 1H).

6-(Benzyloxy)-2-(2-(naphthalen-1-yl)ethyl)-1,2,4-triazine-3,5(2H,4H)-dione (4n)

Compound 4n was prepared as described for the preparation of 4a. Yield: 56% (yellow solid). $^1$H NMR (DMSO-$d_6$): δ 3.38 (t, J=6.8 Hz, 2H), 4.06 (t, J=7.1 Hz, 2H), 4.91 (s, 2H), 7.30 (m, 1H), 7.37-7.44 (m, 6H), 7.54 (m, 2H), 7.80 (d, J=8.1 Hz, 1H), 7.92 (d, J=6.6 Hz, 1H), 8.09 (d, J=7.8 Hz, 1H) 12.15 (s, 1H).

6-Hydroxy-2-(2-(naphthalen-1-yl)ethyl)-1,2,4-triazine-3,5(2H,4H)-dione (5n)

Compound 5n was prepared as described for the preparation of 5a with the exception the hydrogenation was performed overnight at 30 psi. Yield: 90% (light pink powder). Mp>300° C. (decomp.); $^1$H NMR (DMSO-$d_6$): δ 3.37 (t, J=8.1 Hz, 2H), 3.93 (bs, 2H), 7.38 (bs, 1H), 7.44 (t, J=7.5 Hz, 1H), 7.53 (t, J=7.8 Hz, 1H), 7.59 (t, J=7.2 Hz, 1H), 7.80 (d, J=8.1 Hz, 1H), 7.92 (d, J=7.8 Hz, 1H), 8.20 (bs, 1H), 11.95 (s, 1H), 12.28 (d, 1H).

Example 15

Synthesis of 2-(2-(biphenyl-4-yl)ethyl)-6-hydroxy-1,2,4-triazine-3,5(2H,4H)-dione 2-(2-(Biphenyl-4-yl)ethyl)-6-bromo-1,2,4-triazine-3,5(2H,4H)-dione (3o)

Compound 3o was prepared as described for the preparation of 3a with the exception that 2.0 equiv of 3-methyl-4-(2-iodoethyl)benzene were used in one portion in place of sequential addition of 2.5 equivalents of phenethyl iodide. Yield: 59% (tan solid). $^1$H NMR (DMSO-d$_6$): δ 2.99 (t, J=7.5 Hz, 2H), 4.08 (t, J=7.6 Hz, 2H), 7.31-7.37 (m, 3H), 7.45 (t, J=7.6 Hz, 2H), 7.59-7.65 (m, 4H), 12.55 (s, 1H).

6-(Benzyloxy)-2-(2-(biphenyl-4-yl)ethyl)-1,2,4-triazine-3,5(2H,4H)-dione (4o)

Compound 4o was prepared as described for the preparation of 4a with the exception that the product was purified by Biotage Isolera One using EtOAc/hexanes. Yield: 53% (white solid). $^1$H NMR (DMSO-d$_6$): δ 2.96 (t, J=7.2 Hz, 2H), 4.00 (t, J=7.1 Hz, 2H), 5.05 (s, 2H), 7.25 (d, J=8.1 Hz, 2H), 7.34-7.46 (m, 8H), 7.58-7.64 (m, 4H), 12.16 (s, 1H).

2-(2-(Biphenyl-4-yl)ethyl)-6-hydroxy-1,2,4-triazine-3,5(2H,4H)-dione (5o)

Compound 5o was prepared as described for the preparation of 5a with the exception that methanol and ethyl acetate were used as co-solvents and the hydrogenation was performed overnight at 30 psi. Yield: 89% (white powder). Mp 254-255° C.; $^1$H NMR (DMSO-d$_6$): δ 2.95 (t, J=7.6 Hz, 2H), 3.92 (t, J=7.5 Hz, 2H), 7.28 (d, J=8.1 Hz, 2H), 7.35 (t, J=6.8 Hz, 1H), 7.45 (t, J=7.6 Hz, 2H), 7.59 (d, J=8.3 Hz, 2H), 7.63 (d, J=7.1 Hz, 2H), 11.71 (s, 1H), 12.06 (s, 1H).

Example 16

Synthesis of 6-hydroxy-2-methyl-1,2,4-triazine-3,5(2H,4H)-dione

6-Bromo-2-methyl-1,2,4-triazine-3,5(2H,4H)-dione (3p)

Compound 3p was prepared as described for the preparation of 3a with the exception that a total of 1.7 equiv of methyl iodide were used. Yield: 34% (black solid). $^1$H NMR (DMSO-d$_6$): δ 3.44 (s, 3H), 12.50 (s, 1H).

6-(Benzyloxy)-2-methyl-1,2,4-triazine-3,5(2H,4H)-dione (4p)

Compound 4p was prepared as described for the preparation of 4a with the exception that the product was purified by Biotage Isolera One using EtOAc/hexanes. Yield: 59% (white solid). $^1$H NMR (DMSO-d$_6$): δ 3.36 (s, 3H), 5.12 (s, 2H), 7.37-7.46 (m, 5H), 12.16 (s, 1H).

6-Hydroxy-2-methyl-1,2,4-triazine-3,5(2H,4H)-dione (5p)

Compound 5p was prepared as described for the preparation of 5a with the exception that only methanol was used as solvent and the hydrogenation was performed at 30 psi for 1 h. Yield: 95% (beige solid). Mp 259-261° C.; $^1$H NMR (DMSO-d$_6$): δ 3.27 (s, 3H), 11.11 (s, 1H), 12.03 (s, 1H).

Example 17

Synthesis of 6-hydroxy-2-isopentyl-1,2,4-triazine-3,5(2H,4H)-dione

6-Bromo-2-isopentyl-1,2,4-triazine-3,5(2H,4H)-dione (3q)

Compound 3q was prepared as described for the preparation of 3a with the exception that 1.6 equiv of 1-iodo-3-methylbutane were used. Yield: 27% (yellow solid). $^1$H NMR (DMSO-d$_6$): δ 0.89 ((d, J=6.3 Hz, 6H), 1.50 (m, 2H), 1.60 (m, 1H), 3.82 (t, J=7.3 Hz, 2H), 12.48 (s, 1H).

6-(Benzyloxy)-2-isopentyl-1,2,4-triazine-3,5(2H,4H)-dione (4q)

Compound 4q was prepared as described for the preparation of 4a with the exception that the product was purified by Biotage Isolera One using EtOAc/hexanes. Yield: 36% (clear oil). $^1$H NMR (DMSO-d$_6$): δ 0.87 (d, J=6.3 Hz, 6H), 1.49 (m, 2H), 1.54 (m, 1H), 3.73 (t, J=7.1 Hz, 2H), 5.14 (s, 2H), 7.36-7.45 (m, 5H), 12.14 (s, 1H).

6-Hydroxy-2-isopentyl-1,2,4-triazine-3,5(2H,4H)-dione (5q)

Compound 5q was prepared as described for the preparation of 5a with the exception that only methanol was used as solvent and the hydrogenation was performed at 30 psi for 1.3 h. Yield: quantitative (grey solid). Mp 171-172° C.; $^1$H NMR (DMSO-d$_6$): δ 0.88 (d, J=6.3 Hz, 6H), 1.47 (m, 2H), 1.54 (m, 1H), 3.66 (t, J=7.3 Hz, 2H), 11.65 (s, 1H), 11.94 (s, 1H).

Example 18

Synthesis of 2-(3,3-dimethylbutyl)-6-hydroxy-1,2,4-triazine-3,5(2H,4H)-dione

6-Bromo-2-(3,3-dimethylbutyl)-1,2,4-triazine-3,5(2H,4H)-dione (3r)

Compound 3r was prepared as described for the preparation of 3a with the exception that a total of 3.3 equiv of 1-iodo-3,3-dimethylbutane were used and the product was purified by Biotage Isolera One using EtOAc/hexanes. Yield: 19% (clear oil). $^1$H NMR (DMSO-d$_6$): δ 0.92 (s, 9H), 1.53 (m, 2H), 3.82 (m, 2H), 12.50 (s, 1H).

6-(Benzyloxy)-2-(3,3-dimethylbutyl)-1,2,4-triazine-3,5(2H,4H)-dione (4r)

Compound 4r was prepared as described for the preparation of 4a with the exception that the product was purified by Biotage Isolera One using EtOAc/hexanes. Yield: 80% (clear oil). $^1$H NMR (DMSO-d$_6$): δ 0.90 (s, 9H), 1.48 (m, 2H), 3.72 (m, 2H), 5.15 (s, 2H), 7.35-7.45 (m, 5H), 12.15 (s, 1H).

2-(3,3-Dimethylbutyl)-6-hydroxy-1,2,4-triazine-3,5(2H,4H)-dione (5r)

Compound 5r was prepared as described for the preparation of 5a with the exception that only methanol was used as solvent and the hydrogenation was performed at 30 psi for 1.3 h. Yield: 77% (white solid). Mp 218-220° C.; $^1$H NMR (DMSO-d$_6$): δ 0.91 (m, 9H), 1.50 (m, 2H), 3.67 (m, 2H), 11.64 (s, 1H), 12.02 (s, 1H).

Example 19

Synthesis of 6-hydroxy-2-(3-phenylpropyl)-1,2,4-triazine-3,5(2H,4H)-dione

6-Bromo-2-(3-phenylpropyl)-1,2,4-triazine-3,5(2H,4H)-dione (3s)

Compound 3s was prepared as described for the preparation of 3a with the exception that 1.6 equiv of (3-iodopropyl)benzene were used and the product was purified by Biotage Isolera One using EtOAc/hexanes. Yield: 43% (white solid). $^1$H NMR (DMSO-d$_6$): δ 1.94 (m, 2H), 2.63 (t, J=7.7 Hz, 2H), 3.83 (t, J=6.9 Hz, 2H), 7.15-7.22 (m, 3H), 7.25-7.29 (m, 2H), 12.45 (s, 1H).

6-(Benzyloxy)-2-(3-phenylpropyl)-1,2,4-triazine-3,5(2H,4H)-dione (4s)

Compound 4s was prepared as described for the preparation of 4a with the exception that the product was purified by Biotage Isolera One using EtOAc/hexanes. Yield: 85% (clear oil). $^1$H NMR (DMSO-d$_6$): δ 1.93 (m, 2H), 2.60 (t, J=7.7 Hz, 2H), 3.76 (t, J=6.8 Hz, 2H), 5.13 (s, 2H), 7.18 (m, 3H), 7.24 (m, 2H), 7.35-7.46 (m, 5H), 12.09 (s, 1H).

6-Hydroxy-2-(3-phenylpropyl)-1,2,4-triazine-3,5(2H,4H)-dione (5s)

Compound 5s was prepared as described for the preparation of 5a with the exception that the hydrogenation was performed at 30 psi for 1.4 h. Yield: 85% (light pink solid). Mp 152-154° C.; $^1$H NMR (DMSO-d$_6$): δ 1.89 (m, 2H), 2.60 (t, J=7.6 Hz, 2H), 3.67 (t, J=6.9 Hz, 2H), 7.20 (m, 3H), 7.25 (m, 2H), 11.65 (bs, 1H), 11.93 (bs, 1H)

Example 20

Synthesis of 2-benzyl-6-hydroxy-1,2,4-triazine-3,5(2H,4H)-dione

2-Benzyl-6-bromo-1,2,4-triazine-3,5(2H,4H)-dione (3t)

Compound 3t was prepared as described for the preparation of 3a with the exception that 1.2 equiv of benzyl bromide was used in place of phenethyl iodide. Yield: 71% (light tan solid). $^1$H NMR (DMSO-d$_6$): δ 5.02 (s, 2H), 7.29-7.38 (m, 5H), 12.59 (s, 1H).

2-Benzyl-6-(benzyloxy)-1,2,4-triazine-3,5(2H,4H)-dione (4t)

Compound 4t was prepared as described for the preparation of 4a. Yield: 70% (white solid). $^1$H NMR (DMSO-d$_6$): δ 4.91 (s, 2H), 5.11 (s, 2H), 7.29-7.40 (m, 10H), 12.24 (s, 1H).

2-Benzyl-6-hydroxy-1,2,4-triazine-3,5(2H,4H)-dione (5t)

Compound 5t was prepared as described for the preparation of 5a with the exception that only methanol was used as solvent and the hydrogenation was performed overnight under a hydrogen-filled balloon. Yield: 81% (light pink powder). Mp 240-244° C.; $^1$H NMR (DMSO-d$_6$): δ 4.85 (s, 2H), 7.26-7.36 (m, 5H), 11.72 (bs, 1H), 11.94 (bs, 2H).

Example 21

6-hydroxy-2-(naphthalen-1-ylmethyl)-1,2,4-triazine-3,5(2H,4H)-dione

6-Bromo-2-(naphthalen-1-ylmethyl)-1,2,4-triazine-3,5(2H,4H)-dione (3u)

Compound 3u was prepared as described for the preparation of 3a with the exception that 1.2 equiv of 1-(bromomethyl)-naphthalene was used in one portion in place of sequential addition of 2.5 equivalents of phenethyl iodide. Yield: 65% (orange solid). $^1$H NMR (DMSO-d$_6$): δ 5.49 (s, 2H), 7.49 (m, 2H), 7.59 (m, 2H), 7.91 (m, 1H), 7.98 (m, 1H), 8.14 (d, J=8.1 Hz, 1H), 12.64 (br s, 1H).

6-(Benzyloxy)-2-(naphthalen-1-ylmethyl)-1,2,4-triazine-3,5(2H,4H)-dione (4u)

Compound 4u was prepared as described for the preparation of 4a with the exception that the product was purified by silica gel chromatography (30% EtOAc in hexanes). Yield: 40% (white solid). $^1$H NMR (DMSO-d$_6$): δ 5.04 (s, 2H), 5.39 (s, 2H), 7.31 (s, 5H), 7.49 (d, J=4.8 Hz, 2H), 7.57 (m, 2H), 7.91 (t, J=4.8 Hz, 1H), 7.98 (m, 1H), 8.22 (d, J=7.6 Hz, 1H), 12.29 (s, 1H).

6-Hydroxy-2-(naphthalen-1-ylmethyl)-1,2,4-triazine-3,5(2H,4H)-dione (5u)

Compound 5u was prepared as described for the preparation of 5a with the exception that only methanol/ethyl acetate/acetic acid mixture (1:1:0.1) was used as solvent and the hydrogenation was performed at 20 psi for 3 h. Yield: 90% (white powder). Mp>260° C. (decomp); $^1$H NMR (DMSO-d$_6$): δ 5.33 (s, 2H), 7.41 (d, J=7.1 Hz, 1H), 7.48 (t, J=7.6 Hz, 1H), 7.57 (m, 2H), 7.88 (d, J=8.1 Hz, 1H), 7.96 (m, 1H), 8.16 (d, J=7.5 Hz, 1H), 11.68 (s, 1H), 12.20 (s, 1H); $^{13}$C NMR (DMSO-d$_6$): δ 50.1, 123.3, 125.5, 126.0 (2), 126.6, 128.0, 128.6, 130.7, 132.2, 133.3, 148.2, 148.8, 153.7.

Example 22

Synthesis of 6-hydroxy-2-(2-methoxyphenethyl)-1,2,4-triazine-3,5(2H,4H)-dione

6-Bromo-2-(2-methoxyphenethyl)-1,2,4-triazine-3,5(2H,4H)-dione (3v)

Compound 3v was prepared as described for the preparation of 3a with the exception that 2.0 equiv of 1-(2-iodoethyl)-2-methoxybenzene were used in one portion in place of sequential addition of 2.5 equivalents of phenethyl iodide. Yield: 57% (tan solid). $^1$H NMR (DMSO-d$_6$): δ 2.91 (t, J=6.9 Hz, 2H), 3.73 (s, 3H), 4.01 (t, J=7.0 Hz, 2H), 6.87 (dt, J=1.0, 7.6 Hz, 1H), 6.93 (d, J=7.6 Hz, 1H), 7.11 (m, 1H), 7.21 (m, 1H), 12.52 (s, 1H).

6-(Benzyloxy)-2-(2-methoxyphenethyl)-1,2,4-triazine-3,5(2H,4H)-dione (4v)

Compound 4v was prepared as described for the preparation of 4a. Yield: 63% (white solid). $^1$H NMR (DMSO-d$_6$):

δ 2.89 (t, J=6.7 Hz, 2H), 3.74 (s, 3H), 3.94 (t, J=6.7 Hz, 2H), 4.89 (s, 2H), 6.84 (t, J=7.3 Hz, 1H), 6.93 (d, J=8.1 Hz, 1H), 7.02 (dd, J=1.8, 7.3 Hz, 1H), 7.20 (m, 1H), 7.35-7.41 (m, 5H), 12.12 (s, 1H).

6-Hydroxy-2-(2-methoxyphenethyl)-1,2,4-triazine-3,5(2H,4H)-dione (5v)

Compound 5v was prepared as described for the preparation of 5a with the exception that methanol and ethyl acetate were used as co-solvents and the hydrogenation was performed overnight at 1 atm ($H_2$ balloon). Yield: 83% (yellow powder). Mp 165-167° C.; $^1$H NMR (DMSO-$d_6$): δ 2.88 (t, J=7.2 Hz, 2H), 3.75 (s, 3H), 3.84 (t, J=7.2 Hz, 2H), 6.85 (dt, J=1.0, 7.3 Hz, 1H), 6.93 (d, J=7.8 Hz, 1H), 7.07 (dt, J=1.5, 7.3 Hz, 1H), 7.20 (dt, J=1.8, 8.1 Hz, 1H), 11.63 (s, 1H), 12.0 (s, 1H).

Example 23

Synthesis of 6-hydroxy-2-(2-hydroxyphenethyl)-1,2,4-triazine-3,5(2H,4H)-dione

6-Hydroxy-2-(2-hydroxyphenethyl)-1,2,4-triazine-3,5(2H,4H)-dione (5vp)

Compound 5v (0.060 g, 0.228 mmol) was dissolved in dichloromethane (3 mL). To this a 1.0 M solution of boron tribromide in dichloromethane (0.685 mL, 0.685 mmol, 3.0 equiv) was added at rt via syringe. The reaction was stirred at rt for 1.5 h and water was added. The mixture was concentrated in vacuo to a small volume and the residue was partitioned between EtOAc and water. The organic layer was washed with brine, dried over $Na_2SO_4$ and concentrated. Purification of the residue by prep-HPLC (method: 20-70% acetonitrile-water-0.1% formic acid) afforded 0.038 g (68%) of compound 5vp as an off-white solid. Mp 204-206° C.; $^1$H NMR (DMSO-$d_6$): δ 2.83 (t, J=7.3 Hz, 2H), 3.83 (t, J=7.3 Hz, 2H), 6.68 (dt, J=1.3, 7.6 Hz, 1H), 6.75 (d, J=7.8 Hz, 1H), 6.97-7.03 (m, 2H), 9.38 (s, 1H), 11.63 (bs, 1H), 11.97 (bs, 1H).

Example 24

Synthesis of 6-hydroxy-2-(3-methoxyphenethyl)-1,2,4-triazine-3,5(2H,4H)-dione

6-Bromo-2-(3-methoxyphenethyl)-1,2,4-triazine-3,5(2H,4H)-dione (3w)

Compound 3w was prepared as described for the preparation of 3a with the exception that 2.0 equiv of 1-(2-iodoethyl)-3-methoxybenzene were used in one portion in place of sequential addition of 2.5 equivalents of phenethyl iodide. Yield: 36% (tan solid). $^1$H NMR (DMSO-$d_6$): δ 2.91 (t, J=7.5 Hz, 2H), 3.73 (s, 3H), 4.04 (m, 2H), 6.77 (m, 1H), 6.79 (m, 2H), 7.21 (t, J=7.7 Hz, 1H), 12.53 (s, 1H).

6-(Benzyloxy)-2-(3-methoxyphenethyl)-1,2,4-triazine-3,5(2H,4H)-dione (4w)

Compound 4w was prepared as described for the preparation of 4a. Yield: 64% (white solid). $^1$H NMR (DMSO-$d_6$): δ 2.89 (t, J=7.1 Hz, 2H), 3.70 (s, 3H), 3.96 (t, J=7.2 Hz, 2H), 5.06 (s, 2H), 6.72-6.78 (m, 3H), 7.19 (t, J=7.8 Hz, 1H), 7.36-7.44 (m, 5H), 12.14 (s, 1H).

6-Hydroxy-2-(3-methoxyphenethyl)-1,2,4-triazine-3,5(2H,4H)-dione (5w)

Compound 5w was prepared as described for the preparation of 5a with the exception that methanol and ethyl acetate were used as co-solvents and the hydrogenation was performed overnight at 30 psi for 2 h. Yield: 63% (off-white solid). Mp 224-225° C.; $^1$H NMR (DMSO-$d_6$): δ 2.88 (t, J=7.6 Hz, 2H), 3.72 (s, 3H), 3.87 (t, J=7.6 Hz, 2H), 6.75-6.78 (m, 3H), 7.20 (t, J=8.0 Hz, 1H), 11.76 (bs, 1H), 11.99 (bs, 1H).

Example 25

Synthesis of 6-hydroxy-2-(3-hydroxyphenethyl)-1,2,4-triazine-3,5(2H,4H)-dione

6-Hydroxy-2-(3-hydroxyphenethyl)-1,2,4-triazine-3,5(2H,4H)-dione (5wp)

Compound 5wp was prepared as described for the preparation of 5v. Yield: 53% (white solid). Mp 232-233° C.; $^1$H NMR (DMSO-$d_6$): δ 2.80 (t, J=7.2 Hz, 2H), 3.83 (t, J=7.2 Hz, 2H), 6.58 (m, 3H), 7.07 (t, J=7.7 Hz, 1H), 9.32 (s, 1H), 11.69 (s, 1H), 12.04 (s, 1H).

Example 26

Synthesis of 6-hydroxy-2-(4-methoxyphenethyl)-1,2,4-triazine-3,5(2H,4H)-dione

6-Bromo-2-(4-methoxyphenethyl)-1,2,4-triazine-3,5(2H,4H)-dione (3x)

Compound 3x was prepared as described for the preparation of 3a with the exception that 2.0 equiv of 1-(2-iodoethyl)-4-methoxybenzene were used in one portion in place of sequential addition of 2.5 equivalents of phenethyl iodide. Yield: 58% (tan solid). $^1$H NMR (DMSO-$d_6$): δ 2.87 (t, J=7.5 Hz, 2H), 3.71 (s, 3H), 3.99 (m, 2H), 6.84 (d, J=8.6 Hz, 2H), 7.12 (m, 2H), 12.52 (s, 1H).

6-(Benzyloxy)-2-(4-methoxyphenethyl)-1,2,4-triazine-3,5(2H,4H)-dione (4x)

Compound 4x was prepared as described for the preparation of 4a. Yield: 70% (white solid). $^1$H NMR (DMSO-$d_6$): δ 2.84 (t, J=7.1 Hz, 2H), 3.69 (s, 3H), 3.91 (t, J=7.1 Hz, 2H), 5.06 (s, 2H), 6.82 (t, J=8.8 Hz, 2H), 7.05 (t, J=8.6 Hz, 2H), 7.17 (m, 2H), 7.36-7.44 (m, 5H), 12.12 (s, 1H).

6-Hydroxy-2-(4-methoxyphenethyl)-1,2,4-triazine-3,5(2H,4H)-dione (5x)

Compound 5x was prepared as described for the preparation of 5a with the exception that methanol and ethyl acetate were used as co-solvents and the hydrogenation was performed overnight at 50 psi for 3 h. Yield: 62% (off white solid). Mp 243-245° C.; $^1$H NMR (DMSO-$d_6$): δ 2.83 (t, J=7.5 Hz, 2H), 3.71 (s, 3H), 3.82 (t, J=7.5 Hz, 2H), 6.83 (d, J=8.6 Hz, 2H), 7.09 (d, J=8.6 Hz, 2H), 11.74 (bs, 1H), 11.98 (bs, 1H).

Example 27

Synthesis of 6-hydroxy-2-(4-hydroxyphenethyl)-1,2,4-triazine-3,5(2H,4H)-dione 6-Hydroxy-2-(4-hydroxyphenethyl)-1,2,4-triazine-3,5(2H,4H)-dione (5xp)

Compound 5xp was prepared as described for the preparation of 5v. Yield: 54% (light pink solid). Mp>280° C. (decomp); $^1$H NMR (DMSO-d$_6$): δ 2.78 (t, J=7.6 Hz, 2H), 3.80 (t, J=7.6 Hz, 2H), 6.65 (d, J=8.3 Hz, 2H), 6.96 (d, J=8.3 Hz, 2H), 9.22 (s, 1H), 11.66 (s, 1H), 12.01 (s, 1H).

Example 28

Synthesis of 2-(3,4-dichlorophenethyl)-6-hydroxy-1,2,4-triazine-3,5(2H,4H)-dione 6-Bromo-2-(2-(3,4-dichlorophenyl)-2-oxoethyl)-1,2,4-triazine-3,5(2H,4H)-dione (3y)

Compound 3y was prepared as described for the preparation of 3a with the exception that 2.0 equiv of 1,2-dichloro-4-(2-iodoethyl)benzene were used in one portion in place of sequential addition of 2.5 equivalents of phenethyl iodide and that the reaction was heated at 120° C. in N,N-dimethylacetamide in place of acetonitrile. The product was purified by Biotage Isolera One using EtOAc/hexanes. Yield: 50% (beige solid). $^1$H NMR (DMSO-d$_6$): δ 2.95 (t, J=6.8 Hz, 2H), 4.06 (t, J=7.1 Hz, 2H), 7.22 (m, 1H), 7.53-7.56 (m, 2H), 12.52 (s, 1H).

6-(Benzyloxy)-2-(3,4-dichlorophenethyl)-1,2,4-triazine-3,5(2H,4H)-dione (4y)

Compound 4y was prepared as described for the preparation of 4a with the exception that the product was purified by Biotage Isolera One using EtOAc/hexanes. Yield: 77% (white solid). $^1$H NMR (DMSO-d$_6$): δ 2.92 (t, J=6.8 Hz, 2H), 3.98 (t, J=6.6 Hz, 2H), 5.04 (s, 2H), 7.11 (dd, J=2.0, 8.1 Hz, 1H), 7.36-7.43 (m, 5H), 7.47 (d, J=2.0 Hz, 1H), 7.50 (d, J=8.1 Hz, 1H), 12.12 (s, 1H).

2-(3,4-Dichlorophenethyl)-6-hydroxy-1,2,4-triazine-3,5(2H,4H)-dione (5y)

Compound 5y was prepared as described for the preparation of 5e with the exception that 2 equiv of boron tribromide were added at rt in one portion and that the reaction was stirred at rt for 50 min. The compound was subjected to purification by prepatory HPLC (method: 20-70% acetonitrile-water-0.1% formic acid) to give 5y as a light yellow solid. Yield: 67%. Mp 241-243° C.; $^1$H NMR (DMSO-d$_6$): δ 2.92 (t, J=7.1 Hz, 2H), 3.90 (t, J=7.1 Hz, 2H), 7.16 (dd, J=2.0, 8.3 Hz, 1H), 7.52 (m, 2H), 11.69 (s, 1H), 12.03 (s, 1H).

Example 29

Synthesis of 2-(3-chloro-4-fluorophenethyl)-6-hydroxy-1,2,4-triazine-3,5(2H,4H)-dione 6-Bromo-2-(3-chloro-4-fluorophenethyl)-1,2,4-triazine-3,5(2H,4H)-dione (3z)

Compound 3z was prepared as described for the preparation of 3a with the exception that 2.0 equiv of 2-chloro-1-fluoro-4-(2-iodoethyl)benzene were used in one portion in place of sequential addition of 2.5 equivalents of phenethyl iodide and the reaction was heated at 85° C. for 3h in N,N-dimethylacetamide in place of acetonitrile. The product was purified by Biotage Isolera One using EtOAc/hexanes. Yield: 60% (light yellow solid). $^1$H NMR (DMSO-d$_6$): δ 2.94 (t, J=7.3 Hz, 2H), 4.05 (t, J=6.8 Hz, 2H), 7.23 (m, 1H), 7.32 (t, J=8.8 Hz, 1H), 7.50 (dt, J=2.0, 7.3 Hz, 1H), 12.52 (s, 1H).

6-(Benzyloxy)-2-(3-chloro-4-fluorophenethyl)-1,2,4-triazine-3,5(2H,4H)-dione (4z)

Compound 4z was prepared as described for the preparation of 4a with the exception that the product was purified by Biotage Isolera One using EtOAc/hexanes. Yield: 65% (white solid). $^1$H NMR (DMSO-d$_6$): δ 2.91 (t, J=6.6 Hz, 2H), 3.97 (t, J=6.8 Hz, 2H), 5.06 (s, 2H), 7.13 (m, 2H), 7.29 (t, J=9.6 Hz, 1H), 7.36-7.43 (m, 5H), 12.12 (s, 1H).

2-(3-Chloro-4-fluorophenethyl)-6-hydroxy-1,2,4-triazine-3,5(2H,4H)-dione (5z)

Compound 5z was prepared as described for the preparation of 5e with the exception that 2 equiv of boron tribromide were added at rt in one portion and that the reaction was stirred at rt for 20 min. The compound was subjected to purification by prepatory HPLC (method: 20-70% acetonitrile-water-0.1% formic acid) to give 5z as a light yellow solid. Yield: 72%. Mp 223-225° C.; $^1$H NMR (DMSO-d$_6$): δ 2.91 (t, J=7.1 Hz, 2H), 3.89 (t, J=7.3 Hz, 2H), 7.18 (m, 1H), 7.31 (t, J=9.3 Hz, 1H), 7.43 (dd, J=2.0, 7.3 Hz, 1H), 11.68 (s, 1H), 12.03 (s, 1H).

Example 30

Synthesis of 6-hydroxy-2-(naphthalen-2-ylmethyl)-1,2,4-triazine-3,5(2H,4H)-dione 6-Bromo-2-(naphthalen-2-ylmethyl)-1,2,4-triazine-3,5(2H,4H)-dione (3aa)

Compound 3aa was prepared as described for the preparation of 3a with the exception that 1.2 equiv of 2-(bromomethyl)naphthalene were used in one portion in place of phenethyl iodide and the reaction was heated overnight. Yield: 56% (tan solid). $^1$H NMR (DMSO-d$_6$): δ 5.20 (s, 2H), 7.46 (dd, J=1.5, 8.3 Hz, 1H), 7.51 (m, 2H), 7.22 (m, 1H), 7.86-7.92 (m, 4H), 12.62 (s, 1H).

6-(Benzyloxy)-2-(naphthalen-2-ylmethyl)-1,2,4-triazine-3,5(2H,4H)-dione (4aa)

Compound 4aa was prepared as described for the preparation of 4a with the exception that the product was purified by Biotage Isolera One using EtOAc/hexanes. Yield: 76% (white solid foam). $^1$H NMR (DMSO-d$_6$): δ 5.09 (s, 2H), 5.12 (s, 2H), 7.26-7.31 (m, 3H), 7.36 (m, 2H), 7.45 (dd, J=1.8, 7.6 Hz, 1H), 7.50-7.53 (m, 2H), 7.85-7.92 (m, 4H), 12.27 (s, 1H).

6-Hydroxy-2-(naphthalen-2-ylmethyl)-1,2,4-triazine-3,5(2H,4H)-dione (5aa)

Compound 5aa was prepared as described for the preparation of 5e with the exception that 4 equiv of boron tribromide were added at rt in two portions and that the reaction was stirred at rt for 2 h. The crude residue was purified by prep-HPLC (method: 20-70% acetonitrile-water-0.1% formic acid) to give 30% of compound 5aa as a white fluffy solid. Mp 263-265° C.; $^1$H NMR (DMSO-$d_6$): δ 5.03 (s, 2H), 7.44 (dd, J=1.3, 8.3 Hz, 1H), 7.49 (m, 2H), 7.80 (s, 1H), 7.88 (m, 3H), 12.07 (bs, 2H).

Example 31

Synthesis of 2-((6-fluoronaphthalen-2-yl)methyl)-6-hydroxy-1,2,4-triazine-3,5(2H,4H)-dione 6-Bromo-2-((6-fluoronaphthalen-2-yl)methyl)-1,2,4-triazine-3,5(2H,4H)-dione (3ab)

Compound 3ab was prepared as described for the preparation of 3a with the exception that 1.2 equiv of 2-(bromomethyl)-6-fluoronaphthalene were used in one portion in place of phenethyl iodide and the reaction was heated overnight. Yield: 53% (beige solid). $^1$H NMR (DMSO-$d_6$): δ 5.18 (s, 2H), 7.44 (m, 1H), 7.52 (m, 1H), 7.72 (m, 1H), 7.92 (m, 2H), 8.01 (m, 1H), 12.62 (s, 1H).

6-(Benzyloxy)-2-((6-fluoronaphthalen-2-yl)methyl)-1,2,4-triazine-3,5(2H,4H)-dione (4ab)

Compound 4ab was prepared as described for the preparation of 4a. Yield: 70% (white solid). $^1$H NMR (DMSO-$d_6$): δ 5.08 (s, 2H), 5.11 (s, 2H), 7.30 (m, 3H), 7.36 (m, 2H), 7.43 (dt, J=2.5, 9.1 Hz, 1H), 7.49 (d, J=8.6 Hz, 1H), 7.70 (dd, J=2.5, 10.1 Hz, 1H), 7.87 (m, 2H), 8.00 (dd, J=6.1, 9.4 Hz, 1H), 12.27 (s, 1H).

2-((6-Fluoronaphthalen-2-yl)methyl)-6-hydroxy-1,2,4-triazine-3,5(2H,4H)-dione (5ab)

Compound 5ab was prepared as described for the preparation of 5e with the exception that 3.6 equiv of boron tribromide were added at rt in two portions and that the reaction was stirred at rt for 1.5 h. The crude material was triturated in methanol. The solid was filtered off and the filtrate was concentrated. The resulting residue was purified by prep-HPLC (method: 20-70% acetonitrile-water-0.1% formic acid) to give 49% of compound 5ab as a white powder. Mp>260° C. (decomp); $^1$H NMR (DMSO-$d_6$): δ 5.03 (s, 2H), 7.43 (dt, J=2.5, 8.83 Hz, 1H), 7.48 (d, J=8.3 Hz, 1H), 7.68 (dd, J=2.3, 10.1 Hz, 1H), 7.85 (s, 1H), 7.89 (d, J=8.3 Hz, 1H), 8.00 (dd, J=5.8, 8.8 Hz, 1H), 12.18 (s, 1H).

Example 32

Synthesis of 6-hydroxy-2-(4-phenoxyphenethyl)-1,2,4-triazine-3,5(2H,4H)-dione

6-Bromo-2-(4-phenoxyphenethyl)-1,2,4-triazine-3,5(2H,4H)-dione (3ac)

Compound 3ac was prepared as described for the preparation of 3a with the exception that 2.0 equiv of 1-(2-iodoethyl)-4-phenoxybenzene were used in one portion in place of sequential addition of 2.5 equivalents of phenethyl iodide. Yield: 24% (tan solid). $^1$H NMR (DMSO-$d_6$): δ 2.93 (m, 2H), 4.04 (m, 2H), 6.93-6.98 (m, 4H), 7.10-7.14 (m, 1H), 7.21-7.25 (m, 2H), 7.36-7.40 (m, 2H), 12.54 (s, 1H).

6-(Benzyloxy)-2-(4-phenoxyphenethyl)-1,2,4-triazine-3,5(2H,4H)-dione (4ac)

Compound 4ac was prepared as described for the preparation of 4a. Yield: 41% (white solid). $^1$H NMR (DMSO-$d_6$): δ 2.90 (t, J=7.0 Hz, 2H), 3.96 (t, J=7.0 Hz, 2H), 5.08 (s, 2H), 6.91-6.96 (m, 4H), 7.09-7.12 (m, 1H), 7.16-7.18 (m, 2H), 7.33-7.45 (m, 7H), 12.14 (s, 1H).

6-Hydroxy-2-(4-methoxyphenethyl)-1,2,4-triazine-3,5(2H,4H)-dione (5ac)

Compound 5ac was prepared as described for the preparation of 5e with the exception that the final compound was triturated with EtOAc-hexanes. Yield: 69% (white solid). Mp 207-209° C.; $^1$H NMR (DMSO-$d_6$): δ 2.90 (t, J=7.2 Hz, 2H), 3.88 (t, J=7.3 Hz, 2H), 6.92-6.98 (m, 4H), 7.10-7.14 (m, 1H), 7.21 (m, 2H), 7.35-7.40 (m, 2H), 11.69 (bs, 1H), 12.04 (bs, 1H).

Example 33

Synthesis of 6-hydroxy-2-(3-phenoxyphenethyl)-1,2,4-triazine-3,5(2H,4H)-dione

6-Bromo-2-(3-phenoxyphenethyl)-1,2,4-triazine-3,5(2H,4H)-dione (3ad)

Compound 3ad was prepared as described for the preparation of 3a with the exception that 2.0 equiv of 1-(2-iodoethyl)-3-phenoxybenzene were used in one portion in place of sequential addition of 2.5 equivalents of phenethyl iodide. Yield: 21% (white solid). $^1$H NMR (DMSO-$d_6$): δ 2.93 (t, J=7.1 Hz, 2H), 4.05 (t, J=7.1 Hz, 2H), 6.85-6.67 (m, 2H), 6.95-7.01 (m, 3H), 7.10-7.15 (m, 1H), 7.29-7.39 (m, 3H), 12.53 (s, 1H).

6-(Benzyloxy)-2-(3-phenoxyphenethyl)-1,2,4-triazine-3,5(2H,4H)-dione (4ad)

Compound 4ad was prepared as described for the preparation of 4a. Yield: 52% (white solid). $^1$H NMR (DMSO-$d_6$): δ 2.88 (t, J=6.5 Hz, 2H), 3.96 (t, J=6.5 Hz, 2H), 5.03 (s, 2H), 6.75 (m, 1H), 6.84-6.86 (m, 1H), 6.91-6.96 (m, 3H), 7.09-7.13 (m, 1H), 7.28-7.39 (m, 8H), 12.14, (bs, 1H).

6-Hydroxy-2-(3-phenoxyphenethyl)-1,2,4-triazine-3,5(2H,4H)-dione (5ad)

Compound 5ad was prepared as described for the preparation of 5a with the exception that the final compound was hydrogenated in MeOH/EtOAc (1:1). Yield: 78% (tan solid). Mp 150-153° C.; $^1$H NMR (DMSO-$d_6$): δ 2.89 (t, J=7.2 Hz, 2H), 3.86 (t, J=7.2 Hz, 2H), 6.79 (m, 1H), 6.83-6.86 (m, 1H), 6.95-6.98 (m, 3H), 7.10-7.14 (m, 1H), 7.28-7.40 (m, 3H), 11.86 (bs, 1H).

Example 34

Synthesis of 2-(4-(2-fluorophenoxyl)benzyl)-6-hydroxy-1,2,4-triazine-3,5(2H,4H)-dione 6-Bromo-2-(4-(2-fluorophenoxyl)benzyl)-1,2,4-triazine-3,5(2H,4H)-dione (3ae)

Compound 3ae was prepared as described for the preparation of 3a with the exception that 1.0 equiv of 1-(4-(bromomethyl)phenoxy)-2-fluorobenzene was used in one portion in place of sequential addition of 2.5 equivalents of phenethyl iodide. Yield: 47% (white solid). $^1$H NMR (DMSO-d$_6$): δ 5.02 (s, 2H), 6.85 (m, 1H), 7.00 (m, 1H), 7.08 (m, 1H), 7.18-7.26 (m, 3H), 7.33-7.41 (m, 2H), 12.57 (bs, 1H).

6-(Benzyloxy)-2-(4-(2-fluorophenoxyl)benzyl)-1,2,4-triazine-3,5(2H,4H)-dione (4ae)

Compound 4ae was prepared as described for the preparation of 4a except the crude material was used in the next step without further purification.

2-(4-(2-Fluorophenoxyl)benzyl)-6-hydroxy-1,2,4-triazine-3,5(2H,4H)-dione (5ae)

Compound 5ae was prepared as described for the preparation of 5e with the exception that the final compound was purified by prep-HPLC (method: 80-100% acetonitrile-water-0.1% formic acid). Yield: 22% (white solid). Mp 215-219° C.; $^1$H NMR (DMSO-d$_6$): δ 4.84 (s, 2H), 6.83 (dd, J=8.2, 2.4 Hz, 1H), 6.94 (m, 1H), 7.04 (d, J=7.5 Hz, 1H), 7.16-7.28 (m, 3H), 7.31-7.42 (m, 2H), 11.72 (bs, 1H), 12.09 (bs, 1H).

Example 35

Synthesis of 2-(biphenyl-4-ylmethyl)-6-hydroxy-1,2,4-triazine-3,5(2H,4H)-dione

2-(Biphenyl-4-ylmethyl)-6-bromo-1,2,4-triazine-3,5(2H,4H)-dione (3af)

Compound 3af was prepared as described for the preparation of 3a with the exception that 1.5 equiv of 4-(bromomethyl)biphenyl were used in one portion in place of sequential addition of 2.5 equivalents of phenethyl iodide. Yield: 56% (white solid). $^1$H NMR (DMSO-d$_6$): δ 5.07 (s, 2H), 7.35-7.48 (m, 5H), 7.64-7.67 (m, 4H), 12.60 (bs, 1H).

6-(Benzyloxy)-2-(biphenyl-4-ylmethyl)-1,2,4-triazine-3,5(2H,4H)-dione (4af)

Compound 4af was prepared as described for the preparation of 4a. Yield: 12% (white solid). $^1$H NMR (DMSO-d$_6$): δ 4.97 (s, 2H), 5.15 (s, 2H), 7.35-7.43 (m, 8H), 7.48 (m, 2H), 7.62-7.67 (m, 4H), 12.27 (s, 1H).

2-(Biphenyl-4-ylmethyl)-6-hydroxy-1,2,4-triazine-3,5(2H,4H)-dione (5af)

Compound 5af was prepared as described for the preparation of 5e. Yield: 34% (tan solid). Mp>250° C.; $^1$H NMR (DMSO-d$_6$): δ 4.90 (s, 2H), 7.36-7.39 (m, 3H), 7.44-7.48 (m, 2H), 7.62-7.65 (m, 4H), 11.71 (s, 1H), 12.16 (s, 1H).

Example 36

Synthesis of 2-(2,2-Difluoro-2-phenylethyl)-6-hydroxy-1,2,4-triazine-3,5(2H,4H)-dione

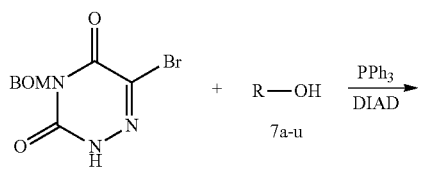

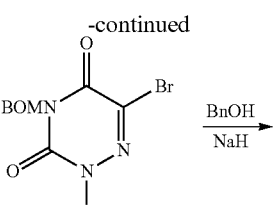

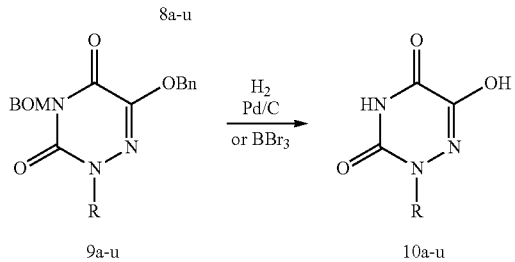

4-(Benzyloxymethyl)-6-bromo-1,2,4-triazine-3,5(2H,4H)-dione (6)

Compound 6 was prepared according to WO 2010/006962.

4-(Benzyloxymethyl)-6-bromo-2-(2,2-difluoro-2-phenylethyl)-1,2,4-triazine-3,5(2H,4H)-dione (8a)

To a 0° C. solution of 4-(benzyloxymethyl)-6-bromo-1,2,4-triazine-3,5(2H,4H)-dione (6, 0.3 g, 0.96 mmol), 2,2-difluoro-2-phenylethanol (7a, 0.17 g, 1.06 mmol, 1.1 equiv), triphenylphosphine (0.30 g, 1.15 mmol, 1.2 equiv) in THF (5 mL) was added dropwise via syringe diisopropyl azodicarboxylate (0.23 mL, 1.15 mmol, 1.2 equiv). The reaction was stirred at 0° C. for 5-10 min, then heated at 66° C. for 7 h. The resulting residue was dissolved in EtOAc and the organic solution was washed with water, dried over Na$_2$SO$_4$ and concentrated to give an oil which was purified by Biotage Isolera One using EtOAc/hexanes to give 0.39 g (95%) of compound 8a as a clear oil. $^1$H NMR (DMSO-d$_6$): δ 4.53 (s, 2H), 4.66 (t, J=13.9 Hz, 2H), 5.30 (s, 2H), 7.27-7.36 (m, 5H), 7.50 (m, 3H), 7.56 (m, 2H).

6-(Benzyloxy)-4-(benzyloxymethyl)-2-(2,2-difluoro-2-phenylethyl)-1,2,4-triazine-3,5(2H,4H)-dione (9a)

To a 0° C. solution of benzyl alcohol (0.044 mL, 0.423 mmol, 1.2 equiv) in DMF (5 mL) was added 60% w/w sodium hydride (0.017 g, 0.423 mmol, 1.2 equiv). The mixture was stirred 5-10 min and a solution of 8a (0.15 g, 0.353 mmol, 1 equiv) in DMF (3 mL) was added via syringe. The reaction was stirred at 0° C. for 5 min and at RT for 2 h. DMF was removed and water was added. The compound was extracted with EtOAc and the organic solution dried over Na$_2$SO$_4$ and concentrated to give an oil which was purified by Biotage Isolera One using EtOAc/hexanes to give 0.10 g (59%) of compound 9a as a clear oil which crystallized overnight under high vac to a white solid. $^1$H NMR (DMSO-d$_6$): δ 4.49 (s, 2H), 4.56 (t, J=12.8 Hz, 2H), 4.83 (s, 2H), 5.27 (s, 2H), 7.26-7.33 (m, 5H), 7.40 (m, 5H), 7.50-7.58 (m, 5H).

2-(2,2-Difluoro-2-phenylethyl)-6-hydroxy-1,2,4-triazine-3,5(2H,4H)-dione (10a)

Compound 9a (0.10 g, 0.208 mmol) was dissolved in a mixture of methanol (3 mL), ethyl acetate (3 mL) and acetic acid (0.2 mL). One spatula tip of 10% Pd/C was added and the mixture was hydrogenated overnight at 1 atm (balloon). The reaction was filtered through celite and the filtrate was concentrated to give a mixture compound 10a and its N-hydroxymethyl analog as beige solid. The mixture was dissolved in methanol and treated with a catalytic amount of sodium carbonate and stirred over weekend. The milky reaction was acidified with 10% $KHSO_4$ solution to pH-4 and the precipitate was filtered, washed thoroughly with water and 10% EtOAc/hexanes to give 20 mg (36%) of product 10a as a white powder. Mp 244-247° C.; $^1H$ NMR (DMSO-$d_6$): δ 4.38 (t, J=14.0 Hz, 2H), 7.50 (m, 5H), 11.88 (m, 1H), 12.17 (m, 1H).

Example 37

Synthesis of 2-(3,4-difluorophenethyl)-6-hydroxy-1,2,4-triazine-3,5(2H,4H)-dione 4-(Benzyloxymethyl)-6-bromo-2-(3,4-difluorophenethyl)-1,2,4-triazine-3,5(2H,4H)-dione (8b)

Compound 8b was prepared as described for the preparation of 8a with the exception that 2-(3,4-difluorophenyl) ethanol was used in place of 2,2-difluoro-2-phenylethanol. Yield: quantitative (white cake). $^1H$ NMR (CDCl$_3$): δ 2.99 (t, J=7.7 Hz, 2H), 4.13 (m, 2H), 4.69 (s, 2H), 5.50 (s, 2H), 6.95 (m, 1H), 7.09 (m, 2H), 7.28-7.35 (m, 5H).

6-(Benzyloxy)-4-(benzyloxymethyl)-2-(3,4-difluorophenethyl)-1,2,4-triazine-3,5(2H,4H)-dione (9b)

Compound 9b was prepared as described for the preparation of 9a. Yield: 53% (yellow solid). $^1H$ NMR (DMSO-$d_6$): δ 2.91 (t, J=7.5 Hz, 2H), 4.06 (t, J=7.5 Hz, 2H), 4.66 (s, 2H), 5.16 (s, 2H), 5.46 (s, 2H), 6.82 (m, 1H), 6.94 (m, 1H), 7.04 (m, 1H), 7.28-7.36 (m, 5H), 7.38-7.46 (m, 5H).

2-(3,4-Difluorophenethyl)-6-hydroxy-1,2,4-triazine-3,5(2H,4H)-dione (10b)

Compound 10b was prepared as described for the preparation of 10a with the exception that Pd(OH)$_2$ was used in place of Pd/C and the hydrogenation was performed overnight at 50 psi in 1:1 mixture of EtOAc and Methanol prior to treatment with sodium carbonate in methanol. Yield: 63% (white solid). Mp 219-220° C., $^1H$ NMR (DMSO-$d_6$): δ 2.91 (t, J=7.2 Hz, 2H), 3.89 (t, J=7.3 Hz, 2H), 7.01 (m, 1H), 7.28-7.36 (m, 2H), 11.67 (s, 1H), 12.02 (s, 1H).

Example 38

Synthesis of 2-(2-(1H-pyrrol-1-yl)ethyl)-6-hydroxy-1,2,4-triazine-3,5(2H,4H)-dione 2-(2-(1H-pyrrol-1-yl)ethyl)-4-(benzyloxymethyl)-6-bromo-1,2,4-triazine-3,5(2H,4H)-dione (8c)

Compound 8c was prepared as described for the preparation of 8a with the exception that 2-(1H-pyrrol-1-yl) ethanol was used in place of 2,2-difluoro-2-phenylethanol and no work-up was required. Yield: 89% (thick oil). $^1H$ NMR (CDCl$_3$): δ 4.25 (m, 4H), 4.65 (s, 2H), 5.47 (s, 2H), 6.14 (t, J=2.1 Hz, 2H), 6.61 (t, J=2.0 Hz, 2H), 7.28-7.35 (m, 5H).

2-(2-(1H-pyrrol-1-yl)ethyl)-6-(benzyloxy)-4-(benzyloxymethyl)-1,2,4-triazine-3,5(2H,4H)-dione (9c)

Compound 9c was prepared as described for the preparation of 9a. Yield: 47% (yellow solid).

2-(2-(1H-pyrrol-1-yl)ethyl)-6-hydroxy-1,2,4-triazine-3,5(2H,4H)-dione (10c)

Compound 9c (0.13 g, 0.303 mmol) was dissolved in dichloromethane (5 mL) and a 1.0 M solution of boron tribromide (0.91 mL, 0.909 mmol, 3.0 equiv)) was added. The reaction was stirred at rt for 2.5 h and an extra equivalent of boron tribromide was added. After additional stirring for 1.5 h, the reaction was quenched with water and the volume of the mixture was reduced to small amount. The resulting mixture was partitioned between EtOAc and water and the organic phase was washed with brine, dried (Na$_2$SO$_4$) and concentrated. The residual oil was subjected to purification by prepatory HPLC (method: 5-30% acetonitrile-water-0.1% formic acid) to give 4.8 mg (7.1%) of compound 10c as a pink solid. Mp 239-241° C.; $^1H$ NMR (DMSO-$d_6$): δ 3.92 (t, J=6.3 Hz, 2H), 4.13 (t, J=6.3 Hz, 2H), 5.95 (t, J=2.1 Hz, 2H), 6.67 (t, J=2.1 Hz, 2H), 11.86 (bs, 2H).

Example 39

Synthesis of 2-(2-(1H-pyrazol-1-yl)ethyl)-6-hydroxy-1,2,4-triazine-3,5(2H,4H)-dione 2-(2-(1H-pyrazol-1-yl)ethyl)-4-(benzyloxymethyl)-6-bromo-1,2,4-triazine-3,5(2H,4H)-dione (8d)

Compound 8d was prepared as described for the preparation of 8a with the exception that 2-(1H-pyrazol-1-yl) ethanol was used in place of 2,2-difluoro-2-phenylethanol and no work-up was required. Yield: 86% (clear oil). $^1H$ NMR (CDCl$_3$): δ 4.36 (t, J=5.9 Hz, 2H), 4.50 (t, J=5.9 Hz, 2H), 4.67 (s, 2H), 5.47 (s, 2H), 6.24 (t, J=2.1 Hz, 1H), 7.29-7.34 (m, 5H), 7.36 (m, 1H), 7.46 (m, 1H).

2-(2-(1H-pyrazol-1-yl)ethyl)-6-(benzyloxy)-4-(benzyloxymethyl)-1,2,4-triazine-3,5(2H,4H)-dione (9d)

Compound 9d was prepared as described for the preparation of 9a with the exception that 1.5 equivalents of sodium hydride and benzyl alcohol were used. Yield: 47% (clear oil). $^1H$ NMR (CDCl$_3$): δ 4.27 (t, J=5.9 Hz, 2H), 4.43 (t, J=5.9 Hz, 2H), 4.67 (s, 2H), 5.05 (s, 2H), 5.46 (s, 2H), 6.21 (t, J=2.1 Hz, 1H), 7.20 (m, 1H), 7.28-7.41 (m, 10H), 7.51 (m, 1H).

2-(2-(1H-pyrazol-1-yl)ethyl)-6-hydroxy-1,2,4-triazine-3,5(2H,4H)-dione (10d)

Compound 9d (0.14 g, 0.323 mmol) was dissolved in methanol (5 mL) and one spatula tip of 10% Pd/C was added. The mixture was hydrogenated overnight at 1 atm (balloon) and filtered through celite. The filtrate was concentrated to give 60 mg (83%) of compound 10d as a white solid. Mp>275° C. (decomp); $^1H$ NMR (DMSO-$d_6$): δ 4.01 (t, J=6.2 Hz, 2H), 4.36 (t, J=6.2 Hz, 2H), 6.20 (t, J=2.1 Hz, 1H), 7.40 (d, J=1.5 Hz, 1H), 7.69 (d, J=2.0 Hz, 1H), 11.69 (s, 1H), 12.04 (s, 1H).

Example 40

Synthesis of 2-(2-(1H-indol-1-yl)ethyl)-6-hydroxy-1,2,4-triazine-3,5(2H,4H)-dione

2-(2-(1H-indol-1-yl)ethyl)-4-(benzyloxymethyl)-6-bromo-1,2,4-triazine-3,5(2H,4H)-dione (8e)

Compound 8e was prepared as described for the preparation of 8a with the exception that 2-(1H-indol-1-yl)ethanol was used in place of 2,2-difluoro-2-phenylethanol and no work-up was required. Yield: 84% (off white cake). $^1$H NMR (CDCl$_3$): δ 4.33 (t, J=6.4 Hz, 2H), 4.49 (t, J=6.4 Hz, 2H), 4.57 (s, 2H), 5.38 (s, 2H), 6.53 (dd, J=0.8, 3.3 Hz, 1H), 7.07 (d, J=3.0 Hz, 1H), 7.09-7.11 (m, 1H), 7.18 (m, 1H), 7.28-7.36 (m, 5H), 7.59 (dt, J=7.6, 1.0 Hz, 1H).

2-(2-(1H-indol-1-yl)ethyl)-6-(benzyloxy)-4-(benzyloxymethyl)-1,2,4-triazine-3,5(2H,4H)-dione (9e)

Compound 9e was prepared as described for the preparation of 9a with the exception that the reaction was stirred overnight at rt. Yield: 51% (white cake). $^1$H NMR (CDCl$_3$): δ 4.20 (t, J=6.1 Hz, 2H), 4.42 (t, J=6.1 Hz, 2H), 4.59 (s, 2H), 4.67 (s, 2H), 5.40 (s, 2H), 6.48 (d, J=3.0 Hz, 1H), 6.94 (d, J=3.0 Hz, 1H), 7.07 (m, 1H), 7.15 (m, 1H), 7.18 (m, 1H), 7.25-7.37 (m, 10H), 7.57 (d, J=7.8, 1.0 Hz).

2-(2-(1H-indol-1-yl)ethyl)-6-hydroxy-1,2,4-triazine-3,5(2H,4H)-dione (10e)

Compound 10e was prepared as described for the preparation of 10a with the exception that Pd(OH)$_2$ was used in place of Pd/C, EtOAc and methanol were used as cosolvents and the hydrogenation was performed overnight at 50 psi. After filtering through celite, the residue was subjected to purification by prep-HPLC (method: 5-30% acetonitrile-water-0.1% formic acid) to give compound 10e (3.3%). $^1$H NMR (MeOD): δ 4.07 (t, J=6.1 Hz, 2H), 4.48 (t, J=6.2 Hz, 2H), 6.40 (d, J=3.0 Hz, 1H), 6.98 (t, J=7.6 Hz, 1H), 7.10 (t, J=7.6 Hz, 1H), 7.14 (d, J=3.3 Hz, 1H), 7.38 (d, J=8.3 Hz, 1H), 7.48 (d, J=7.8, 1.0H).

Example 41

Synthesis of 2-(2-(1H-benzo[d]imidazol-1-yl)ethyl)-6-hydroxy-1,2,4-triazine-3,5(2H,4H)-dione

2-(2-(1H-benzo[d]imidazol-1-yl)ethyl)-4-(benzyloxymethyl)-6-bromo-1,2,4-triazine-3,5(2H,4H)-dione (8f)

Compound 8f was prepared as described for the preparation of 8a with the exception that 2-(1H-benzo[d]imidazol-1-yl)ethanol was used in place of 2,2-difluoro-2-phenylethanol and no work-up was required. The pure compound was obtained from triturating the solid residue in EtOAc-hexanes. Yield: 72% (beige solid). $^1$H NMR (CDCl$_3$): δ 4.38 (t, J=6.6 Hz, 2H), 4.56 (t, J=6.4 Hz, 2H), 4.61 (s, 2H), 5.42 (s, 2H), 7.28-7.34 (m, 7H), 7.39 (m, 1H), 7.80 (m, 1H), 7.91 (s, 1H).

2-(2-(1H-benzo[d]imidazol-1-yl)ethyl)-6-(benzyloxy)-4-(benzyloxymethyl)-1,2,4-triazine-3,5(2H,4H)-dione (9f)

Compound 9f was prepared as described for the preparation of 9a with the exception that the reaction was stirred overnight at rt and the compound was purified by flash chromatography (eluent: pure EtOAc, 1% NH$_4$OH). Yield: 34% (white solid). $^1$H NMR (CDCl$_3$): δ 4.25 (t, J=5.9 Hz, 2H), 4.47 (t, J=5.9 Hz, 2H), 4.60 (s, 2H), 4.75 (s, 2H), 5.40 (s, 2H), 7.27-7.36 (m, 13H), 7.71 (s, 1H), 7.78 (m, 1H).

2-(2-(1H-benzo[d]imidazol-1-yl)ethyl)-6-hydroxy-1,2,4-triazine-3,5(2H,4H)-dione (10f)

Compound 10f was prepared as described for the preparation of 10d. Yield: 18% (beige solid). Mp>260° C. (decomp); $^1$H NMR (DMSO-d$_6$): δ 3.99 (t, J=5.8 Hz, 2H), 4.50 (t, J=5.8 Hz, 2H), 7.18 (m, 1H), 7.23 (m, 1H), 7.51 (d, J=7.6 Hz, 1H), 7.61 (d, J=7.3 Hz, 1H), 8.14 (s, 1H).

Example 42

Synthesis of 2-(2-(1H-pyrrolo[2,3-b]pyridin-1-yl)ethyl)-6-hydroxy-1,2,4-triazine-3,5(2H,4H)-dione

2-(2-(1H-pyrrolo[2,3-b]pyridin-1-yl)ethyl)-4-(benzyloxymethyl)-6-bromo-1,2,4-triazine-3,5(2H,4H)-dione (8g)

Compound 8g was prepared as described for the preparation of 8a with the exception that 2-(1H-pyrrolo[2,3-b]pyridin-1-yl)ethanol was used in place of 2,2-difluoro-2-phenylethanol and no work-up was required. Yield: quantitative (white cake). $^1$H NMR (CDCl$_3$): δ 4.36 (t, J=5.4 Hz, 2H), 4.67 (t, J=5.6 Hz, 2H), 4.68 (s, 2H), 5.44 (s, 2H), 6.49 (d, J=3.5 Hz, 1H), 6.99 (dd, J=4.8, 7.8 Hz, 1H), 7.17 (d, J=3.5 Hz, 1H), 7.30-7.37 (m, 5H), 7.86 (dd, J=1.5, 7.8 Hz, 1H), 8.11 (dd, J=1.5, 4.8 Hz, 1H).

2-(2-(1H-pyrrolo[2,3-b]pyridin-1-yl)ethyl)-6-(benzyloxy)-4-(benzyloxymethyl)-1,2,4-triazine-3,5(2H,4H)-dione (9g)

Compound 9g was prepared as described for the preparation of 9a with the exception that the compound was purified by recrystallization in EtOAc-hexanes. Yield: 32% (white solid). $^1$H NMR (CDCl$_3$): δ 4.28 (t, J=5.4 Hz, 2H), 4.52 (s, 2H), 4.63 (t, J=5.4 Hz, 2H), 4.66 (s, 2H), 5.43 (s, 2H), 6.42 (d, J=3.3 Hz, 1H), 7.03 (m, 2H), 7.21-7.36 (m, 10H), 7.84 (d, J=7.8, 1.0 Hz), 8.22 (d, J=4.6 Hz, 1H).

2-(2-(1H-pyrrolo[2,3-b]pyridin-1-yl)ethyl)-6-hydroxy-1,2,4-triazine-3,5(2H,4H)-dione (10g)

Compound 10g was prepared as described for the preparation of 10c with the exception that 4.0 equivalents of boron tribromide were added in one portion and the reaction time was 2 h. The desired product was water soluble, thus at the end of the reaction, water was added and the reaction mixture was concentrated. The resulting residue was purified by prep-HPLC (method: 5-30% acetonitrile-water-0.1% formic acid). Yield: 79% (beige solid). Mp 258-260° C.; $^1$H NMR (DMSO-d$_6$): δ 4.03 (t, J=5.3 Hz, 2H), 4.51 (t, J=5.2 Hz, 2H), 6.43 (d, J=3.3 Hz, 1H), 7.04 (dd, J=4.8, 7.6 Hz, 1H), 7.46 (d, J=3.3 Hz, 1H), 7.92 (d, J=7.8 Hz, 1H), 8.16 (d, J=4.3 Hz, 1H), 11.88 (bs, 2H).

Example 43

Synthesis of 2-(2-(1H-indazol-1-yl)ethyl)-6-hydroxy-1,2,4-triazine-3,5(2H,4H)-dione

2-(2-(1H-indazol-1-yl)ethyl)-4-(benzyloxymethyl)-6-bromo-1,2,4-triazine-3,5(2H,4H)-dione (8h)

Compound 8h was prepared as described for the preparation of 8a with the exception that 2-(1H-indazol-1-yl)

ethanol was used in place of 2,2-difluoro-2-phenylethanol and the compound was obtained from triturating the light yellow oil in methanol. Yield: 71% (white solid). $^1$H NMR (CDCl$_3$): δ 4.41 (t, J=5.8 Hz, 2H), 4.59 (s, 2H), 4.76 (t, J=5.9 Hz, 2H), 5.39 (s, 2H), 7.13 (m, 1H), 7.28-7.36 (m, 7H), 7.69 (dt, J=8.1, 1.0 Hz, 1H), 7.99 (s, 1H).

2-(2-(1H-indazol-1-yl)ethyl)-6-(benzyloxy)-4-(benzyloxymethyl)-1,2,4-triazine-3,5(2H,4H)-dione (9h)

Compound 9h was prepared as described for the preparation of 9a with the exception that a total of 2.25 equivalents of sodium hydride and benzyl alcohol were used. Yield: 23% (white solid).

2-(2-(1H-indazol-1-yl)ethyl)-6-hydroxy-1,2,4-triazine-3,5(2H,4H)-dione (10h)

Compound 10h was prepared as described for the preparation of 10c with the exception that a total of 6 equivalents of boron tribromide were used and acetonitrile was used as a cosolvent with dichloromethane due to poor solubility of the starting material in dichloromethane alone. At the end of the reaction, water was added and the reaction mixture was concentrated. The desired product was obtained by triturating the resulting residue in methanol-water. Yield: 66% (light tan solid). Mp>260° C. (decomp); $^1$H NMR (DMSO-d$_6$): δ 4.05 (t, J=5.8 Hz, 2H), 4.67 (t, J=5.8 Hz, 2H), 7.11 (t, J=7.6 Hz, 1H), 7.36 (t, J=7.6 Hz, 1H), 7.50 (t, J=8.6 Hz, 1H), 7.73 (t, J=8.3 Hz, 1H), 8.04 (s, 1H), 11.64 (s, 1H), 11.98 (s, 1H).).

Example 44

Synthesis of 2-(2-(9H-carbazol-9-yl)ethyl)-6-hydroxy-1,2,4-triazine-3,5(2H,4H)-dione 2-(2-(9H-carbazol-9-yl)ethyl)-4-(benzyloxymethyl)-6-bromo-1,2,4-triazine-3,5(2H,4H)-dione (8i)

Compound 8i was prepared as described for the preparation of 8a with the exception that 2-(9H-carbazol-9-yl)ethanol was used in place of 2,2-difluoro-2-phenylethanol and the compound was obtained from triturating the solid residue in EtOAc-dichloromethane. Yield: 62% (white solid). $^1$H NMR (DMSO-d$_6$): δ 4.30 (m, 2H), 4.39 (s, 2H), 4.73 (m, 2H), 5.18 (s, 2H), 7.17 (t, J=7.3 Hz, 2H), 7.26 (m, 2H), 7.29-7.40 (m, 5H), 7.48 (d, J=8.1 Hz, 2H), 8.10 (t, J=7.8 Hz, 2H).

2-(2-(9H-carbazol-9-yl)ethyl)-6-(benzyloxy)-4-(benzyloxymethyl)-1,2,4-triazine-3,5(2H,4H)-dione (9i)

Compound 9i was prepared as described for the preparation of 9a with the exception that 2.0 equivalents of sodium hydride and benzyl alcohol were used in one portion and the reaction mixture was stirred overnight at rt. Yield: 23% (viscous oil). $^1$H NMR (CDCl$_3$): δ 4.23 (t, J=5.8 Hz, 2H), 4.37 (s, 2H), 4.56 (s, 2H), 4.62 (t, J=6.0 Hz, 2H), 5.35 (s, 2H), 7.08 (m, 2H), 7.19-7.39 (m, 14H), 8.03 (d, J=7.8 Hz, 2H).

2-(2-(9H-carbazol-9-yl)ethyl)-6-hydroxy-1,2,4-triazine-3,5(2H,4H)-dione (10i)

Compound 10i was prepared as described for the preparation of 10c with the exception that a total of 8 equivalents of boron tribromide were used. After workup, the residual oil was subjected to purification by prepatory HPLC (method: 20-70% acetonitrile-water-0.1% formic acid) to give 4.0 mg (9.2%) of compound 10i as an off-white solid.

Example 45

Synthesis of 6-hydroxy-2-(2-morpholinoethyl)-1,2,4-triazine-3,5(2H,4H)-dione 4-(Benzyloxymethyl)-6-bromo-2-(2-morpholinoethyl)-1,2,4-triazine-3,5(2H,4H)-dione (8j)

Compound 8j was prepared as described for the preparation of 8a with the exception that 2-morpholinoethanol was used in place of 2,2-difluoro-2-phenylethanol. Yield: 82% (light yellow oil). $^1$H NMR (CDCl$_3$): δ 2.51 (m, 4H), 2.69 (t, J=6.3 Hz, 2H), 3.66 (t, J=4.7 Hz, 4H), 4.09 (t, J=6.3 Hz, 2H), 4.72 (s, 2H), 5.52 (s, 2H), 7.30-7.36 (m, 5H).

6-(Benzyloxy)-4-(benzyloxymethyl)-2-(2-morpholinoethyl)-1,2,4-triazine-3,5(2H,4H)-dione (9j)

Compound 9j was prepared as described for the preparation of 9a with the exception that 8j was used in place of 8a. Yield: 44% (oil). $^1$H NMR (CDCl$_3$): δ 2.45 (m, 4H), 2.59 (t, J=6.4 Hz, 2H), 3.64 (t, J=4.6 Hz, 4H), 3.98 (t, J=6.4 Hz, 2H), 4.71 (s, 2H), 5.22 (s, 2H), 5.52 (s, 2H), 7.28-7.45 (m, 10H).

6-Hydroxy-2-(2-morpholinoethyl)-1,2,4-triazine-3,5(2H,4H)-dione (10j)

Compound 10j was prepared as described for the preparation of 10a with the exception that Pd(OH)$_2$ was used in place of Pd/C, EtOAc and methanol were used as cosolvents and the hydrogenation was performed overnight at 50 psi in the presence of a catalytic amount of sodium carbonate. After filtering through celite, the residue was dissolved in a minimum amount of formic acid and subjected to purification by prep-HPLC (method: 0-20% acetonitrile-water-0.1% formic acid) to give compound 10j (15%, white solid). Mp 146-148° C.; $^1$H NMR (DMSO-d$_6$): δ 2.40 (m, 4H), 2.53 (t, J=6.7 Hz, 2H), 3.53 (t, J=4.4 Hz, 4H), 3.77 (t, J=6.7 Hz, 2H), 11.70 (bs, 1H), 12.03 (bs, 1H).

Example 46

Synthesis of 6-hydroxy-2-(1-phenylpropan-2-yl)-1,2,4-triazine-3,5(2H,4H)-dione 4-(Benzyloxymethyl)-6-bromo-2-(1-phenylpropan-2-yl)-1,2,4-triazine-3,5(2H,4H)-dione (8k)

Compound 8k was prepared as described for the preparation of 8a with the exception that 1-phenylpropan-2-ol was used in place of 2,2-difluoro-2-phenylethanol. Yield: 74% (clear thick oil). $^1$H NMR (CDCl$_3$): δ 1.37 (d, J=6.6 Hz, 3H), 2.93 (dd, J=6.6, 13.6 Hz, 1H), 3.04 (dd, J=8.6, 13.6 Hz, 1H), 4.54 (s, 2H), 5.06 (m, 1H), 5.41 (s, 2H), 7.15 (m, 3H), 7.25 (m, 2H), 7.28-7.33 (m, 5H).

6-(Benzyloxy)-4-(benzyloxymethyl)-2-(1-phenylpropan-2-yl)-1,2,4-triazine-3,5(2H,4H)-dione (9k)

Compound 9k was prepared as described for the preparation of 9a. Yield: 53%. $^1$H NMR (CDCl$_3$): δ 1.28 (d, J=6.6 Hz, 3H), 2.76-2.89 (m, 2H), 4.49 (s, 2H), 5.04 (m, 1H), 5.29

(s, 2H), 5.37 (s, 2H), 6.94 (m, 2H), 7.11 (m, 1H), 7.18 (m, 2H), 7.29 (m, 4H), 7.35-7.43 (m, 4H), 7.48 (m, 2H).

6-Hydroxy-2-(1-phenylpropan-2-yl)-1,2,4-triazine-3,5(2H,4H)-dione (10k)

Compound 10k was prepared as described for the preparation of 10c with the exception that 4.0 equivalents of boron tribromide were added in one portion and the reaction time was 45 min. The compound was purified by trituration in EtOAc and hexanes. Yield: 33% (white powder). Mp 222-224° C.; $^1$H NMR (DMSO-d$_6$): δ 1.21 (d, J=6.6 Hz, 3H), 2.81 (dd, J=6.3, 13.6 Hz, 1H), 2.92 (dd, J=8.6, 13.4 Hz, 1H), 4.78 (m, 1H), 7.12-7.18 (m, 3H), 7.25 (m, 2H), 11.64 (s, 1H), 11.90 (s, 1H).

Example 47

Synthesis of 6-hydroxy-2-(2-(pyridin-2-yl)ethyl)-1,2,4-triazine-3,5(2H,4H)-dione 4-(Benzyloxymethyl)-6-bromo-2-(2-(pyridin-2-yl)ethyl)-1,2,4-triazine-3,5(2H,4H)-dione (8l)

Compound 8l was prepared as described for the preparation of 8a with the exception that 2-(2-iodoethyl)pyridine was used in place of 2,2-difluoro-2-phenylethanol and no work-up was required. Yield: 85% (clear oil). $^1$H NMR (CDCl$_3$): δ 3.22 (t, J=7.1 Hz, 2H), 4.37 (t, J=7.6 Hz, 2H), 4.68 (s, 2H), 5.49 (s, 2H), 7.12-7.19 (m, 2H), 7.29-7.34 (mt, 5H), 7.61 (dt, J=2.0, 7.8 Hz, 1H), 8.51 (d, J=4.8 Hz, 1H).

6-(Benzyloxy)-4-(benzyloxymethyl)-2-(2-(pyridin-2-yl)ethyl)-1,2,4-triazine-3,5(2H,4H)-dione (9l)

Compound 9l was prepared as described for the preparation of 9a with the exception that the reaction was stirred for 30 min at 0° C. Yield: 50%. $^1$H NMR (CDCl$_3$): δ 3.17 (t, J=7.1 Hz, 2H) 4.27 (t, J=5.6 Hz, 2H), 4.67 (s, 2H), 5.07 (s, 2H), 5.47 (s, 2H), 7.12 (m, 2H), 7.29-7.42 (m, 10H), 7.59 (dt, J=2.0, 7.8 Hz, 1H), 8.54 (d, J=5.1 Hz, 1H).

6-Hydroxy-2-(2-(pyridin-2-yl)ethyl)-1,2,4-triazine-3,5(2H,4H)-dione (10l)

Compound 10l was prepared as described for the preparation of 10c with the exception that 2.0 equivalents of boron tribromide were added in one portion and the reaction time was 45 min. The compound was subjected to purification by prepatory HPLC (method: 0-20% acetonitrile-water-0.1% formic acid) to give 10l as a white solid. Yield: 18%. Mp 224-226° C.; $^1$H NMR (DMSO-d$_6$): δ 3.17 (t, J=5.8 Hz, 2H), 4.04 (t, J=6.8 Hz, 2H), 7.59 (m, 2H), 8.07 (m, 1H), 8.63 (m, 1H), 11.64 (bs, 1H), 12.04 (s, 1H).

Example 48

Synthesis of 6-hydroxy-2-(perfluorophenethyl)-1,2,4-triazine-3,5(2H,4H)-dione 4-(Benzyloxymethyl)-6-bromo-2-(perfluorophenyl)ethyl-1,2,4-triazine-3,5(2H,4H)-dione (8m)

Compound 8m was prepared as described for the preparation of 8a with the exception that 1,2,3,4,5-pentafluoro-6-(2-iodoethyl)benzene was used in place of 2,2-difluoro-2-phenylethanol and no work-up was required. Yield: quantitative (clear oil). $^1$H NMR (CDCl$_3$): δ 3.16 (t, J=6.6 Hz, 2H), 4.20 (t, J=6.6 Hz, 2H), 4.68 (s, 2H), 5.50 (s, 2H), 7.30-7.35 (m, 5H).

6-(Benzyloxy)-4-(benzyloxymethyl)-2-(perfluorophenyl)ethyl-1,2,4-triazine-3,5(2H,4H)-dione (9m)

Compound 9m was prepared as described for the preparation of 9a with the exception that the reaction was stirred for 30 min at 0° C. Yield: 48% (clear oil). $^1$H NMR (CDCl$_3$): δ 3.07 (t, J=7.1 Hz, 2H) 4.07 (t, J=6.8 Hz, 2H), 4.66 (s, 2H), 5.14 (s, 2H), 5.46 (s, 2H), 7.29-7.40 (m, 10H).

6-Hydroxy-2-(perfluorophenyl)ethyl-1,2,4-triazine-3,5(2H,4H)-dione (10m)

Compound 10m was prepared as described for the preparation of 10d with the exception that the hydrogenation was performed over weekend and the compound was purified by prep-HPLC (method: 20-70% acetonitrile-water-0.1% formic acid). Yield: 61% (beige solid). $^1$H NMR (DMSO-d$_6$): δ 3.03 (t, J=6.6 Hz, 2H), 3.90 (t, J=6.6 Hz, 2H), 11.71 (s, 1H), 12.09 (s, 1H).

Example 49

Synthesis of 6-hydroxy-2-(((1R,2R)-2-phenylcyclopropyl)methyl)-1,2,4-triazine-3,5(2H,4H)-dione 4-(Benzyloxymethyl)-6-bromo-2-(((1R,2R)-2-phenylcyclopropyl)methyl)-1,2,4-triazine-3,5(2H,4H)-dione (8n)

Compound 8n was prepared as described for the preparation of 8a with the exception that ((1R,2R)-2-phenylcyclopropyl)methanol was used in place of 2,2-difluoro-2-phenylethanol and no work-up was required. Yield: 73% (clear oil). $^1$H NMR (CDCl$_3$): δ 1.02-1.11 (m, 2H), 1.58 (m, 1H), 2.05 (m, 1H), 3.92 (dd, J=7.6, 13.9 Hz, 1H), 4.03 (dd, J=6.8, 13.9 Hz, 1H), 4.70 (s, 2H), 5.51 (s, 2H), 7.04 (m, 2H), 7.16 (m, 1H), 7.24-7.35 (m, 7H).

6-(Benzyloxy)-4-(benzyloxymethyl)-2-(((1R,2R)-2-phenylcyclopropyl)methyl)-1,2,4-triazine-3,5(2H,4H)-dione (9n)

Compound 9n was prepared as described for the preparation of 9a with the exception that the reaction was stirred for 30 min at 0° C. Yield: 58% (clear oil). $^1$H NMR (CDCl$_3$): δ 0.95 (m, 1H), 1.03 (m, 1H), 1.51 (m, 1H), 1.97 (m, 1H), 3.83 (dd, J=7.3, 13.9 Hz, 1H), 3.91 (dd, J=6.8, 13.9 Hz, 1H), 4.70 (s, 2H), 5.19 (s, 2H), 5.49 (s, 2H), 6.99 (m, 2H), 7.16 (m, 1H), 7.23-7.40 (m, 12H).

6-Hydroxy-2-(((1R,2R)-2-phenylcyclopropyl)methyl)-1,2,4-triazine-3,5(2H,4H)-dione (10n)

Compound 10n was prepared as described for the preparation of 10c with the exception that 4.0 equivalents of boron tribromide were added in one portion and the reaction time was 30 min. The compound was recrystallized in EtOAc-hexanes mixture. Yield: 17% (white solid). Mp 142-145° C.; $^1$H NMR (DMSO-d$_6$): δ 0.96 (m, 1H), 1.01 (m, 1H), 1.39 (m, 1H), 1.96 (m, 1H), 3.70 (dd, J=2.0, 6.8 Hz, 2H), 7.03 (m, 2H), 7.12 (m, 1H), 7.23 (m, 2H), 11.63 (s, 1H), 12.09 (s, 1H).

Example 50

Synthesis of 2-((1H-indol-4-yl)methyl)-6-hydroxy-1,2,4-triazine-3,5(2H,4H)-dione tert-Butyl 4-((4-(benzyloxymethyl)-6-bromo-3,5-dioxo-4,5-dihydro-1,2,4-triazin-2(3H)-yl)methyl)-1H-indole-1-carboxylate (8o)

Compound 8o was prepared as described for the preparation of 8a with the exception that tert-butyl 4-(hydroxymethyl)-1H-indole-1-carboxylate was used in place of 2,2-difluoro-2-phenylethanol and no work-up was required. Yield: 56% (white solid foam). $^1$H NMR (CDCl$_3$): δ 1.68 (s, 9H), 4.67 (s, 2H), 5.33 (s, 2H), 5.49 (s, 2H), 6.86 (d, J=3.5 Hz, 1H), 7.24 (m, 3H), 7.29-7.33 (m, 4H), 7.65 (d, J=3.8 Hz, 1H), 8.19 (m, 1H).

tert-Butyl 4-((6-(benzyloxy)-4-(benzyloxymethyl)-3,5-dioxo-4,5-dihydro-1,2,4-triazin-2(3H)-yl)methyl)-1H-indole-1-carboxylate (9o)

Compound 9o was prepared as described for the preparation of 9a with the exception that the reaction was stirred for 30 min at 0° C. Yield: 36% (clear viscous oil). $^1$H NMR (CDCl$_3$): δ 1.67 (s, 9H), 4.68 (s, 2H), 5.14 (s, 2H), 5.23 (s, 2H), 5.49 (s, 2H), 6.81 (d, J=4.3 Hz, 1H), 7.23 (m, 3H), 7.29-7.33 (m, 4H), 7.37 (m, 5H), 7.60 (d, J=3.8 Hz, 1H), 8.16 (d, J=7.6 Hz, 1H).

2-((1H-indol-4-yl)methyl)-6-hydroxy-1,2,4-triazine-3,5(2H,4H)-dione (10o)

Compound 9o (0.17 g, 0.30 mmol) was stirred in a 1:1 TFA-dichloromethane mixture (4 mL) for 1 h. The reaction was concentrated and excess of TFA was co-evaporated three times with dichloromethane. The resulting residue was then treated with a 1.0M solution of boron tribromide in dichloromethane (1.5 mL, 1.5 mmol, 5 equiv) for 1.5 h. Solvent was removed and the residue was purified by prep-HPLC (method: 5-30% acetonitrile-water-0.1% formic acid) to give compound 10o (36%) as a purple solid. Mp 208-210° C.; $^1$H NMR (DMSO-d$_6$): δ 5.09 (s, 2H), 6.52 (s, 1H), 6.87 (d, J=7.1 Hz, 1H), 7.04 (t, J=8.1 Hz, 1H), 7.34 (m, 2H), 11.19 (s, 1H), 11.61 (bs, 1H), 12.17 (s, 1H).

Example 51

Synthesis of 6-hydroxy-2-(isoquinolin-5-ylmethyl)-1,2,4-triazine-3,5(2H,4H)-dione 4-(Benzyloxymethyl)-6-bromo-2-(isoquinolin-5-ylmethyl)-1,2,4-triazine-3,5(2H,4H)-dione (8p)

Compound 8p was prepared as described for the preparation of 8a with the exception that isoquinolin-5-ylmethanol was used in place of 2,2-difluoro-2-phenylethanol and no work-up was required. Yield: 75% (white solid cake). $^1$H NMR (CDCl$_3$): δ 4.68 (s, 2H), 5.51 (s, 4H), 7.20 (m, 3H), 7.28 (m, 2H), 7.63 (t, J=8.1 Hz, 1H), 7.84 (d, J=7.3 Hz, 1H), 8.01 (d, J=8.1 Hz, 1H), 8.06 (d, J=5.8 Hz, 1H), 8.63 (d, J=6.1 Hz, 1H), 9.30 (s, 1H).

6-(Benzyloxy)-4-(benzyloxymethyl)-2-(isoquinolin-5-ylmethyl)-1,2,4-triazine-3,5(2H,4H)-dione (9p)

Compound 9p was prepared as described for the preparation of 9a with the exception that the reaction was stirred for 30 min at 0° C. Yield: 62% (colorless viscous oil). $^1$H NMR (CDCl$_3$): δ 4.69 (s, 2H), 5.11 (s, 2H), 5.41 (s, 2H), 5.51 (s, 2H), 7.21 (m, 3H), 7.29-7.32 (m, 8H), 7.59 (dd, J=7.3, 8.1 Hz, 1H), 7.74 (d, J=7.1 Hz, 1H), 7.99 (d, J=8.3 Hz, 1H), 8.05 (d, J=6.1 Hz, 1H), 8.57 (d, J=6.1 Hz, 1H), 9.30 (s, 1H).

6-Hydroxy-2-(isoquinolin-5-ylmethyl)-1,2,4-triazine-3,5(2H,4H)-dione (10p)

Compound 10p was prepared as described for the preparation of 10c with the exception that 4.0 equivalents of boron tribromide were added in one portion and the reaction time was 1h. The compound was subjected to purification by prepatory HPLC (method: 0-20% acetonitrile-water-0.1% formic acid) to give 24% of compound 10p as a yellow solid. Mp>250° C. (decomp); $^1$H NMR (DMSO-d$_6$): δ 5.32 (s, 2H), 7.66 (m, 2H), 8.08 (m, 2H), 8.56 (s, 1H), 9.35 (s, 1H), 11.71 (s, 1H), 12.20 (s, 1H).

Example 52

Synthesis of 2-(benzo[b]thiophen-4-ylmethyl)-6-hydroxy-1,2,4-triazine-3,5(2H,4H)-dione 2-(Benzo[b]thiophen-7-ylmethyl)-4-(benzyloxymethyl)-6-bromo-1,2,4-triazine-3,5(2H,4H)-dione (8q)

Compound 8q was prepared as described for the preparation of 8a with the exception that benzo[b]thiophen-7-ylmethanol was used in place of 2,2-difluoro-2-phenylethanol and no work-up was required. Yield: 87%. $^1$H NMR (CDCl$_3$): δ 4.69 (s, 2H), 5.37 (s, 2H), 5.52 (s, 2H), 7.24 (m, 2H), 7.30 (m, 2H), 7.40 (m, 4H), 7.47 (m, 1H), 7.84 (t, J=4.6 Hz, 1H).

2-(Benzo[b]thiophen-7-ylmethyl)-6-(benzyloxy)-4-(benzyloxymethyl)-1,2,4-triazine-3,5(2H,4H)-dione (9q)

Compound 9q was prepared as described for the preparation of 9a with the exception that the reaction was stirred for 30 min at 0° C. Yield: 67% (colorless viscous oil). $^1$H NMR (CDCl$_3$): δ 4.71 (s, 2H), 5.15 (s, 2H), 5.27 (s, 2H), 5.51 (s, 2H), 7.22 (m, 2H), 7.29-7.34 (m, 7H), 7.38 (m, 5H), 7.82 (dd, J=1.8, 6.8 Hz, 1H).

2-(Benzo[b]thiophen-7-ylmethyl)-6-hydroxy-1,2,4-triazine-3,5(2H,4H)-dione (10q)

Compound 10q was prepared as described for the preparation of 10c with the exception that 4.0 equivalents of boron tribromide were added in one portion and the reaction time was 1h. The compound was subjected to purification by prepatory HPLC (method: 20-70% acetonitrile-water-0.1% formic acid) to give 3.4% of compound 10q as a solid. Mp 256-260° C.; $^1$H NMR (DMSO-d$_6$): δ 5.12 (s, 2H), 7.29 (d, J=7.2 Hz, 1H), 7.39 (t, J=7.6 Hz, 1H), 7.50 (d, J=5.3 Hz, 1H), 7.77 (d, J=5.3 Hz, 1H), 7.83 (d, J=7.8 Hz, 1H), 11.71 (bs, 1H), 12.23 (s, 1H).

Example 53

Synthesis of 2-(3,5-difluorophenethyl)-6-hydroxy-1,2,4-triazine-3,5(2H,4H)-dione 4-(Benzyloxymethyl)-6-bromo-2-(3,5-difluorophenethyl)-1,2,4-triazine-3,5(2H,4H)-dione (8r)

Compound 8r was prepared as described for the preparation of 8a with the exception that 2-(3,5-difluorophenyl)

ethanol was used in place of 2,2-difluoro-2-phenylethanol and no work-up was required. Yield: 76% (white solid cake). $^1$H NMR (CDCl$_3$): δ 3.04 (t, J=7.6 Hz, 2H), 4.16 (m, 2H), 4.69 (s, 2H), 5.51 (s, 2H), 6.70 (m, 1H), 6.78 (m, 2H), 7.31 (m, 1H), 7.34 (m, 4H).

6-(Benzyloxy)-4-(benzyloxymethyl)-2-(3,5-difluorophenethyl)-1,2,4-triazine-3,5(2H,4H)-dione (9r)

Compound 9r was prepared as described for the preparation of 9a with the exception that the reaction was stirred for 20 min at 0° C. Yield: 61% (colorless viscous oil). $^1$H NMR (CDCl$_3$): δ 2.92 (t, J=7.3 Hz, 2H), 4.06 (t, J=7.6 Hz, 2H), 4.71 (s, 2H), 5.17 (s, 2H), 5.46 (s, 2H), 6.68 (m, 2H), 7.29-7.44 (m, 11H).

2-(3,5-Difluorophenethyl)-6-hydroxy-1,2,4-triazine-3,5(2H,4H)-dione (10r)

Compound 10r was prepared as described for the preparation of 10a with the exception that the hydrogenation was performed overnight at 30 psi in pure methanol prior to treatment with sodium carbonate in methanol. Yield: 63% (white powder). Mp 256-260° C.; $^1$H NMR (DMSO-d$_6$): δ 2.95 (t, J=7.1 Hz, 2H), 3.92 (t, J=7.3 Hz, 2H), 6.95 (m, 2H), 7.06 (m, 1H), 11.69 (s, 1H), 12.05 (s, 1H).

Example 54

Synthesis of 2-((5-fluoronaphthalen-1-yl)methyl)-6-hydroxy-1,2,4-triazine-3,5(2H,4H)-dione 4-(Benzyloxymethyl)-6-bromo-2-((5-fluoronaphthalen-1-yl)methyl)-1,2,4-triazine-3,5(2H,4H)-dione (8s)

Compound 8s was prepared as described for the preparation of 8a with the exception that (5-fluoronaphthalen-1-yl)methanol was used in place of 2,2-difluoro-2-phenylethanol and no work-up was required. Yield: 94% (white solid cake). $^1$H NMR (CDCl$_3$): δ 4.69 (s, 2H), 5.52 (s, 2H), 5.54 (s, 2H), 7.22 (m, 3H), 7.29 (m, 3H), 7.54 (m, 2H), 7.64 (d, J=7.1 Hz, 1H), 8.03 (d, J=8.6 Hz, 1H), 8.17 (d, J=8.3 Hz, 1H).

6-(Benzyloxy)-4-(benzyloxymethyl)-2-((5-fluoronaphthalen-1-yl)methyl)-1,2,4-triazine-3,5(2H,4H)-dione (9s)

Compound 9s was prepared as described for the preparation of 9a with the exception that the reaction was stirred for 30 min at 0° C. Yield: 49% (white solid cake). $^1$H NMR (CDCl$_3$): δ 4.71 (s, 2H), 5.09 (s, 2H), 5.45 (s, 2H), 5.52 (s, 2H), 7.20-7.35 (m, 10H), 7.38 (d, J=4.0 Hz, 1H), 7.46 (m, 1H), 7.55 (m, 2H), 8.03 (d, J=8.8 Hz, 1H), 8.17 (d, J=8.8 Hz, 1H).

2-((5-Fluoronaphthalen-1-yl)methyl)-6-hydroxy-1,2,4-triazine-3,5(2H,4H)-dione (10s)

Compound 10s was prepared as described for the preparation of 10c with the exception that 4.0 equivalents of boron tribromide were added in one portion and the reaction time was 1h. The compound was triturated in EtOAc-water. Yield: 47% (white solid). Mp>260° C.; $^1$H NMR (DMSO-d$_6$): δ 5.34 (s, 2H), 7.39 (dd, J=7.8, 10.9 Hz, 1H), 7.54 (t, J=7.1 Hz, 1H), 7.60 (m, 2H), 8.01 (dd, J=8.6, 13.1 Hz, 2H), 11.70 (s, 1H), 12.22 (s, 1H).

Example 55

Synthesis of 2-(4-ethoxyphenethyl)-6-hydroxy-1,2,4-triazine-3,5(2H,4H)-dione 4-(Benzyloxymethyl)-6-bromo-2-(4-ethoxyphenethyl)-1,2,4-triazine-3,5(2H,4H)-dione (8t)

Compound 8t was prepared as described for the preparation of 8a with the exception that 2-(4-ethoxyphenyl)ethanol was used in place of 2,2-difluoro-2-phenylethanol. Yield: 60% (white solid). $^1$H NMR (CDCl$_3$): δ 1.38 (t, J=7.1 Hz, 3H), 2.97 (m, 2H), 3.98 (q, J=7.1 Hz, 2H), 4.13 (m, 2H), 4.65 (s, 2H), 5.48 (s, 2H), 6.82-6.84 (m, 2H), 7.11-7.13 (m, 2H), 7.28-7.34 (m, 5H).

6-(Benzyloxy)-2-(4-ethoxyphenethyl)-1,2,4-triazine-3,5(2H,4H)-dione (9t)

Compound 9t was prepared as described for the preparation of 9a with the exception that 8t was used in place of 8a. Yield: 68% (yellow oil). $^1$H NMR (CDCl$_3$): δ 1.37 (t, J=7.1 Hz, 3H), 2.89 (m, 2H), 3.95 (q, J=7.1 Hz, 2H), 4.62 (s, 2H), 4.70 (d, J=5.5 Hz, 2H), 5.14 (s, 2H), 5.45 (s, 2H), 7.25-7.45 (m, 14H).

2-(4-Ethoxyphenethyl)-6-hydroxy-1,2,4-triazine-3,5(2H,4H)-dione (10t)

Compound 10t was prepared as described for the preparation of 5a with the exception that the crude residue was dissolved in a minimum amount of methanol and subjected to purification by prep-HPLC (method: 20-70% acetonitrile-water-0.1% formic acid) to give compound 10t (15%, white solid). Mp 238-239° C. $^1$H NMR (DMSO-d$_6$): δ 1.30 (t, J=7.1 Hz, 3H), 2.83 (t, J=7.3 Hz, 2H), 3.83 (t, J=7.3 Hz, 2H), 3.97 (q, J=7.1 Hz, 2H), 6.83 (d, J=8.5 Hz, 2H), 7.08 (d, J=8.5 Hz, 2H), 11.71 (bs, 1H), 12.02 (bs, 1H).

Example 56

Synthesis of 6-hydroxy-2-((2-methylnaphthalen-1-yl)methyl)-1,2,4-triazine-3,5(2H,4H)-dione 4-(Benzyloxymethyl)-6-bromo-2-((2-methylnaphthalen-1-yl)methyl)-1,2,4-triazine-3,5(2H,4H)-dione (8u)

Compound 8u was prepared as described for the preparation of 8a with the exception that (2-methylnaphthalen-1-yl)methanol was used in place of 2,2-difluoro-2-phenylethanol. Yield: 30% (white solid). $^1$H NMR (DMSO-d$_6$): δ 2.60 (s, 3H), 4.63 (s, 2H), 5.39 (s, 2H), 5.54 (s, 2H), 7.25-7.33 (m, 4H), 7.44-7.65 (m, 4H), 7.87 (m, 2H), 8.14 (d, J=8.5 Hz, 1H).

6-(Benzyloxy)-4-(benzyloxymethyl)-2-((2-methylnaphthalen-1-yl)methyl)-1,2,4-triazine-3,5(2H,4H)-dione (9u)

Compound 9u was prepared as described for the preparation of 9a with the exception that 8u was used in place of 8a. Yield: 17% (yellow oil). $^1$H NMR (CDCl$_3$): δ 2.65 (s, 3H), 4.72 (s, 2H), 4.83 (s, 2H), 5.54 (s, 4H), 6.96 (m, 2H), 7.13-7.17 (m, 2H), 7.21-7.32 (m, 4H), 7.37-7.40 (m, 3H), 7.44-7.54 (m, 2H), 7.81-7.88 (m, 2H), 8.16 (d, J=8.5 Hz, 1H).

6-Hydroxy-2-((2-methylnaphthalen-1-yl)methyl)-1,2,4-triazine-3,5(2H,4H)-dione (10u)

Compound 10u was prepared as described for the preparation of 5e with the exception that the crude residue was dissolved in a minimum amount of methanol and subjected to purification by prep-HPLC (method: 20-70% acetonitrile-water-0.1% formic acid) to give compound 10u (27%, off-white solid). Mp>260° C. $^1$H NMR (DMSO-$d_6$): δ 2.61 (s, 3H), 5.34 (s, 2H), 7.39-7.53 (m, 3H), 7.82 (d, J=8.5 Hz, 1H), 7.89 (d, J=8.5 Hz, 1H), 8.17 (d, J=8.4 Hz, 1H), 11.41 (bs, 1H), 12.16 (bs, 1H).

Example 57

Synthesis of 2-(2-(dimethylamino)ethyl)-6-hydroxy-1,2,4-triazine-3,5(2H,4H)-dione

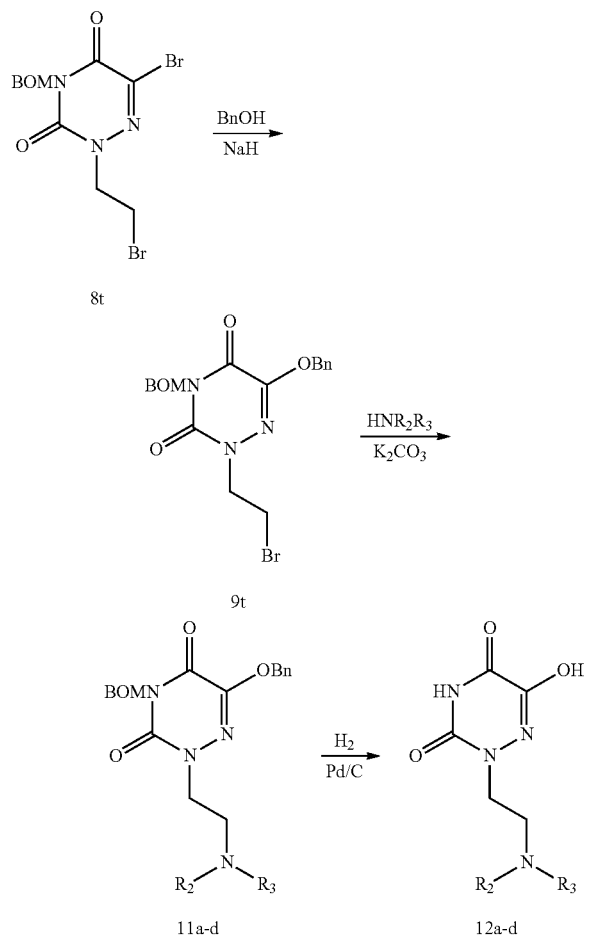

4-(Benzyloxymethyl)-6-bromo-2-(2-bromoethyl)-1,2,4-triazine-3,5(2H,4H)-dione (8t)

Compound 8t was prepared as described for the preparation of 8a with the exception that 2-bromoethanol was used in place of 2,2-difluoro-2-phenylethanol and no work-up was required. Yield: 85% (white cake). $^1$H NMR (CDCl$_3$): δ 3.63 ((t, J=6.7 Hz, 2H), 4.34 (t, J=6.7 Hz, 2H), 4.72 (s, 2H), 5.53 (s, 2H), 7.29-7.36 (m, 5H).

6-(Benzyloxy)-4-(benzyloxymethyl)-2-(2-bromoethyl)-1,2,4-triazine-3,5(2H,4H)-dione (9t)

Compound 9t was prepared as described for the preparation of 9a with the exception that 1.8 equivalents of benzyl alcohol and sodium hydride were used. Yield: 56% (white solid cake). $^1$H NMR (CDCl$_3$): δ. 3.56 (t, J=6.7 Hz, 2H), 4.23 (t, J=6.7 Hz, 2H), 4.71 (s, 2H), 5.23 (s, 2H), 5.50 (s, 2H), 7.29-7.46 (m, 10H).

6-(Benzyloxy)-4-(benzyloxymethyl)-2-(2-(dimethylamino)ethyl)-1,2,4-triazine-3,5(2H,4H)-dione (11a)

Compound 9t (0.20 g, 0.448 mmol), dimethylamine hydrochloride (0.044 g, 0.538 mmol, 1.2 equiv) and potassium carbonate (0.150 g, 1.08 mmol, 2.4 equiv) were heated together in DMF (5 mL) at 80° C. After 2 h heating, more dimethyl amine hydrochloride (0.010 g, 0.123 mmol) and potassium carbonate (0.054 g, 0.39 mmol) were added. The reaction was heated at same temperature over weekend and DMF removed in vacuo. The residue was partitioned between EtOAc and water and the organic phase was washed with brine, dried over Na$_2$SO$_4$ and concentrated to an oil. Purification by prep-HPLC (method: 20-70% acetonitrile-water-0.1% formic acid) provided 0.10 g (49%) of compound 11a as a formate salt. $^1$H NMR (CDCl$_3$): δ 2.52 ((s, 6H), 2.93 ((t, J=6.2 Hz, 2H), 4.10 (t, J=6.3 Hz, 2H), 4.70 (s, 2H), 5.18 (bs, 1H), 5.24 (s, 2H), 5.48 (s, 2H), 7.29-7.45 (m, 10H), 8.20 (s, 1H (HCOO—)).

2-(2-(Dimethylamino)ethyl)-6-hydroxy-1,2,4-triazine-3,5(2H,4H)-dione (12a)

Compound 13a (0.09 g, 0.197 mmol) was dissolved in methanol (10 mL) and one small spatula tip of palladium hydroxide was added. The mixture was hydrogenated at 50 psi overnight. The reaction was filtered through celite and the filtrate concentrated to give a solid which was triturated in EtOAc to give 0.025 g (63%) of compound 12a as a solid. Mp 200-205° C. $^1$H NMR (DMSO-$d_6$): δ 2.36 (s, 6H), 2.77 (m, 2H), 3.78 (t, J=6.1 Hz, 2H), 12.07 (bs, 2H).

Example 58

Synthesis of 6-hydroxy-2-(2-(4-isopropylpiperazin-1-yl)ethyl)-1,2,4-triazine-3,5(2H,4H)-dione 6-(Benzyloxy)-4-(benzyloxymethyl)-2-(2-(4-isopropylpiperazin-1-yl)ethyl)-1,2,4-triazine-3,5(2H,4H)-dione (11b)

Compound 11b was prepared as described for the preparation of 11a with the exception that 1-isopropylpiperazine was used in place of dimethyl amine hydrochloride and only 1.2 equivalent of potassium carbonate was used. Yield: 45% (thick oil). $^1$H NMR (CDCl$_3$): δ 1.18 (d, J=6.6 Hz, 6H), 2.62 (t, J=5.9 Hz, 2H), 2.74 (m, 4H), 3.02 (bs, 4H), 3.23 (m, 1H), 3.94 (t, J=5.9 Hz, 2H), 4.70 (s, 2H), 5.23 (s, 2H), 5.48 (s, 2H), 7.28-7.44 (m, 10H).

6-Hydroxy-2-(2-(4-isopropylpiperazin-1-yl)ethyl)-1,2,4-triazine-3,5(2H,4H)-dione (12b)

Compound 12b was prepared as described for the preparation of 12a with the exception that the hydrogenation was performed in the presence of a catalytic amount of sodium carbonate and the crude residue was purified by prep-HPLC (method: 0-20% acetonitrile-water-0.1% formic acid) to give compound 12b as a formate salt. Yield: 54% (white crystal). Mp 95-97° C.; $^1$H NMR (DMSO-$d_6$): δ 1.00 (d, J=6.3 Hz, 6H), 2.50 (m, 4H), 2.55 (m, 6H), 2.75 (m, 1H), 3.74 (t, J=6.3 Hz, 2H), 8.18 (s, 1H (HCOO—)).

Example 59

Synthesis of 2-(2-(4-(2-fluorophenyl)piperazin-1-yl) ethyl)-6-hydroxy-1,2,4-triazine-3,5(2H,4H)-dione 6-(Benzyloxy)-4-(benzyloxymethyl)-2-(2-(4-(2-fluorophenyl)piperazin-1-yl)ethyl)-1,2,4-triazine-3,5(2H, 4H)-dione (11c)

Compound 11c was prepared as described for the preparation of 11a with the exception that 1-(2-fluorophenyl) piperazine was used in place of dimethyl amine hydrochloride and only 1.2 equivalent of potassium carbonate was used. Yield: 77% (thick oil). $^1$H NMR (CDCl$_3$): δ 2.66 (m, 6H), 3.05 (m, 4H), 4.02 (t, J=6.6 Hz, 2H), 4.71 (s, 2H), 5.24 (s, 2H), 5.51 (s, 2H), 6.90 (m, 2H), 7.03 (m, 2H), 7.29 (m, 2H), 7.35-7.41 (m, 6H), 7.44 (m, 2H).

2-(2-(4-(2-Fluorophenyl)piperazin-1-yl)ethyl)-6-hydroxy-1,2,4-triazine-3,5(2H,4H)-dione (12c)

Compound 12c was prepared as described for the preparation of 12a. Mp 265° C. (decomp). $^1$H NMR (DMSO-$d_6$): δ 2.66 (m, 6H), 2.98 (m, 4H), 3.81 (t, J=7.8 Hz, 2H), 6.93-7.03 (m, 2H), 7.07-7.14 (m, 2H), 11.71 (s, 1H), 12.06 (s, 1H).).

Example 60

Synthesis of 2-(2-(3,4-dihydroisoquinolin-2(1H)-yl) ethyl)-6-hydroxy-1,2,4-triazine-3,5(2H,4H)-dione 6-(Benzyloxy)-4-(benzyloxymethyl)-2-(2-(3,4-dihydroisoquinolin-2(1H)-yl)ethyl)-1,2,4-triazine-3,5 (2H,4H)-dione (11d)

Compound 11d was prepared as described for the preparation of 11a with the exception that 1,2,3,4-tetrahydroisoquinoline was used in place of dimethyl amine hydrochloride and only 1.2 equivalent of potassium carbonate and 2.6 equivalents of 1,2,3,4-tetrahydroisoquinoline were used. Yield: 55% (yellow oil). $^1$H NMR (CDCl$_3$): δ 2.91 (m, 6H), 3.79 (s, 2H), 4.14 (t, J=6.4 Hz, 2H), 4.68 (s, 2H), 5.25 (s, 2H), 5.50 (s, 2H), 7.04-7.12 (m, 2H), 7.15-7.17 (m, 2H), 7.27-7.48 (m, 10H).

2-(2-(3,4-Dihydroisoquinolin-2(1H)-yl)ethyl)-6-hydroxy-1,2,4-triazine-3,5(2H,4H)-dione (12d)

Compound 12d was prepared as described for the preparation of 12a with the exception that the compound was purified by prep-HPLC (method: 0-20% acetonitrile-water-0.1% formic acid). Yield: 49% (white solid). $^1$H NMR (DMSO-$d_6$): δ 2.74 (m, 6H), 3.64 (m, 2H), 3.88 (t, J=6.4 Hz, 2H), 7.02-7.10 (m, 4H), 12.02 (bs, 2H).

Example 61

Synthesis of 6-hydroxy-2-phenethyl-3-thioxo-3,4-dihydro-1,2,4-triazin-5(2H)-one

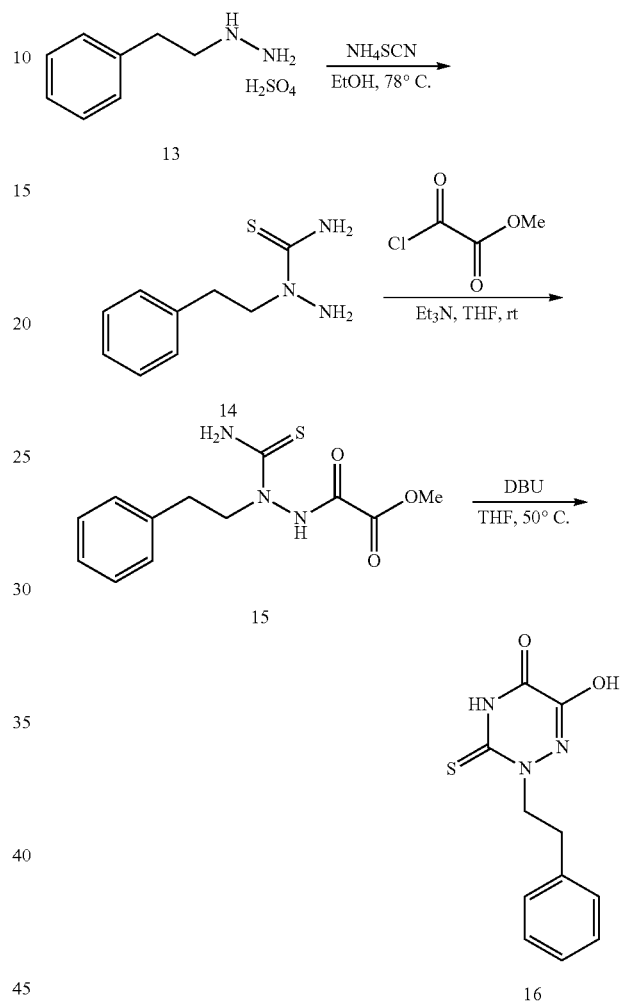

1-Phenethylhydrazinecarbothioamide (14)

To a suspension of 13 (5.00 g, 21.4 mmol) in ethanol (50.0 ml) at room temperature was added ammonium thiocyanate (1.60 g, 21.4 mmol). The white suspension was heated at 78° C. for 50 hours. The reaction was cooled to room temperature. The resultant solid was then removed by vacuum filtration. The filtrate volume was reduced by approximately one-half and the resultant solid was removed by filtration. This was repeated 4 times; this resultant solid was identified by LCMS as unreacted phenethylhydrazine. The remaining filtrate was partitioned between EtOAc (50 mL) and sat'd NaHCO$_3$ (20 mL). The organic layer was dried over MgSO$_4$, filtered, and concentrated. The crude material was purified by silica gel column chromatography (80% EtOAc/hexanes w/0.1% NH$_4$OH) to give 660 mg of 14 as a white solid (16% yield): $^1$H NMR (DMSO-$d_6$) δ 2.94 (m, 2H), 4.09 (m, 2H), 4.88 (s, 2H), 7.18-7.33 (m, 5H), 7.44 (br s, 2H).

Methyl 2-(2-carbamothioyl-2-phenethylhydrazinyl)-2-oxoacetate (15)

To a solution of 14 (660 mg, 3.38 mmol) at room temperature in THF (15 mL) was added methyl chloroox-oacetate (414 mg, 3.38 mmol) in THF (5 mL) over 2 minutes. The solution stirred for 14 hours and then concentrated to dryness. The residue was dissolved in EtOAc (50 mL) and washed with sat'd NaHCO$_3$ (1×25 mL). The organic phase was dried over MgSO$_4$, filtered, and concentrated. The crude material was purified by silica gel column chromatography (5% MeOH/CH$_2$Cl$_2$) to give 300 mg of 15 as a white solid (32% yield): 1H NMR (CDCl$_3$) δ 3.09 (t, J=7.03 Hz, 2H), 3.88 (s, 3H), 4.32 (m, 2H), 6.03 (s, 2H), 7.25-7.37 (m, 5H), 8.22 (br s, 1H).

6-Hydroxy-2-phenethyl-3-thioxo-3,4-dihydro-1,2,4-triazin-5(2H)-one (16)

To a solution of 15 (300 mg, 1.07 mmol) in THF (5 mL) at room temperature was added DBU (324 mg, 2.14 mmol) dropwise in THF (3 mL). The reaction was stirred at room temperature for 14 hours and then heated to 50° C. for 30 minutes. The reaction was concentrated to dryness. The residue was resuspended in EtOAc (50 ml) and washed with 5% KHSO$_4$. The organic layer was separated, dried over MgSO$_4$, filtered, concentrated, and then purified by silica gel chromatography (1% HOAc in EtOAc) to afford 31 mg of 16 as a yellow solid (12% yield): mp 190-230° C.; $^1$H NMR (CD$_3$OD) δ 3.11 (m, 2H), 4.41 (m, 2H), 7.19-7.31 (m, 5H); $^{13}$C NMR (CD$_3$OD) δ 32.6, 57.1, 126.2, 128.2, 128.5, 137.9, 151.6, 154.1, 169.2. Anal. Calcd. for C11H11N3S1O2.0.4HOAc: C, 51.86; H, 4.65; N, 15.37; S, 11.73. Found: C, 51.93; H, 4.94; N, 15.44; S, 11.47.

Example 62

Synthesis of 6-hydroxy-2-(2-oxo-2-phenylethyl)-1,2,4-triazine-3,5(2H,4H)-dione

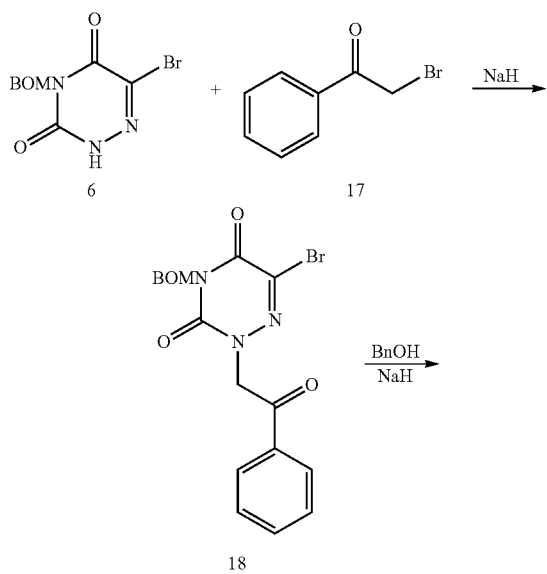

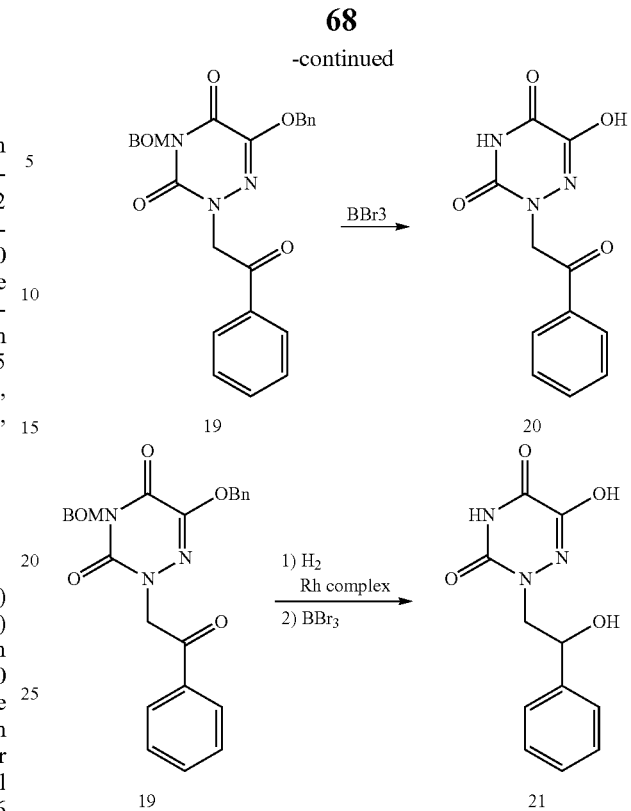

4-(Benzyloxymethyl)-6-bromo-2-(2-oxo-2-phenylethyl)-1,2,4-triazine-3,5(2H,4H)-dione (18)

To a suspension of NaH (0.14 g, 3.53 mmol, 1.1 equiv) in DMF (2.5 mL) at rt was slowly added a solution of 4-(benzyloxymethyl)-6-bromo-1,2,4-triazine-3,5(2H,4H)-dione (6, 1.0 g, 3.21 mmol) in DMF (7 mL) via syringe. The mixture was stirred at rt for 1 h after which bromoacetophenone (17, 0.70 g, 3.53 mmol, 1.1 equiv) was added in one portion as a solid. The reaction was stirred for 3.5 h and water was added. The reaction was partitioned between EtOAc and water. The organic layer was dried over Na$_2$SO$_4$ and concentrated to give a residue which was purified by Biotage Isolera One using EtOAc/hexanes to give 1.27 g (92%) of compound 18 as a white solid. $^1$H NMR (CDCl$_3$): δ 4.72 (s, 2H), 5.40 (s, 2H), 5.54 (s, 2H), 7.31-7.39 (m, 5H), 7.54 (t, J=7.6 Hz, 2H), 7.67 (m, 1H), 7.97 (m, 2H).

6-(Benzyloxy)-4-(benzyloxymethyl)-2-(2-oxo-2-phenylethyl)-1,2,4-triazine-3,5(2H,4H)-dione (19)

Compound 19 was prepared as described for the preparation of 9a with the exception that the reaction was stirred at 0° C. for 30 min. Yield: 45% (yellow oil). $^1$H NMR (CDCl$_3$): δ 4.72 (s, 2H), 5.16 (s, 2H), 5.29 (s, 2H), 5.53 (s, 2H), 7.29-7.41 (m, 10H), 7.54 (t, J=7.3 Hz, 2H), 7.67 (m, 1H), 7.99 (m, 2H).

6-Hydroxy-2-(2-oxo-2-phenylethyl)-1,2,4-triazine-3,5(2H,4H)-dione (20)

Compound 20 was prepared as described for the preparation of 10c with the exception that 4.0 equivalents of boron tribromide were added in one portion and the reaction time was 10 min. After extraction, the crude residue was triturated in a EtOAc-hexanes mixture to afford compound 20 as a white solid. Yield: 63%. Mp 220-221° C., $^1$H NMR (DMSO-d$_6$): δ 5.27 (s, 2H), 7.58 (t, J=7.8 Hz, 2H), 7.71 (t, J=7.6 Hz, 1H), 8.02 (d, J=7.3 Hz, 2H), 11.78 (bs, 1H), 12.30 (s, 1H).

6-Hydroxy-2-(2-hydroxy-2-phenylethyl)-1,2,4-triazine-3,5(2H,4H)-dione (21)

Compound 19 (0.17 g, 0.37 mmol) was dissolved in a 2:1 mixture of methanol and EtOAc (15 mL) and a small spatula tip of chloro(1,5-cyclooctadiene)rhodium(I) dimer was added followed by the addition of one drop of triethylamine. The mixture was stirred for 36 h under hydrogen at 300 psi using a mechanical stirrer. The reaction was filtered and concentrated to a brown oil which was then treated with boron tribromide (1.50 mL, 1.50 mmol, 4 equiv) in dichloromethane (5 mL) for 1.5 h. Water was added. The mixture was concentrated to a residue which was subjected to purification by prep-HPLC (method: 10-50% acetonitrile-water-0.1% formic acid). Yield: 26% (beige solid). Mp 201-203° C., $^1$H NMR (DMSO-d$_6$): δ 3.66 (dd, J=4.0, 13.1 Hz, 1H), 3.85 (dd, J=9.1, 13.4 Hz, 1H), 4.91 (dd, J=4.3, 9.4 Hz, 1H), 5.52 (bs, 1H), 7.27-7.34 (m, 5H), 11.66 (s, 1H), 12.03 (s, 1H).

Example 63

Synthesis of 6-Hydroxy-2-(quinolin-8-ylmethyl)-1,2,4-triazine-3,5(2H,4H)-dione

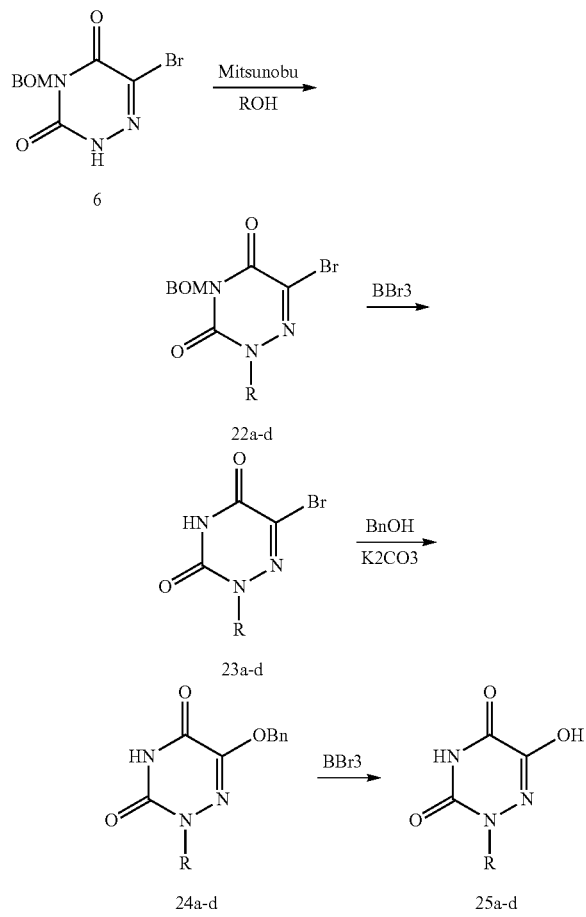

4-(Benzyloxymethyl)-6-bromo-2-(quinolin-8-ylmethyl)-1,2,4-triazine-3,5(2H,4H)-dione (22a)

Compound 22a was prepared as described for the preparation of 8a with the exception that quinolin-8-ylmethanol was used in place of 2,2-difluoro-2-phenylethanol and no work-up was required. Yield: 93%. $^1$H NMR (CDCl$_3$): δ 4.74 (s, 2H), 5.56 (s, 2H), 5.87 (s, 2H), 7.30-7.37 (m, 5H), 7.45 (dd, J=4.3, 8.3 Hz, 1H), 7.53 (m, 2H), 7.82 (m, 1H), 8.18 (dd, J=1.8, 8.3 Hz, 1H), 8.93 (dd, J=1.8, 4.0 Hz, 1H).

6-Bromo-2-(quinolin-8-ylmethyl)-1,2,4-triazine-3,5(2H,4H)-dione (23a)

Compound 23a was prepared as described for the preparation of 5e with the exception that 2.3 equiv of boron tribromide were added at rt and the reaction was stirred for 1 h. The crude material was triturated in methanol to give the first crop of the desired product. The filtrate was concentrated and purified by prep-HPLC (method: 20-70% acetonitrile-water-0.1% formic acid) to give the second crop. Combined yield: 42% (beige solid). $^1$H NMR (DMSO-d$_6$): δ 5.26*(s, 0.5H), 5.68*(s, 1.5H), 7.63 (t, J=7.3 Hz, 1H), 7.70 (m, 2H), 8.0 (d, J=8.1 Hz, 1H), 8.54 (m, 1H), 9.01 (m, 1H), 12.65 (s, 1H).

6-(Benzyloxy)-2-(quinolin-8-ylmethyl)-1,2,4-triazine-3,5(2H,4H)-dione (24a)

A mixture of 6-bromo-2-(quinolin-8-ylmethyl)-1,2,4-triazine-3,5(2H,4H)-dione (23a, 0.14 g, 0.42 mmol), K$_2$CO$_3$ (0.84 mmol, 0.12 g, 2.0 equiv) and benzyl alcohol (1 mL) was heated over the weekend at 150° C. Aqueous 10% KHSO$_4$ solution was added and the compound was extracted with EtOAc. The organic layer was dried over Na$_2$SO$_4$, filtered and concentrated to give an oil which was subjected to purification by Biotage Isolera One using EtOAc/hexanes to provide the first crop (0.015 g) of compound 24. The aqueous layer containing the desired product was acidified to pH ~6 and the compound was extracted with EtOAc. The organic layer was washed with brine, dried over Na$_2$SO$_4$ and concentrated to give the second crop (0.095 g) of compound 24. Combined yield: 73% (beige solid). $^1$H NMR (DMSO-d$_6$): δ 5.03 (s, 2H), 5.60 (s, 2H), 7.31 (m, 5H), 7.57 (m, 3H), 7.94 (m, 1H), 8.42 (dd, J=1.8, 8.3 Hz, 1H), 8.97 (dd, J=1.8, 4.3 Hz, 1H).

6-Hydroxy-2-(quinolin-8-ylmethyl)-1,2,4-triazine-3,5(2H,4H)-dione (25a)

Compound 25a was prepared as described for the preparation of 5e with the exception that 4 equiv of boron tribromide were added at rt and the reaction was stirred for 2.5 h. The crude material was purified by prep-HPLC (method: 0-20% acetonitrile-water-0.1% formic acid) to give the compound 25. Yield: 44% (beige solid). Mp 239-241° C.; $^1$H NMR (DMSO-d$_6$): Mp 239-241° C.; $^1$H NMR (DMSO-d$_6$): δ 5.52 (s, 2H), 7.54-7.62 (m, 3H), 7.90 (d, J=8.1 Hz, 1H), 8.40 (dd, J=1.8, 8.3 Hz, 1H), 8.95 (dd, J=1.8, 4.0 Hz, 1H), 12.05 (bs, 2H).

Example 64

Synthesis of 2-((4-fluoronaphthalen-1-yl)methyl)-6-hydroxy-1,2,4-triazine-3,5(2H,4H)-dione 4-(Benzyloxymethyl)-6-bromo-2-((4-fluoronaphthalen-1-yl)methyl)-1,2,4-triazine-3,5(2H,4H)-dione (22b)

Compound 22b was prepared as described for the preparation of 8a with the exception that (4-fluoronaphthalen-1- yl)methanol was used in place of 2,2-difluoro-2-phenylethanol. Yield: 71% (light yellow oil). $^1$H NMR (DMSO-d$_6$): δ 4.61 (s, 2H), 5.36 (s, 2H), 5.52 (s, 2H), 7.25-7.36 (m, 6H), 7.54-7.57 (m, 1H), 7.68-7.72 (m, 2H), 8.11-8.13 (m, 1H), 8.24 (m, 1H).

6-Bromo-2-((4-fluoronaphthalen-1-yl)methyl)-1,2,4-triazine-3,5(2H,4H)-dione (23b)

Compound 23b was prepared as described for the preparation of 5e however the crude material was used directly in the next step without further purification.

6-(Benzyloxy)-2-((4-fluoronaphthalen-1-yl)methyl)-1,2,4-triazine-3,5(2H,4H)-dione (24b)

Compound 24b was prepared as described for the preparation of 4a with the exception that 23b was used in place of 3a. Yield: 27% (white solid). $^1$H NMR (DMSO-d$_6$): δ 5.03 (s, 2H), 5.36 (s, 2H), 7.29-7.34 (m, 6H), 7.50-7.54 (m, 1H), 7.67-7.70 (m, 2H), 8.10-8.13 (m, 1H), 8.27-8.29 (m, 1H), 12.28 (bs, 1H).

2-((4-Fluoronaphthalen-1-yl)methyl)-6-hydroxy-1,2,4-triazine-3,5(2H,4H)-dione (25b)

Compound 25b was prepared as described for the preparation of 5e with the exception that the material was subject to purification by prep-HPLC (method: 20-70% acetonitrile-water-0.1% formic acid) to give compound 25b (32%, white solid). Mp>260° C. $^1$H NMR (DMSO-d$_6$): δ 5.30 (s, 2H), 7.28-7.33 (m, 1H), 7.42-7.46 (m, 1H), 7.66-7.71 (m, 2H), 8.09-8.12 (m, 1H), 8.22-8.24 (m, 1H), 11.68 (bs, 1H), 12.19 (bs, 1H).

Example 65

Synthesis of 6-hydroxy-2-((4-methylnaphthalen-1-yl)methyl)-1,2,4-triazine-3,5(2H,4H)-dione

4-(Benzyloxymethyl)-6-bromo-2-((4-methylnaphthalen-1-yl)methyl)-1,2,4-triazine-3,5(2H,4H)-dione (22c)

Compound 22c was prepared as described for the preparation of 8a with the exception that (4-methylnaphthalen-1-yl)methanol was used in place of 2,2-difluoro-2-phenylethanol. Yield: 36% (white solid). $^1$H NMR (CDCl$_3$): δ 2.71 (s, 3H), 4.67 (s, 2H), 5.50 (s, 2H), 5.52 (s, 2H), 7.21-7.24 (m, 3H), 7.29-7.33 (m, 3H), 7.48 (d, J=7.1 Hz, 1H), 7.56-7.61 (m, 2H), 8.05-8.07 (m, 1H), 8.25-8.27 (m, 1H).

6-Bromo-2-((4-methylnaphthalen-1-yl)methyl)-1,2,4-triazine-3,5(2H,4H)-dione (23c)

Compound 23c was prepared as described for the preparation of 5e however the crude material was used directly in the next step without further purification.

6-(Benzyloxy)-2-((4-methylnaphthalen-1-yl)methyl)-1,2,4-triazine-3,5(2H,4H)-dione (24c)

Compound 24c was prepared as described for the preparation of 4a with the exception that 23c was used in place of 3a. Yield: 25% (yellow oil). $^1$H NMR (CDCl$_3$): δ 2.73 (s, 3H), 5.08 (s, 2H), 5.44 (s, 2H), 7.23-7.38 (m, 6H), 7.45 (d, J=7.2 Hz, 1H), 7.56-7.60 (m, 2H), 8.05-8.09 (m, 1H), 8.26-8.30 (m, 1H).

6-Hydroxy-2-((4-methylnaphthalen-1-yl)methyl)-1,2,4-triazine-3,5(2H,4H)-dione (25c)

Compound 25c was prepared as described for the preparation of 5e with the exception that the crude residue was dissolved in a minimum amount of methanol and subjected to purification by prep-HPLC (method: 20-70% acetonitrile-water-0.1% formic acid) to give compound 25c (10%, white solid). Mp>270° C. $^1$H NMR (DMSO-d$_6$): δ 2.64 (s, 3H), 5.29 (s, 2H), 7.29-7.34 (m, 2H), 7.57-7.61 (m, 2H), 8.05-8.07 (m, 1H), 8.15-8.17 (m, 1H), 11.66 (bs, 1H), 12.16 (bs, 1H).

Example 66

Synthesis of 2-((6-bromonaphthalen-1-yl)methyl)-6-hydroxy-1,2,4-triazine-3,5(2H,4H)-dione

4-(Benzyloxymethyl)-6-bromo-2-((6-bromonaphthalen-1-yl)methyl)-1,2,4-triazine-3,5(2H,4H)-dione (22d)

Compound 22d was prepared as described for the preparation of 8a with the exception that (6-bromonaphthalen-1-yl)methanol was used in place of 2,2-difluoro-2-phenylethanol. Yield: 78% (white solid). $^1$H NMR (DMSO-d$_6$): δ 4.62 (s, 2H), 5.25 (s, 2H), 5.36 (s, 2H), 7.27-7.31 (m, 5H), 7.52-7.57 (m, 2H), 7.65 (m, 1H), 7.88-7.94 (m, 3H), 8.22 (m, 1H).

6-Bromo-2-((6-bromonaphthalen-1-yl)methyl)-1,2,4-triazine-3,5(2H,4H)-dione (23d)

Compound 23d was prepared as described for the preparation of 5e with the exception that 2.3 equiv of boron tribromide were added at rt and the crude residue was triturated with Et$_2$O. Yield: 17% (white solid). $^1$H NMR (DMSO-d$_6$): δ 5.19 (s, 2H), 7.53 (dd, J=8.6, 1.6 Hz, 1H), 7.64 (dd, J=8.7, 1.9 Hz, 1H), 7.88-7.92 (m, 3H), 8.20 (d, J=1.9 Hz, 1H), 12.62 (s, 1H).

6-(Benzyloxy)-2-((6-bromonaphthalen-1-yl)methyl)-1,2,4-triazine-3,5(2H,4H)-dione (24d)

Compound 24d was prepared as described for the preparation of 4a except the product was purified by Biotage Isolera One using EtOAc/hexanes. Yield: 41% (white solid). Yield: 20% (tan solid). $^1$H NMR (DMSO-d$_6$): δ 5.13 (s, 2H), 5.19 (s, 2H), 7.21-7.23 (m, 3H), 7.32-7.34 (m, 2H), 7.47-7.49 (m, 1H), 7.57-7.60 (m, 1H), 7.76-7.83 (m, 3H), 8.06 (m, 1H).

2-((6-Bromonaphthalen-1-yl)methyl)-6-hydroxy-1,2,4-triazine-3,5(2H,4H)-dione 25d Compound 25d was prepared as described for the preparation of 5e with the exception that the crude residue was dissolved in a minimum amount of methanol and subjected to purification by prep-HPLC (method: 20-70% acetonitrile-water-0.1% formic acid) to give compound 25d (16%, white solid). Mp>260° C. $^1$H NMR (DMSO-d$_6$): δ 5.01 (s, 2H), 7.50 (d, J=8.6 Hz, 1H), 7.63 (d, J=8.8 Hz, 1H), 7.83 (s, 1H), 7.89 (d, J=8.6 Hz, 2H), 8.19 (s, 1H), 11.78 (bs, 1H), 12.14 (s, 1H).

Example 67

Synthesis of 2-(2-(2'-fluorobiphenyl-4-yl)ethyl)-6-hydroxy-1,2,4-triazine-3,5(2H,4H)-dione

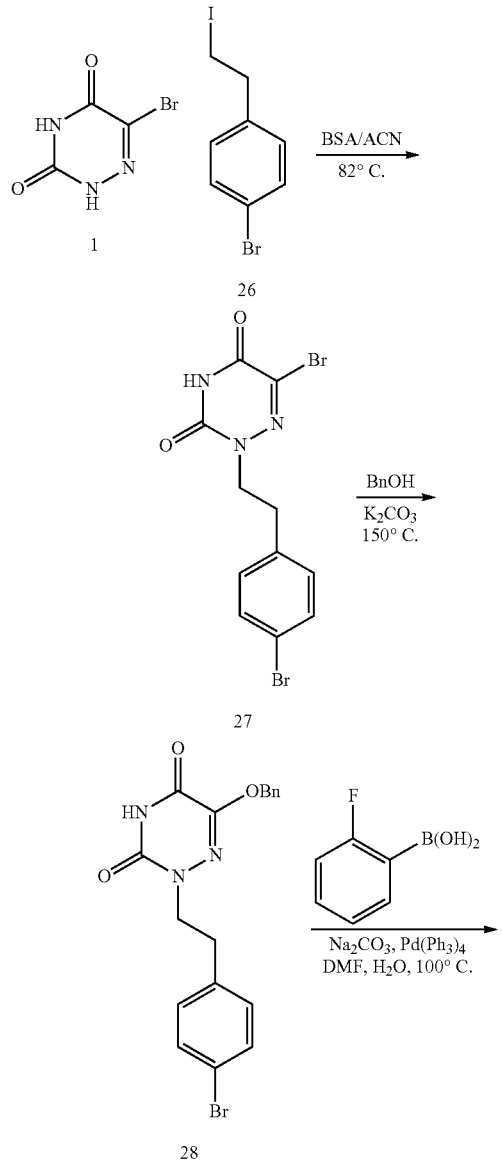

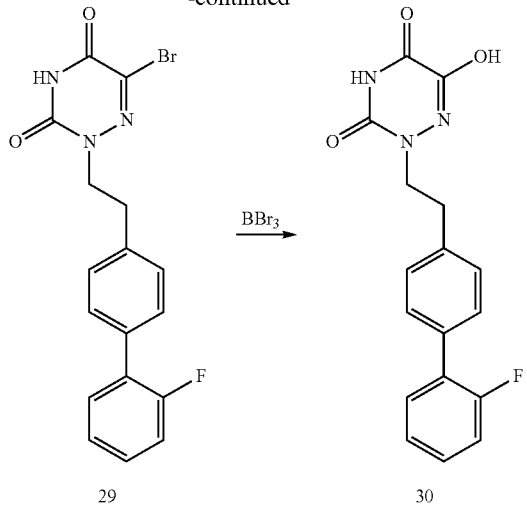

6-Bromo-2-(4-bromophenethyl)-1,2,4-triazine-3,5(2H,4H)-dione (27)

Compound 26 was prepared as described for the preparation of 3a with the exception that 26 was used in place of phenethyl iodide. Yield: 18% (white solid). $^1$H NMR (CDCl$_3$): δ 2.92 (t, J=7.1 Hz, 2H), 4.03 (t, J=7.1 Hz, 2H), 7.17-7.21 (m, 2H), 7.47-7.49 (m, 2H), 12.52 (bs, 1H).

6-(Benzyloxy)-2-(4-bromophenethyl)-1,2,4-triazine-3,5(2H,4H)-dione (28)

Compound 28 was prepared as described for the preparation of 4a with the exception that the product was purified by Biotage Isolera One using EtOAc/hexanes. Yield: 60% (white solid). $^1$H NMR (DMSO-d$_6$): δ 2.89 (t, J=7.0 Hz, 2H), 3.96 (t, J=7.0 Hz, 2H), 5.05 (s, 2H), 7.10-7.12 (m, 2H), 7.37-7.46 (m, 7H), 12.12 (bs, 1H).

6-(Benzyloxy)-2-(2-(2'-fluorobiphenyl-4-yl)ethyl)-1,2,4-triazine-3,5(2H,4H)-dione (29)

To a degassed solution of 6-(benzyloxy)-2-(4-bromophenethyl)-1,2,4-triazine-3,5(2H,4H)-dione (28, 61 mg, 0.152 mmol, 1.0 equiv), 2-fluorophenylboronic acid (42.4 mg, 0.303 mmol, 2.0 equiv), sodium carbonate (52 mg, 0.494 mmol, 3.25 equiv) in DMF (4 mL) and H$_2$O (0.5 mL) was added Pd(PPh$_3$)$_4$ (18 mg, 0.015 mmol, 0.10 equiv.). The mixture was heated at 130° C. overnight. The reaction was concentrated in vacuo. The resulting residue was dissolved in EtOAc and the organic solution was washed with water, brine, dried over MgSO$_4$, and concentrated to give a solid which was purified by Biotage Isolera One using EtOAc/hexanes. The material contained a mixture of starting material and product and was taken to the next step without further characterization.

2-(2-(2'-Fluorobiphenyl-4-yl)ethyl)-6-hydroxy-1,2,4-triazine-3,5(2H,4H)-dione (30)

Compound 30 was prepared as described for the preparation of 5e with the exception that 2 equiv of boron tribromide were added at rt in one portion and that the reaction was stirred at rt for 1.5 h. Yield: 21% (white solid).

¹H NMR (DMSO-d₆): δ 2.97 (t, J=7.4 Hz, 2H), 3.92 (t, J=7.4 Hz, 2H), 7.27-7.33 (m, 4H), 7.38-7.43 (m, 1H), 7.48-7.53 (m, 3H), 11.73 (bs, 1H), 12.05 (bs, 1H).

Example 68

Synthesis of 6-hydroxy-2-(4-morpholinophenethyl)-1,2,4-triazine-3,5(2H,4H)-dione

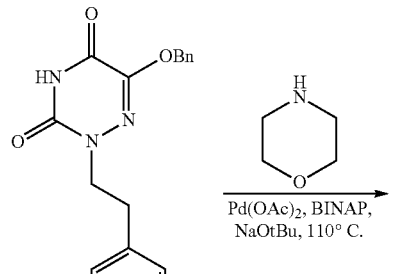

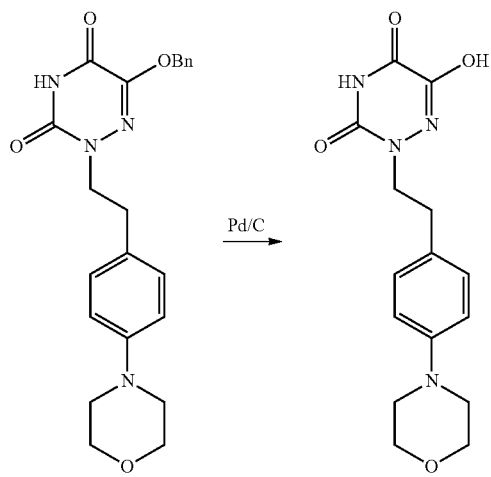

6-(Benzyloxy)-2-(4-morpholinophenethyl)-1,2,4-triazine-3,5(2H,4H)-dione (31)

To a solution of 27 (75 mg, 0.187 mmol, 1.0 equiv), morpholine (32 mg, 0.374 mmol, 2.0 equiv), Pd(OAc)₂ (6.2 mg, 0.028 mmol, 0.15 equiv), racemic BINAP (17 mg, 0.028 mmol, 0.15 equiv) in toluene (3 mL) was added NaOtBu (72 mg, 0.748 mmol, 4.0 equiv). The mixture was refluxed overnight, cooled to room temperature, and then diluted with CHCl₃. The organic phase was washed with water, dried over MgSO₄, and concentrated. The crude residue was passed through a small plug of silica gel, but was then taken to the next step without further purification or characterization.

6-Hydroxy-2-(4-morpholinophenethyl)-1,2,4-triazine-3,5(2H,4H)-dione (32)

Compound 31 was prepared as described for the preparation of 5e with the exception that the final compound was purified by prep-HPLC (method: 20-70% acetonitrile-water-0.1% formic acid). Yield: 42% (tan solid). Mp>260° C.; ¹H NMR (CD₃OD): δ 2.91 (t, J=7.1 Hz, 2H), 3.09 (m, 4H), 3.82 (m, 4H), 3.91 (t, J=7.5 Hz, 2H), 6.89 (m, 2H), 7.11 (m, 2H).

Example 69

In Vitro D-Amino Acid Oxidase Assay

Materials.

D-Serine was purchased from Bachem Biosciences Inc. (King of Prussia, Pa.), horse radish peroxidase from Worthington Biochemical Corporation (Freehold, N.J.), and o-phenylenediamine from Pierce Biotechnology, Inc (Rockford, Ill.). All other chemicals were obtained from Sigma-Aldrich (St. Louis, Mo.).

Methods.

A reliable 96-well plate D-amino acid oxidase (DAAO) assay was developed based on previously published reports (*J. Biol. Chem.* 277: 27782 (2002)). Briefly, D-serine (5 mM) was oxidatively deaminated by human recombinant D-amino acid oxidase in the presence of molecular oxygen and flavin adenosine dinucleotide (FAD, 1 μM), to yield the corresponding α-keto acid, ammonia and hydrogen peroxide. The resulting hydrogen peroxide was quantified using horseradish peroxidase (0.01 mg/mL) and o-phenylenediamine (180 μg/mL), which displays a defined yellow absorbance at 411 nm when it becomes oxidized. All reactions were carried out for 20 min at room temperature in a 100-μL volume in Tris buffer (50 mM, pH 8.5). Additionally, stock solutions and serial dilutions of potential DAO inhibitors were made in 10:90 DMSO:buffer with a final assay DMSO concentration of 1%. The results are summarized in Table 1.

TABLE 1

Inhibition of DAAO

| | Name | IC₅₀ (μM) |
|---|---|---|
| 5a | 6-Hydroxy-2-phenethyl-1,2,4-triazine-3,5(2H,4H)-dione | 0.08 |
| 5b | 2-(4-fluorophenethyl)-6-hydroxy-1,2,4-triazine-3,5(2H,4H)-dione | 0.06 |
| 5c | 2-(3-fluorophenethyl)-6-hydroxy-1,2,4-triazine-3,5(2H,4H)-dione | 0.06 |
| 5d | 2-(2-fluorophenethyl)-6-hydroxy-1,2,4-triazine-3,5(2H,4H)-dione | 0.08 |
| 5e | 2-(4-chlorophenethyl)-6-hydroxy-1,2,4-triazine-3,5(2H,4H)-dione | 0.03 |
| 5f | 2-(3-chlorophenethyl)-6-hydroxy-1,2,4-triazine-3,5(2H,4H)-dione | 0.06 |
| 5g | 2-(2-chlorophenethyl)-6-hydroxy-1,2,4-triazine-3,5(2H,4H)-dione | 0.1 |
| 5h | 6-Hydroxy-2-(4-methylphenethyl)-1,2,4-triazine-3,5(2H,4H)-dione | 0.1 |
| 5i | 6-Hydroxy-2-(3-methylphenethyl)-1,2,4-triazine-3,5(2H,4H)-dione | 0.06 |
| 5j | 6-Hydroxy-2-(2-methylphenethyl)-1,2,4-triazine-3,5(2H,4H)-dione | 0.06 |

TABLE 1-continued

Inhibition of DAAO

| | Name | IC$_{50}$ (μM) |
|---|---|---|
| 5k | 6-hydroxy-2-(4-(trifluoromethyl)phenethyl)-1,2,4-triazine-3,5(2H,4H)-dione | 0.08 |
| 5l | 6-hydroxy-2-(3-(trifluoromethyl)phenethyl)-1,2,4-triazine-3,5(2H,4H)-dione | 0.09 |
| 5m | 2-(2,4-dichlorophenethyl)-6-hydroxy-1,2,4-triazine-3,5(2H,4H)-dione | 0.08 |
| 5n | 6-hydroxy-2-(2-(naphthalen-1-yl)ethyl)-1,2,4-triazine-3,5(2H,4H)-dione | 0.1 |
| 5o | 2-(2-(biphenyl-4-yl)ethyl)-6-hydroxy-1,2,4-triazine-3,5(2H,4H)-dione | 0.03 |
| 5p | 6-hydroxy-2-methyl-1,2,4-triazine-3,5(2H,4H)-dione | 3 |
| 5q | 6-hydroxy-2-isopentyl-1,2,4-triazine-3,5(2H,4H)-dione | 0.3 |
| 5r | 2-(3,3-dimethylbutyl)-6-hydroxy-1,2,4-triazine-3,5(2H,4H)-dione | 40 |
| 5s | 6-hydroxy-2-(3-phenylpropyl)-1,2,4-triazine-3,5(2H,4H)-dione | 2 |
| 5t | 2-benzyl-6-hydroxy-1,2,4-triazine-3,5(2H,4H)-dione | 9 |
| 5u | 6-hydroxy-2-(naphthalen-1-ylmethyl)-1,2,4-triazine-3,5(2H,4H)-dione | 0.05 |
| 5v | 6-hydroxy-2-(2-methoxyphenethyl)-1,2,4-triazine-3,5(2H,4H)-dione | 0.2 |
| 5vp | 6-hydroxy-2-(2-hydroxyphenethyl)-1,2,4-triazine-3,5(2H,4H)-dione | 0.06 |
| 5w | 6-hydroxy-2-(3-methoxyphenethyl)-1,2,4-triazine-3,5(2H,4H)-dione | 0.1 |
| 5wp | 6-hydroxy-2-(3-hydroxyphenethyl)-1,2,4-triazine-3,5(2H,4H)-dione | 0.1 |
| 5x | 6-hydroxy-2-(4-methoxyphenethyl)-1,2,4-triazine-3,5(2H,4H)-dione | 0.1 |
| 5xp | 6-hydroxy-2-(4-hydroxyphenethyl)-1,2,4-triazine-3,5(2H,4H)-dione | 0.1 |
| 5y | 2-(3,4-dichlorophenethyl)-6-hydroxy-1,2,4-triazine-3,5(2H,4H)-dione | 0.03 |
| 5z | 2-(3-chloro-4-fluorophenethyl)-6-hydroxy-1,2,4-triazine-3,5(2H,4H)-dione | 0.06 |
| 5aa | 6-hydroxy-2-(naphthalen-2-ylmethyl)-1,2,4-triazine-3,5(2H,4H)-dione | 0.03 |
| 5ab | 2-((6-fluoronaphthalen-2-yl)methyl)-6-hydroxy-1,2,4-triazine-3,5(2H,4H)-dione | 0.1 |
| 5ac | 6-hydroxy-2-(4-methoxyphenethyl)-1,2,4-triazine-3,5(2H,4H)-dione | 0.1 |
| 5ad | 6-hydroxy-2-(3-phenoxyphenethyl)-1,2,4-triazine-3,5(2H,4H)-dione | 0.3 |
| 5ae | 2-(4-(2-fluorophenoxy)benzyl)-6-hydroxy-1,2,4-triazine-3,5(2H,4H)-dione | 0.3 |
| 5af | 2-(biphenyl-4-ylmethyl)-6-hydroxy-1,2,4-triazine-3,5(2H,4H)-dione | 0.3 |
| 10a | 2-(2,2-Difluoro-2-phenylethyl)-6-hydroxy-1,2,4-triazine-3,5(2H,4H)-dione | 0.4 |
| 10b | 2-(3,4-difluorophenethyl)-6-hydroxy-1,2,4-triazine-3,5(2H,4H)-dione | 0.04 |
| 10c | 2-(2-(1H-pyrrol-1-yl)ethyl)-6-hydroxy-1,2,4-triazine-3,5(2H,4H)-dione | 0.1 |
| 10d | 2-(2-(1H-pyrazol-1-yl)ethyl)-6-hydroxy-1,2,4-triazine-3,5(2H,4H)-dione | 0.3 |
| 10e | 2-(2-(1H-indol-1-yl)ethyl)-6-hydroxy-1,2,4-triazine-3,5(2H,4H)-dione | 0.1 |
| 10f | 2-(2-(1H-benzo[d]imidazol-1-yl)ethyl)-6-hydroxy-1,2,4-triazine-3,5(2H,4H)-dione | 0.3 |
| 10g | 2-(2-(1H-pyrrolo[2,3-b]pyridin-1-yl)ethyl)-6-hydroxy-1,2,4-triazine-3,5(2H,4H)-dione | 0.3 |
| 10h | 2-(2-(1H-indazol-1-yl)ethyl)-6-hydroxy-1,2,4-triazine-3,5(2H,4H)-dione | 0.2 |
| 10i | 2-(2-(9H-carbazol-9-yl)ethyl)-6-hydroxy-1,2,4-triazine-3,5(2H,4H)-dione | 7 |
| 10j | 6-hydroxy-2-(2-morpholinoethyl)-1,2,4-triazine-3,5(2H,4H)-dione | 1 |
| 10k | 6-hydroxy-2-(1-phenylpropan-2-yl)-1,2,4-triazine-3,5(2H,4H)-dione | 0.3 |
| 10l | 6-hydroxy-2-(2-(pyridin-2-yl)ethyl)-1,2,4-triazine-3,5(2H,4H)-dione | 0.9 |
| 10m | 6-hydroxy-2-(perfluorophenyl)ethyl-1,2,4-triazine-3,5(2H,4H)-dione | 0.2 |
| 10n | 6-hydroxy-2-(((1R,2R)-2-phenylcyclopropyl)methyl)-1,2,4-triazine-3,5(2H,4H)-dione | 0.4 |
| 10o | 2-((1H-indol-4-yl)methyl)-6-hydroxy-1,2,4-triazine-3,5(2H,4H)-dione | 0.2 |

TABLE 1-continued

Inhibition of DAAO

| | Name | IC$_{50}$ (μM) |
|---|---|---|
| 10p | 6-hydroxy-2-(isoquinolin-5-ylmethyl)-1,2,4-triazine-3,5(2H,4H)-dione | 0.3 |
| 10q | 2-(benzo[b]thiophen-7-ylmethyl)-6-hydroxy-1,2,4-triazine-3,5(2H,4H)-dione | 2 |
| 10r | 2-(3,5-difluorophenethyl)-6-hydroxy-1,2,4-triazine-3,5(2H,4H)-dione | 0.2 |
| 10s | 2-((5-fluoronaphthalen-1-yl)methyl)-6-hydroxy-1,2,4-triazine-3,5(2H,4H)-dione | 0.08 |
| 10t | 2-(4-ethoxyphenethyl)-6-hydroxy-1,2,4-triazine-3,5(2H,4H)-dione | 0.3* |
| 10u | 6-Hydroxy-2-((2-methylnaphthalen-1-yl)methyl)-1,2,4-triazine-3,5(2H,4H)-dione | 0.6* |
| 12a | 2-(2-(dimethylamino)ethyl)-6-hydroxy-1,2,4-triazine-3,5(2H,4H)-dione | 5 |
| 12b | 6-hydroxy-2-(2-(4-isopropylpiperazin-1-yl)ethyl)-1,2,4-triazine-3,5(2H,4H)-dione | 9 |
| 12c | 2-(2-(4-(2-fluorophenyl)piperazin-1-yl)ethyl)-6-hydroxy-1,2,4-triazine-3,5(2H,4H)-dione | 3 |
| 12d | 2-(2-(3,4-dihydroisoquinolin-2(1H)-yl)ethyl)-6-hydroxy-1,2,4-triazine-3,5(2H,4H)-dione | 0.7 |
| 16 | 6-hydroxy-2-phenethyl-3-thioxo-3,4-dihydro-1,2,4-triazin-5(2H)-one | 0.05 |
| 20 | 6-hydroxy-2-(2-oxo-2-phenylethyl)-1,2,4-triazine-3,5 (2H,4H)-dione | 1 |
| 21 | 6-hydroxy-2-(2-hydroxy-2-phenylethyl)-1,2,4-triazine-3,5(2H,4H)-dione | 1.0 |
| 25a | 6-hydroxy-2-(quinolin-8-ylmethyl)-1,2,4-triazine-3,5(2H,4H)-dione | 3.0 |
| 25b | 2-((4-fluoronaphthalen-1-yl)methyl)-6-hydroxy-1,2,4-triazine-3,5(2H,4H)-dione | 0.2 |
| 25c | 6-hydroxy-2-((4-methylnaphthalen-1-yl)methyl)-1,2,4-triazine-3,5(2H,4H)-dione | 1.0 |
| 25d | 2-((6-bromonaphthalen-1-yl)methyl)-6-hydroxy-1,2,4-triazine-3,5(2H,4H)-dione | 0.05 |
| 30 | 2-(2-(2'-fluorobiphenyl-4-yl)ethyl)-6-hydroxy-1,2,4-triazine-3,5(2H,4H)-dione | 0.08 |
| 32 | 6-hydroxy-2-(4-morpholinophenethyl)-1,2,4-triazine-3,5(2H,4H)-dione | 1.0* |

*Porcine DAAO was used to measure inhibitory potency.

Example 70

Effect of 6-hydroxy-2-(naphthalen-1-ylmethyl)-1,2,4-triazine-3,5(2H,4H)-dione on D-serine levels in plasma D-serine or DAAO inhibitor plus D-serine are reconstituted on the day of the experiment in 0.5% methylcellulose (3 mg/ml). Male CD1 mice are co-administered with 6-hydroxy-2-(naphthalen-1-ylmethyl)-1,2,4-triazine-3,5(2H,4H)-dione 5u (30 mg/kg) and D-serine (30 mg/kg) p.o. single dose (dosing volume 10 ml/kg). Control animals are given D-serine alone. Mice are sacrificed by $CO_2$ inhalation at 0.5, 1, 2, 3 and 6 h after dosing (n=3 for each time point). Blood is collected by cardiac puncture and centrifuged in plasma separator tubes at 3000 rpm for 10 min. Plasma is stored at −80° C. until analysis. To determine D-serine levels, plasma is thawed and a 10 μL aliquot is added to siliconized tubes. Proteins are precipitated by the addition of methanol (500 μL) with L-Serine-d$_3$ (0.1 μM) as internal standard. Samples are centrifuged at 16,000×g for 10 min at 4° C. Supernatants (250 μL) are transferred to a new tube and dried at 45° C. Samples are derivatized with Marfey's reagent (10 μL, 1% in acetone) in the presence of sodium bicarbonate (40 μL, pH 8.5, 50 mM). The derivatization reaction is carried out for 90 minutes at 60° C. After this time, samples are centrifuged at 16,000×g for 10 min at 4° C. and a 35 μL aliquot is transferred to a 96-well plate. Derivatized samples (20 μL) are separated on an Agilent 1290 UPLC system with a $C_{18}$ column using a isocratic run of 80:20 (water:acetonitrile) with 0.1% formic acid over 7 minutes and detected on a mass spectrometer (Agilent 6520 QTOF mass spectrometer). The results are summarized in FIG. 1.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Arana G W. An overview of side effects caused by typical antipsychotics. J Clin Psychiatry. 2000; 61 Suppl 8:5-11; discussion 2-3.

Shirzadi A A, Ghaemi S N. Side effects of atypical antipsychotics: extrapyramidal symptoms and the metabolic syndrome. Harv Rev Psychiatry. 2006; 14(3):152-64.

Coyle J T. Glutamate and schizophrenia: beyond the dopamine hypothesis. Cell Mol Neurobiol. 2006; 26(4-6): 365-84.

Javitt D C, Zukin S R. Recent advances in the phencyclidine model of schizophrenia. Am J Psychiatry. 1991; 148(10): 1301-8.

Krystal J H, Karper L P, Seibyl J P, Freeman G K, Delaney R, Bremner J D, Heninger G R, Bowers M B, Jr., Charney D S. Subanesthetic effects of the noncompetitive NMDA antagonist, ketamine, in humans. Psychotomimetic, perceptual, cognitive, and neuroendocrine responses. Arch Gen Psychiatry. 1994; 51(3):199-214.

Yang C R, Svensson K A. Allosteric modulation of NMDA receptor via elevation of brain glycine and D-serine: the therapeutic potentials for schizophrenia. Pharmacol Ther. 2008; 120(3):317-32.

Leiderman E, Zylberman I, Zukin S R, Cooper T B, Javitt D C. Preliminary investigation of high-dose oral glycine on serum levels and negative symptoms in schizophrenia: an open-label trial. Biol Psychiatry. 1996; 39(3):213-5.

Javitt D C. Glycine transport inhibitors for the treatment of schizophrenia: symptom and disease modification. Curr Opin Drug Discov Devel. 2009; 12(4):468-78.

Bridges T M, Williams R, Lindsley C W. Design of potent GlyT1 inhibitors: in vitro and in vivo profiles. Curr Opin Mol Ther. 2008; 10(6):591-601.

Hashimoto A, Nishikawa T, Hayashi T, Fujii N, Harada K, Oka T, Takahashi K. The presence of free D-serine in rat brain. FEBS Lett. 1992; 296(1):33-6.

Nagata Y, Horiike K, Maeda T. Distribution of free D-serine in vertebrate brains. Brain Res. 1994; 634(2):291-5.

Hashimoto A, Nishikawa T, Oka T, Takahashi K. Endogenous D-serine in rat brain: N-methyl-D-aspartate receptor-related distribution and aging. J Neurochem. 1993; 60(2):783-6.

Oldendorf W H. Brain uptake of radiolabeled amino acids, amines, and hexoses after arterial injection. Am J Physiol. 1971; 221(6):1629-39.

Hashimoto A, Chiba Y. Effect of systemic administration of D-serine on the levels of D- and L-serine in several brain areas and periphery of rat. Eur J Pharmacol. 2004; 495 (2-3):153-8.

Matsui T, Sekiguchi M, Hashimoto A, Tomita U, Nishikawa T, Wada K. Functional comparison of D-serine and glycine in rodents: the effect on cloned NMDA receptors and the extracellular concentration. J Neurochem. 1995; 65(1):454-8.

Tsai G, Yang P, Chung L C, Lange N, Coyle J T. D-serine added to antipsychotics for the treatment of schizophrenia. Biol Psychiatry. 1998; 44(11):1081-9.

Heresco-Levy U, Javitt D C, Ebstein R, Vass A, Lichtenberg P, Bar G, Catinari S, Ermilov M. D-serine efficacy as add-on pharmacotherapy to risperidone and olanzapine for treatment-refractory schizophrenia. Biol Psychiatry. 2005; 57(6):577-85.

Ganote C E, Peterson D R, Carone F A. The nature of D-serine-induced nephrotoxicity. Am J Pathol. 1974; 77(2):269-82.

Williams R E, Lock E A. Sodium benzoate attenuates d-serine induced nephrotoxicity in the rat. Toxicology. 2005; 207(1):35-48.

Burnet P W, Eastwood S L, Bristow G C, Godlewska B R, Sikka P, Walker M, Harrison P J. D-amino acid oxidase activity and expression are increased in schizophrenia. Mol Psychiatry. 2008; 13(7):658-60. PMCID: 2629619.

Madeira C, Freitas M E, Vargas-Lopes C, Wolosker H, Panizzutti R. Increased brain D-amino acid oxidase (DAAO) activity in schizophrenia. Schizophr Res. 2008; 101(1-3):76-83.

Curti B, Ronchi S, Simonetta P M. D- and L-Amino Acid Oxidases. In: Muller F, editor. Chemistry and Biochemistry of Flavoenzyme. Boca Raton, Fla.: CRC Press; 1992. p. 69-94.

Adage T, Trillat A C, Quattropani A, Perrin D, Cavarec L, Shaw J, Guerassimenko O, Giachetti C, Greco B, Chumakov I, Halazy S, Roach A, Zaratin P. In vitro and in vivo pharmacological profile of AS057278, a selective d-amino acid oxidase inhibitor with potential anti-psychotic properties. Eur Neuropsychopharmacol. 2008; 18(3):200-14.

Smith S M, Uslaner J M, Yao L, Mullins C M, Surles N O, Huszar S L, McNaughton C H, Pascarella D M, Kandebo M, Hinchliffe R M, Sparey T, Brandon N J, Jones B, Venkatraman S, Young M B, Sachs N, Jacobson M A, Hutson P H. The behavioral and neurochemical effects of a novel D-amino acid oxidase inhibitor compound 8 [4H-thieno[3,2-b]pyrrole-5-carboxylic acid] and D-serine. J Pharmacol Exp Ther. 2009; 328(3):921-30.

Horiike K, Tojo H, Arai R, Nozaki M, Maeda T. D-aminoacid oxidase is confined to the lower brain stem and cerebellum in rat brain: regional differentiation of astrocytes. Brain Res. 1994; 652(2):297-303.

Hashimoto A, Nishikawa T, Konno R, Niwa A, Yasumura Y, Oka T, Takahashi K. Free D-serine, D-aspartate and D-alanine in central nervous system and serum in mutant mice lacking D-amino acid oxidase. Neurosci Lett. 1993; 152(1-2):33-6.

Boomsma F, Meerwaldt J D, Man in't Veld A J, Hovestadt A, Schalekamp M A. Treatment of idiopathic parkinsonism with L-dopa in the absence and presence of decarboxylase inhibitors: effects on plasma levels of L-dopa, dopa decarboxylase, catecholamines and 3-O-methyldopa. J Neurol. 1989; 236(4):223-30.

Ferraris D, Duvall B, Ko Y S, Thomas A G, Rojas C, Majer P, Hashimoto K, Tsukamoto T. Synthesis and biological evaluation of D-amino acid oxidase inhibitors. J Med Chem. 2008; 51(12):3357-9.

Mattevi A, Vanoni M A, Todone F, Rizzi M, Teplyakov A, Coda A, Bolognesi M, Curti B. Crystal structure of D-amino acid oxidase: a case of active site mirror-image convergent evolution with flavocytochrome b2. Proc Natl Acad Sci USA. 1996; 93(15):7496-501.

Fukushima T, Kawai J, Imai K, Toyo'oka T. Simultaneous determination of D- and L-serine in rat brain microdialysis sample using a column-switching HPLC with fluorimetric detection. Biomed Chromatogr. 2004; 18(10):813-9.

Hashimoto K, Fujita Y, Horio M, Kunitachi S, Iyo M, Ferraris D, Tsukamoto T. Co-administration of a D-amino acid oxidase inhibitor potentiates the efficacy of D-serine in attenuating prepulse inhibition deficits after administration of dizocilpine. Biol Psychiatry. 2009; 65(12):1103-6.

Rishton G M. Nonleadlikeness and leadlikeness in biochemical screening. Drug Discov Today. 2003; 8(2):86-96.

Duplantier A J, Becker S L, Bohanon M J, Borzilleri K A, Chrunyk B A, Downs J T, Hu L Y, El-Kattan A, James L C, Liu S, Lu J, Maklad N, Mansour M N, Mente S, Piotrowski M A, Sakya S M, Sheehan S, Steyn S J, Strick C A, Williams V A, Zhang L. Discovery, SAR, and pharmacokinetics of a novel 3-hydroxyquinolin-2(1H)-one series of potent D-amino acid oxidase (DAAO) inhibitors. J Med Chem. 2009; 52(11):3576-85.

Sparey T, Abeywickrema P, Almond S, Brandon N, Byrne N, Campbell A, Hutson P H, Jacobson M, Jones B, Munshi S, Pascarella D, Pike A, Prasad G S, Sachs N, Sakatis M, Sardana V, Venkatraman S, Young M B. The discovery of fused pyrrole carboxylic acids as novel, potent D-amino acid oxidase (DAO) inhibitors. Bioorg Med Chem Lett. 2008; 18(11):3386-91.

Seillier A, Giuffrida A. Evaluation of NMDA receptor models of schizophrenia: divergences in the behavioral effects of sub-chronic PCP and MK-801. Behav Brain Res. 2009; 204(2):410-5.

Kellendonk C, Simpson E H, Kandel E R. Modeling cognitive endophenotypes of schizophrenia in mice. Trends Neurosci. 2009; 32(6):347-58.

Harrison P J, Weinberger D R. Schizophrenia genes, gene expression, and neuropathology: on the matter of their convergence. Mol Psychiatry. 2005; 10(1):40-68.

Jaaro-Peled H, Hayashi-Takagi A, Seshadri S, Kamiya A, Brandon N J, Sawa A. Neurodevelopmental mechanisms of schizophrenia: understanding disturbed postnatal brain maturation through neuregulin-1-ErbB4 and DISC1. Trends Neurosci. 2009; 32(9):485-95.

Hikida T, Jaaro-Peled H, Seshadri S, Oishi K, Hookway C, Kong S, Wu D, Xue R, Andrade M, Tankou S, Mori S, Gallagher M, Ishizuka K, Pletnikov M, Kida S, Sawa A. Dominant-negative DISC1 transgenic mice display schizophrenia-associated phenotypes detected by measures translatable to humans. Proc Natl Acad Sci USA. 2007; 104(36):14501-6. PMCID: 1964873.

Li W, Zhou Y, Jentsch J D, Brown R A, Tian X, Ehninger D, Hennah W, Peltonen L, Lonnqvist J, Huttunen M O, Kaprio J, Trachtenberg J T, Silva A J, Cannon T D. Specific developmental disruption of disrupted-in-schizophrenia-1 function results in schizophrenia-related phenotypes in mice. Proc Natl Acad Sci USA. 2007; 104(46):18280-5. PMCID: 2084334.

Pletnikov M V, Ayhan Y, Nikolskaia O, Xu Y, Ovanesov M V, Huang H, Mori S, Moran T H, Ross C A. Inducible expression of mutant human DISC1 in mice is associated with brain and behavioral abnormalities reminiscent of schizophrenia. Mol Psychiatry. 2008; 13(2):173-86, 15.

Reddy A C S, Narsaiah B, Venkataratnam R V. A Novel Method for the Synthesis of Isoxazolo and Pyrazolo Pyridines Using Hypervalent Iodine Reagent. Synthetic Commun 1997; 27(13):2217-22.

Drummond J, Johnson G, Nickell D G, Ortwine D F, Bruns R F, Welbaum B. Evaluation and synthesis of aminohydroxyisoxazoles and pyrazoles as potential glycine agonists. J Med Chem. 1989; 32(9):2116-28.

Trivedi K, Sethan S. Notes—3-Hydroxycoumarins. J Org Chem. 1980; 25(10):1817-9.

Pave G, Chalard P, Viaud-Massuard M-C, Troin Y, Guillaumet G. New Efficient Synthesis of Pyrido[2,3-c] and Pyrido[3,2-c]coumarin Derivatives. Synlett. 2003(07):987-90.

Bailly F, Maurin C, Teissier E, Vezin H, Cotelle P. Antioxidant properties of 3-hydroxycoumarin derivatives. Bioorg Med Chem. 2004; 12(21):5611-8.

Chiyoda T, Iida K, Takatori K, Kajiwara M. Convenient Synthesis of 1,2-Benzisothiazol-3(2H)-ones by Cyclization Reaction of Acyl Azide. Synlett. 2000; 2000(10):1427-8.

Sekikawa I, Nishie J, Tono-Oka S, Tanaka Y, Kakimoto S. Antituberculous compounds. XXVIII. Synthesis of pyrazolopyridines. J Heterocyclic Chem. 1973; 10(6):931-2.

Wyrick S D, Voorstad P J, Cocolas G, Hall I H. Hypolipidemic activity of phthalimide derivatives. 7. Structure-activity studies of indazolone analogues. J Med Chem. 1984; 27(6):768-72.

Valgeirsson J, Nielsen E O, Peters D, Mathiesen C, Kristensen A S, Madsen U. Bioisosteric modifications of 2-arylureidobenzoic acids: selective noncompetitive antagonists for the homomeric kainate receptor subtype GluR5. J Med Chem. 2004; 47(27):6948-57.

Usami N, Kitahara K, Ishikura S, Nagano M, Sakai S, Hara A. Characterization of a major form of human isatin reductase and the reduced metabolite. Eur J Biochem. 2001; 268(22):5755-63.

Cooley J H, Jacobs P T. Oxidative ring closure of 1-benzyloxy-3-arylureas to 1-benzyloxybenzimidazolones. J Org Chem. 1975; 40(5):552-7.

Cafiero C, A. P, French C S, McFarlane M D, Mackie R K, Smith D M. o-Nitroaniline derivatives. Part 14. Cyclizations leading to benzimidazole N-oxides, N-hydroxybenzimidazolones and N-hydroxyqinoxaline-2,3-diones: a mechanistic borderline. J Chem Soc, Perkin Trans 1. 1997:1375-84.

Veber D F, Johnson S R, Cheng H Y, Smith B R, Ward K W, Kopple K D. Molecular properties that influence the oral bioavailability of drug candidates. J Med Chem. 2002; 45(12):2615-23.

Lipina T, Labrie V, Weiner I, Roder J. Modulators of the glycine site on NMDA receptors, D-serine and ALX 5407, display similar beneficial effects to clozapine in mouse models of schizophrenia. Psychopharmacology (Berl). 2005; 179(1):54-67.

Hikida T, Mustafa A K, Maeda K, Fujii K, Barrow R K, Saleh M, Huganir R L, Snyder S H, Hashimoto K, Sawa A. Modulation of D-serine levels in brains of mice lacking PICK1. Biol Psychiatry. 2008; 63(10):997-1000. PMCID: 2715963.

Labrie V, Fukumura R, Rastogi A, Fick U, Wang W, Boutros P C, Kennedy J L, Semeralul M O, Lee F H, Baker G B, Belsham D D, Barger S W, Gondo Y, Wong A H, Roder J C. Serine racemase is associated with schizophrenia susceptibility in humans and in a mouse model. Hum Mol Genet. 2009; 18(17):3227-43. PMCID: 2722985.

Sethuraman R, Lee T L, Tachibana S. D-serine regulation: a possible therapeutic approach for central nervous diseases and chronic pain. Mini Rev Med Chem. 2009; 9(7):813-9.

McDonald, A. J., 1996. Glutamate and aspartate immunoreactive neurons of the rat basolateral amygdale: colocalization of excitatory amino acids and projections to the limbic circuit. *Journal of Comparative Neurology* 365, 367-379.

Heresco-Levy U, Vass A, Boaz B, Wolosker H, Dumin E, Balan L, Deutsch L, and Kremer I, 2009. *International Journal of Neuropsychopharmacology*, 12. 1275-1282.

Cook A J, Woolf C J, Wall P D, McMahon S B, 1987. Dynamic receptive field plasticity in rat spinal cord dorsal horn following C-primary afferent input. *Nature* 325:151-153.

Ying B, Lu N, Zhang Y Q, and Zhao Z Q, 2006. Involvement of spinal glia in tetanically sciatic stimulation-induced bilateral mechanical allodynia in rats. *Biochem Biophys Res Commun* 340: 1264-1272.

Lu J-M, Gong N, Wang Y-C, and Wang Y-X, 2012. D-Amino acid oxidase-mediated increase in spinal hydrogen peroxide is mainly responsible for formalin-induced tonic pain. *British J of Pharmacology* 165:1941-1955.

Media Release, "Phase II study with first-in-class investigational drug demonstrates improvement in negative symptoms in patients with schizophrenia," F. Hoffmann-La Roche, Ltd. (Dec. 6, 2010).

Kantrowitz J. T., et al., "High dose D-serine in the treatment of schizophrenia," *Schizophrenia Research* 121:125-130 (2010).

Maekawa M., et al., "D-Amino-acid Oxidase Is Involved in D-Serine-Induced Nephrotoxicity," *Chem. Res. Toxicol.* 18:1678-1682 (2005).

International PCT Patent Application Publication No. WO2013/073577 A1, for "Dihydroxy Aromatic Heterocyclic Compound," to Hondo, T., et al., published May 23, 2013.

International PCT Patent Application Publication No. WO2013/004996 A1, for "5- or 6-Substituted 3-Hydroxy-2 (1H)-Pyridinones as D-Amino Acid Oxidase (DAAO) Inhibitors in Therapy of Diseases such as Schizophrenia, Cognitive Disorder and Pain," to Farnaby, W., et al., published Jan. 10, 2013.

International PCT Patent Application Publication No. WO2013/027000 A1, for "Pyridazinone Compounds and their use as DAAO Inhibitors," to Farnaby, W., et al., published Feb. 28, 2013.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

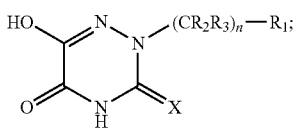

wherein:
n is an integer selected from the group consisting of 1, 2, and 3;
X is oxygen or sulfur;
$R_1$ is selected from the group consisting of ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, substituted cyclopropyl, amino, carboxyl, substituted or unsubstituted phenyl, substituted or unsubstituted naphthyl, substituted or unsubstituted biphenyl, substituted or unsubstituted pyridinyl, substituted or unsubstituted pyrrolyl, substituted or unsubstituted pyrazolyl, substituted or unsubstituted carbazolyl, substituted or unsubstituted indazolyl, substituted or unsubstituted indolyl, substituted or unsubstituted piperazinyl, substituted or unsubstituted morpholinyl, substituted or unsubstituted thienyl, substituted or unsubstituted quinolinyl, substituted or unsubstituted isoquinolinyl, substituted or unsubstituted benzo[b]thiophenyl, substituted or unsubstituted 1H-benzo[d]imidazolyl, substituted or unsubstituted 1H-pyrrolo[2,3-b]pyridinyl, and substituted or unsubstituted 1H-pyrrol[2,3-b]pyridinyl; and
each occurrence of $R_2$ and $R_3$ is independently selected from the group consisting of H, hydroxyl, and halogen, or $R_2$ and $R_3$ together can be oxygen;
or a pharmaceutically acceptable salt thereof.

2. The compound of claim 1, wherein $R_1$ is selected from the group consisting of isopentyl, 3,3-dimethylbutyl, dimethylamino, phenyl, 2-fluorophenyl, 3-fluorophenyl, 4-fluorophenyl, 2-chlorophenyl, 3-chlorophenyl, 4-chlorophenyl, 2,4-dichlorophenyl, 3,4-dichlorophenyl, 2,2-difluorophenyl, 3,4-difluorophenyl, 3,5-difluorophenyl, 3-chloro-4-fluorophenyl, 3-(trifluoromethyl)phenyl, 4-(trifluoromethyl)phenyl, perfluorophenyl, 2-methylphenyl, 3-methylphenyl, 4-methylphenyl, 2-hydroxyphenyl, 3-hydroxyphenyl, 4-hydroxyphenyl, 2-methoxyphenyl, 3-methoxyphenyl, 4-methoxyphenyl, 4-ethoxyphenyl, 3-phenoxyphenyl, 2-fluorophenoxyphenyl, 2-oxo-phenyl, 4-morpholinophenyl, naphthyl, 2-methylnaphthyl, 4-methylnaphthyl, 4-fluoronaphthyl, 5-fluoronaphthyl, 6-bromonaphthyl, 6-fluoronaphthyl, biphenyl, 2'-fluorobiphenyl, pyridinyl, morpholino, quinolinyl, isoquinolinyl, 1H-pyrrolyl, 1H-indolyl, 1H-indazolyl, 9H-carbazolyl, 1H-benzo[d]imidazolyl, 1H-pyrrolo[2,3-b]pyridinyl, benzo[b]thiophenyl, 4-isopropylpiperazinyl, (2-fluorophenyl)piperazinyl, 3,4-dihydroisoquinolinyl, and phenylcyclopropyl.

3. The compound of claim 1, wherein the compound of formula (I) is selected from the group consisting of: 6-hydroxy-2-phenethyl-1,2,4-triazine-3,5(2H,4H)-dione; 2-(4-fluorophenethyl)-6-hydroxy-1,2,4-triazine-3,5(2H,4H)-dione; 2-(3-fluorophenethyl)-6-hydroxy-1,2,4-triazine-3,5(2H,4H)-dione; 2-(2-fluorophenethyl)-6-hydroxy-1,2,4-triazine-3,5(2H,4H)-dione; 2-(4-chloropisohenethyl)-6-hydroxy-1,2,4-triazine-3,5(2H,4H)-dione; 2-(3-chlorophenethyl)-6-hydroxy-1,2,4-triazine-3,5(2H,4H)-dione; 2-(2-chlorophenethyl)-6-hydroxy-1,2,4-triazine-3,5(2H,4H)-dione; 6-hydroxy-2-(4-methylphenethyl)-1,2,4-triazine-3,5(2H,4H)-dione; 6-hydroxy-2-(3-methylphenethyl)-1,2,4-triazine-3,5(2H,4H)-dione; 6-hydroxy-2-(2-methylphenethyl)-1,2,4-triazine-3,5(2H,4H)-dione; 6-hydroxy-2-(4-(trifluoromethyl)phenethyl)-1,2,4-triazine-3,5(2H,4H)-dione; 6-hydroxy-2-(3-(trifluoromethyl)phenethyl)-1,2,4-triazine-3,5(2H,4H)-dione; 2-(2,4-dichlorophenethyl)-6-hydroxy-1,2,4-triazine-3,5(2H,4H)-dione; 6-hydroxy-2-(2-(naphthalen-1-yl)ethyl)-1,2,4-triazine-3,5(2H,4H)-dione; 2-(2-(biphenyl-4-yl)ethyl)-6-hydroxy-1,2,4-triazine-3,5(2H,4H)-dione; 6-hydroxy-2-isopentyl-1,2,4-triazine-3,5(2H,4H)-dione; 2-(3,3-dimethylbutyl)-6-hydroxy-1,2,4-triazine-3,5(2H,4H)-dione; 6-hydroxy-2-(3-phenylpropyl)-1,2,4-triazine-3,5(2H,4H)-dione; 2-benzyl-6-hydroxy-1,2,4-triazine-3,5(2H,4H)-dione; 6-hydroxy-2-(naphthalen-1-ylmethyl)-1,2,4-triazine-3,5(2H,4H)-dione; 6-hydroxy-2-(2-methoxyphenethyl)-1,2,4-triazine-3,5(2H,4H)-dione; 6-hydroxy-2-(2-hydroxyphenethyl)-1,2,4-triazine-3,5(2H,4H)-dione; 6-hydroxy-2-(3-methoxyphenethyl)-1,2,4-triazine-3,5(2H,4H)-dione; 6-hydroxy-2-(3-hydroxyphenethyl)-1,2,4-triazine-3,5(2H,4H)-dione; 6-hydroxy-2-(4-methoxyphenethyl)-1,2,4-triazine-3,5(2H,4H)-dione; 6-hydroxy-2-(4-hydroxyphenethyl)-1,2,4-triazine-3,5(2H,4H)-dione; 2-(3,4-dichlorophenethyl)-6-hydroxy-1,2,4-triazine-3,5(2H,4H)-dione; 2-(3-chloro-4-fluorophenethyl)-6-hydroxy-1,2,4-triazine-3,5(2H,4H)-dione; 6-hydroxy-2-(naphthalen-2-ylmethyl)-1,2,4-triazine-3,5(2H,4H)-dione; 24(6-fluoronaphthalen-2-yl)methyl)-6-hydroxy-1,2,4-triazine-3,5(2H,4H)-dione; 6-hydroxy-2-(4-methoxyphenethyl)-1,2,4-triazine-3,5(2H,4H)-dione; 6-hydroxy-2-(3-phenoxyphenethyl)-1,2,4-triazine-3,5(2H,4H)-dione; 2-(4-(2-fluorophenoxy)benzyl)-6-hydroxy-1,2,4-triazine-3,5(2H,4H)-dione; 2-(biphenyl-4-ylmethyl)-6-hydroxy-1,2,4-triazine-3,5(2H,4H)-dione; 2-(2,2-Difluoro-2-phenylethyl)-6-hydroxy-1,2,4-triazine-3,5(2H,4H)-dione; 2-(3,4-difluorophenethyl)-6-hydroxy-1,2,4-triazine-3,5(2H,4H)-dione; 2-(2-(1H-pyrrol-1-yl)ethyl)-6-hydroxy-1,2,4-triazine-3,5(2H,4H)-dione; 2-(2-(1H-pyrazol-1-yl)ethyl)-6-hydroxy-1,2,4-triazine-3,5(2H,4H)-dione; 2-(2-(1H-indol- 1-yl)ethyl)-6-hydroxy-1,2,4-triazine-3,5(2H,4H)-dione; 2-(2-(1H-benzo[d]imidazol-1-yl)ethyl)-6-hydroxy-1,2,4-triazine-3,5(2H,4H)-dione; 2-(2-(1H-pyrrolo[2,3-b]pyridin-1-yl)ethyl)-6-hydroxy-1,2,4-triazine-3,5(2H,4H)-dione; 2-(2-(1H-indazol-1-yl)ethyl)-6-hydroxy-1,2,4-triazine-3,5(2H,4H)-dione; 2-(2-(9H-carbazol-9-yl)ethyl)-6-hydroxy-1,2,4-triazine-3,5(2H,4H)-dione; 6-hydroxy-2-(2-morpholinoethyl)-1,2,4-triazine-3,5(2H,4H)-dione; 6-hydroxy-2-(1-phenylpropan-2-yl)-1,2,4-triazine-3,5(2H,4H)-dione; 6-hydroxy-2-(2-(pyridin-2-yl)ethyl)-1,2,4-triazine-3,5(2H,4H)-dione; 6-hydroxy-2-((perfluorophenyl)ethyl)-1,2,4-triazine-3,5(2H,4H)-dione; 6-hydroxy-2-(((1R,2R)-2-phenylcyclopropyl)methyl)-1,2,4-triazine-3,5(2H,4H)-dione; 2-((1H-indol-4-yl)methyl)-6-hydroxy-1,2,4-triazine-3,5(2H,4H)-dione; 6-hydroxy-2-(isoquinolin-5-ylmethyl)-1,2,4-triazine-3,5(2H,4H)-dione; 2-(benzo[b]thiophen-7-ylmethyl)-6-hydroxy-1,2,4-triazine-3,5(2H,4H)-dione; 2-(3,5-difluorophenethyl)-6-hydroxy-1,2,4-triazine-3,5(2H,4H)-dione; 2-((5-fluoronaphthalen-1-yl)methyl)-6-hydroxy-1,2,4-triazine-3,5(2H,4H)-dione; 2-(4-ethoxyphenethyl)-6-hydroxy-1,2,4-triazine-3,5(2H,4H)-dione; 6-hydroxy-2-((2-methylnaphthalen-1-yl)methyl)-1,2,4-triazine-3,5(2H,4H)-dione; 2-(2-(dimethylamino)ethyl)-6-hydroxy-1,2,4-triazine-3,5(2H,4H)-dione; 6-hydroxy-2-(2-(4-isopropylpiperazin-1-yl)ethyl)-1,2,4-triazine-3,5(2H,4H)-dione; 2-(2-(4-(2-fluorophenyl)piperazin-1-yl)ethyl)-6-hydroxy-1,2,4-triazine-3,5(2H,4H)-dione; 2-(2-(3,4-dihydroisoquinolin-2(1H)-yl)ethyl)-6-hydroxy-1,2,4-triazine-3,5(2H,4H)-dione; 6-hydroxy-2-phenethyl-3-thioxo-3,4-dihydro-1,2,4-triazin-5(2H)-one; 6-hydroxy-2-(2-oxo-2-phenylethyl)-1,2,4-triazine-3,5(2H,4H)-dione; 6-hydroxy-2-(2-hydroxy-2-phenylethyl)-1,2,4-triazine-3,5(2H,4H)-dione; 6-hydroxy-2-(quinolin-8-ylmethyl)-1,2,4-triazine-3,5(2H,4H)-dione; 2-((4-fluoronaphthalen-1-yl)methyl)-6-hydroxy-1,2,4-triazine-3,5(2H,4H)-dione; 6-hydroxy-2-((4-methylnaphthalen-1-yl)methyl)-1,2,4-triazine-3,5(2H,4H)-dione; 2-((6-bromonaphthalen-1-yl)methyl)-6-hydroxy-1,2,4-triazine-3,5(2H,4H)-dione; 2-(2-(2'-fluorobiphenyl-4-yl)ethyl)-6-hydroxy-1,2,4-triazine-3,5(2H,4H)-dione; and 6-hydroxy-2-(4-morpholinophenethyl)-1,2,4-triazine-3,5(2H,4H)-dione.

4. A composition comprising a pharmaceutically effective amount of a compound of claim 1 or a pharmaceutically acceptable salt thereof, and a pharmaceutically acceptable carrier.

5. The composition of claim 4, further comprising a therapeutically effective combination of D-serine or D-alanine and a compound of formula (I).

* * * * *